United States Patent
Cheng et al.

(10) Patent No.: US 12,312,355 B2
(45) Date of Patent: May 27, 2025

(54) 1H-[1, 2, 3]TRIAZOLO[4, 5-H] QUINAZOLINE COMPOUNDS ACTING AS PROTEIN KINASE INHIBITORS

(71) Applicant: CHENGDU CYNOGEN BIO-PHARMACEUTICAL TECHNOLOGY CO., LTD., Sichuan (CN)

(72) Inventors: Hang Cheng, Sichuan (CN); Weiyan Xiong, Sichuan (CN); Bin Yu, Sichuan (CN)

(73) Assignee: CHENGDU CYNOGEN BIO-PHARMACEUTICAL TECHNOLOGY CO., LTD., Sichuan (CN)

( * ) Notice: Subject to any disclaimer, the term of this patent is extended or adjusted under 35 U.S.C. 154(b) by 727 days.

(21) Appl. No.: 17/632,132

(22) PCT Filed: Jul. 31, 2020

(86) PCT No.: PCT/CN2020/106158
§ 371 (c)(1),
(2) Date: Feb. 1, 2022

(87) PCT Pub. No.: WO2021/023104
PCT Pub. Date: Feb. 11, 2021

(65) Prior Publication Data
US 2022/0281878 A1 Sep. 8, 2022

(30) Foreign Application Priority Data
Aug. 2, 2019 (CN) .......................... 201910712009.8

(51) Int. Cl.
| | | |
|---|---|---|
| *C07D 487/04* | (2006.01) | |
| *A61K 31/519* | (2006.01) | |
| *A61K 31/5377* | (2006.01) | |
| *A61K 31/541* | (2006.01) | |
| *A61K 45/06* | (2006.01) | |
| *A61P 35/00* | (2006.01) | |

(52) U.S. Cl.
CPC .......... *C07D 487/04* (2013.01); *A61K 31/519* (2013.01); *A61K 31/5377* (2013.01); *A61K 31/541* (2013.01); *A61K 45/06* (2013.01); *A61P 35/00* (2018.01)

(58) Field of Classification Search
CPC ................ C07D 487/04; A61K 31/519; A61K 31/5377; A61K 31/541; A61K 45/06; A61P 35/00
See application file for complete search history.

(56) References Cited

U.S. PATENT DOCUMENTS 11,365,196 B2 * 6/2022 Xu ........................ C07D 471/14

FOREIGN PATENT DOCUMENTS

| CN | 1849325 A | 10/2006 |
|---|---|---|
| CN | 103339134 A | 10/2013 |
| WO | 2018177403 A1 | 10/2018 |
| WO | 2018214846 A1 | 11/2018 |
| WO | 2019029663 A1 | 2/2019 |

OTHER PUBLICATIONS

International Search Report for PCT/CN2020/106158 with English Translation mailed Oct. 29, 2020, 25 pages.

* cited by examiner

*Primary Examiner* — Joseph K McKane
*Assistant Examiner* — Anna Grace Kuckla
(74) *Attorney, Agent, or Firm* — Lowenstein Sandler LLP

(57) ABSTRACT

Provided in the present invention are 1H-[1, 2, 3]triazolo[4, 5-h] quinazoline compounds of general formula (I), which can be used for treating cell proliferative disorders. The new compounds of the present invention are effective inhibitors of cyclin-dependent kinases (CDK).

21 Claims, No Drawings

1H-[1, 2, 3]TRIAZOLO[4, 5-H] QUINAZOLINE COMPOUNDS ACTING AS PROTEIN KINASE INHIBITORS

CROSS-REFERENCE TO RELATED APPLICATIONS

The present application is a national application of PCT/CN2020/106158 filed on Jul. 31, 2020, which claims the priority of the Chinese Patent Application No. 201910712009.8 filed on Aug. 2, 2019. The Chinese Patent Application No. 201910712009.8 is incorporated herein by reference as part of the disclosure of the present application.

FIELD OF THE INVENTION

The present disclosure provides a 1H-[1,2,3]triazolo[4,5-h]quinazoline compound as a cyclin-dependent kinase (CDK) inhibitor, which has broad-spectrum and strong inhibitory activity on CDK. The compounds of the present invention are effective for treating cancer, inflammation and other diseases.

BACKGROUND OF THE INVENTION

The Cyclin dependent kinase (CDK) and cyclin are important factors in cell cycle regulation. CDK can combine with cyclin to form heterodimer, in which CDK is the catalytic subunit and cyclin is the regulatory subunit, forming various cyclin-CDK complexes, phosphorylating different substrates, and promoting and transforming different phases of the cell cycle.

In recent ten years, CDK inhibitors have become a hot spot in the development of new antitumor drugs, and more than 20 CDK inhibitors have entered the clinical stage. Although the preclinical pharmacodynamic results of CDK inhibitors are significant, the results of most clinical trials are unsatisfactory. The main problems include lack of efficacy and high toxicity in solid tumors. Some CDK inhibitors lack selectivity to CDK subtypes, so they have highly toxic side effects.

CDK4 and CDK6 are two closely related kinases that combine with Cyclin D during the tumor cell cycle to promote the G1 phase to the S phase, which is necessary for cell cycle progression. It has been proven in human tumors (such as breast cancer and myeloma), the activation of CDK4 and CDK6 leads to cell cycle changes. Inhibition of CDK4 and CDK6 can prevent the inactivation of tumor suppressor protein Rb and interfere with tumor cell cycle progression.

At present, several selective CDK4/6 inhibitors are in the clinical stage (such as Palbociclib, Dinaciclib, LY2835219 and LEE011). Clinical evaluation of these drugs also includes metastatic breast cancer, ovarian cancer, liposarcoma, non-small cell lung cancer, liver cancer, glioblastoma, melanoma, multiple myeloma and lymphoma, etc.

Although many CDK inhibitor compounds have been disclosed, more CDK inhibitors (especially CDK4/6 selective inhibitors) are still needed to treat CDK related diseases.

SUMMARY OF THE INVENTION

The present disclosure provides 1H-[1,2,3] triazolo [4,5-h] quinazoline compounds as cyclin-dependent kinase inhibitors, which have strong inhibitory activity. In addition, the compounds of the present disclosure can further improve the pharmacokinetic properties, including metabolic stability and clearance, which will be significantly improved compared with the existing compounds.

In one aspect, the present disclosure provides a compound of formula (I), or a pharmaceutically acceptable salt, enantiomer, diastereomer, racemate, solvate, hydrate, polymorph, prodrug, or isotopic variant thereof, or a mixture thereof:

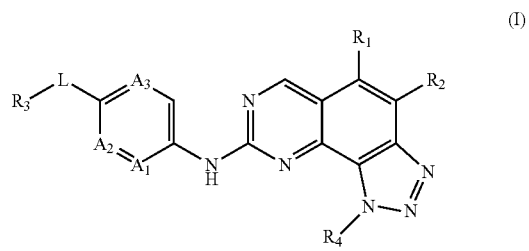

(I)

wherein:
$A_1$ is selected from $CR_5$ or N;
$A_2$ is selected from $CR_6$ or N;
$A_3$ is selected from $CR_7$ or N;
$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);
$R_4$ is selected from H, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;
and wherein,
$R_5$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
$R_6$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
$R_7$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
$R_8$ is selected from H, D, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;

$R_a$ is independently selected from H, —$C_{0-6}$ alkylene-CN, —$C_{0-6}$ alkylene-NO$_2$, —$C_{0-6}$ alkylene-OR', —$C_{0-6}$ alkylene-SR', —$C_{0-6}$ alkylene-NR"R''', —$C_{0-6}$ alkylene-C(O)R', —$C_{0-6}$ alkylene-C(O)OR', —$C_{0-6}$ alkylene-C(O)NR"R''', —$C_{0-6}$ alkylene-S(O)$_m$R', —$C_{0-6}$ alkylene-S(O)$_m$OR', —$C_{0-6}$ alkylene-S(O)$_m$NR"R''', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-NO$_2$, —$C_{0-6}$ alkylene-OR', —$C_{0-6}$ alkylene-SR', —$C_{0-6}$ alkylene-NR"R''', —$C_{0-6}$ alkylene-C(O)R', —$C_{0-6}$ alkylene-C(O)OR', —$C_{0-6}$ alkylene-C(O)NR"R''', —$C_{0-6}$ alkylene-S(O)$_m$R', —$C_{0-6}$ alkylene-S(O)$_m$OR', —$C_{0-6}$ alkylene-S(O)$_m$NR"R''', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R''' are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R''' are taken together with the nitrogen atoms to which they are attached to form 3- to 7-membered heterocyclyl;

m represents 0, 1 or 2; and, $R_1$—$R_2$ and $R_4$—$R_8$ are optionally substituted with 1, 2 or 3 R group(s), and R is independently selected from H, —OH, halogen, —NO$_2$, carbonyl, —CN, —OR$_a$, —SR$_a$, —NR$_b$R$_c$, —C(O)R$_a$, —C(S)R$_a$, —C(O)OR$_a$, —C(S)OR$_a$, —C(O)—NR$_b$R$_c$, —C(S)—NR$_b$R$_c$, —O—C(O)R$_a$, —O—C(S)R$_a$, —N(R$_b$)—C(O)—R$_a$, —N(R$_b$)—C(S)—R$_a$, —S(O)$_m$R$_a$, —S(O)$_m$OR$_a$, —S(O)$_m$NR$_b$R$_c$, —N(R$_b$)—S(O)$_m$—R$_a$, —N(R$_b$)—S(O)$_m$—NR$_b$R$_c$, —N(R$_b$)—C(O)OR$_a$, —N(R$_b$)—C(S)OR$_a$, —O—$C_{1-6}$ alkylene-OR$_a$, —C(O)—$C_{1-6}$ alkylene-NR$_b$R$_c$, —N(R$_b$)—C(O)—NR$_b$R$_c$, —N(R$_b$)—C(S)—NR$_b$R$_c$, —O—C(O)—NR$_b$R$_c$, —O—C(S)—NR$_b$R$_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl; wherein the $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is optionally further substituted with one or more of the following groups: —CN, —NO$_2$, carbonyl, —OR$_a$, —SR$_a$, —NR$_b$R$_c$, —C(O)R$_a$, —C(S)R$_a$, —C(O)OR$_a$, —C(S)OR$_a$, —C(O)—NR$_b$R$_c$, —C(S)—NR$_b$R$_c$, —O—C(O)R$_a$, —O—C(S)R$_a$, —N(R$_b$)—C(O)—R$_a$, —N(R$_b$)—C(S)—R$_a$, —S(O)$_m$R$_a$, —S(O)$_m$OR$_a$, —S(O)$_m$NR$_b$R$_c$, —N(R$_b$)—S(O)$_m$—R$_a$, —N(R$_b$)—S(O)$_m$—R$_b$R$_c$, —N(R$_b$)—C(O)OR$_a$, —N(R$_b$)—C(S)OR$_a$, —O—$C_{1-6}$ alkylene-OR$_a$, —C(O)—$C_{1-6}$ alkylene-NR$_b$R$_c$, —N(R$_b$)—C(O)—NR$_b$R$_c$, —N(R$_b$)—C(S)—NR$_b$R$_c$, —O—C(O)—NR$_b$R$_c$ or —O—C(S)—NR$_b$R$_c$;

$R_a$, $R_b$ and $R_c$ are optionally further substituted with one or more of the following groups:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In another aspect, the present disclosure provides a compound of formula (I), or a pharmaceutically acceptable salt, enantiomer, diastereomer, racemate, solvate, hydrate, polymorph, prodrug, or isotopic variant thereof, or a mixture thereof:

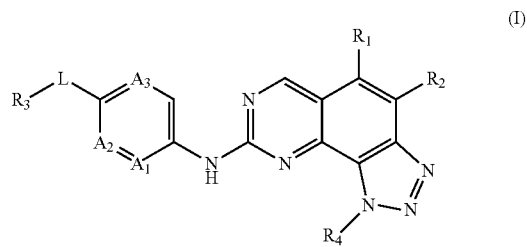

(I)

wherein:

$A_1$ is selected from CR$_5$ or N;

$A_2$ is selected from CR$_6$ or N;

$A_3$ is selected from CR$_7$ or N;

$R_1$ is selected from H, halogen, —CN, —OR$_a$, —SR$_a$, —NR$_b$R$_c$, —C(O)R$_a$, —C(O)OR$_a$, —C(O)NR$_b$R$_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_3$ is selected from H, halogen, —CN, —NO$_2$, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, —O—$C_{1-6}$ alkylene-R$_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);

$R_4$ is selected from H, —C(O)R$_a$, —C(O)OR$_a$, —C(O)NR$_b$R$_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, halogen, —CN, —OR$_a$, —SR$_a$, —NR$_b$R$_c$, —C(O)R$_a$, —C(O)OR$_a$, —C(O)NR$_b$R$_c$, $C_{1-6}$ alkyl or $C_{1-6}$ haloalkyl;

$R_6$ is selected from H, halogen, —CN, —OR$_a$, —SR$_a$, —NR$_b$R$_c$, —C(O)R$_a$, —C(O)OR$_a$, —C(O)NR$_b$R$_c$, $C_{1-6}$ alkyl or $C_{1-6}$ haloalkyl;

$R_7$ is selected from H, halogen, —CN, —OR$_a$, —SR$_a$, —NR$_b$R$_c$, —C(O)R$_a$, —C(O)OR$_a$, —C(O)NR$_b$R$_c$, $C_{1-6}$ alkyl or $C_{1-6}$ haloalkyl;

$R_8$ is selected from H, —NH$_2$, —NHC$_{1-6}$ alkyl, —N(C$_{1-6}$ alkyl)$_2$, $C_{1-6}$ alkyl, $C_{1-6}$ haloalkyl, —$C_{0-6}$ alkylene- $OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;

$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, $R_b$ and $R_c$ are taken together with the nitrogen atoms to which they are attached to form 3- to 7-membered heterocyclyl;

m represents 0, 1 or 2;

and, $R_1$—$R_2$ and $R_4$—$R_8$ are optionally substituted with 1, 2 or 3 R' group(s), wherein R' is independently selected from H, —OH, halogen, —$NO_2$, carbonyl, —CN, —$OR_a$, —$SR_a$, —$NR_bR_c$, —$C(O)R_a$, —$C(S)R_a$, —$C(O)OR_a$, —$C(S)OR_a$, —$C(O)$—$NR_bR_c$, —$C(S)$—$NR_bR_c$, —O—$C(O)R_a$, —O—$C(S)R_a$, —$N(R_b)$—$C(O)$—$R_a$, —$N(R_b)$—$C(S)$—$R_a$, —$S(O)_mR_a$, —$S(O)_mOR_a$, —$S(O)_mNR_bR_c$, —$N(R_b)$—$S(O)_m$—$R_a$, —$N(R_b)$—$S(O)_m$—$NR_bR_c$, —$N(R_b)$—$C(O)OR_a$, —$N(R_b)$—$C(S)OR_a$, —O—$C_{1-6}$ alkylene-$OR_a$, —$C(O)$—$C_{1-6}$ alkylene-$NR_bR_c$, —$N(R_b)$—$C(O)$—$NR_bR_c$, —$N(R_b)$—$C(S)$—$NR_bR_c$, —O—$C(O)$—$NR_bR_c$, —O—$C(S)$—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl; wherein the $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is optionally further substituted with one or more of the following groups:

—CN, —$NO_2$, carbonyl, —$OR_a$, —$SR_a$, —$NR_bR_c$, —$C(O)R_a$, —$C(S)R_a$, —$C(O)OR_a$, —$C(S)OR_a$, —$C(O)$—$NR_bR_c$, —$C(S)$—$NR_bR_c$, —O—$C(O)R_a$, —O—$C(S)R_a$, —$N(R_b)$—$C(O)$—$R_a$, —$N(R_b)$—$C(S)$—$R_a$, —$S(O)_mR_a$, —$S(O)_mOR_a$, —$S(O)_mNR_bR_c$, —$N(R_b)$—$S(O)_m$—$R_a$, —$N(R_b)$—$S(O)_m$—$R_bR_c$, —$N(R_b)$—$C(O)OR_a$, —$N(R_b)$—$C(S)OR_a$, —O—$C_{1-6}$ alkylene-$OR_a$, —$C(O)$—$C_{1-6}$ alkylene-$NR_bR_c$, —$N(R_b)$—$C(O)$—$NR_bR_c$, —$N(R_b)$—$C(S)$—$NR_bR_c$, —O—$C(O)$—$NR_bR_c$ or —O—$C(S)$—$NR_bR_c$;

$R_a$, $R_b$ and $R_c$ are optionally further substituted with one or more of the following groups:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In another aspect, the present disclosure provides a pharmaceutical composition comprising a compound disclosed herein, and optionally a pharmaceutically acceptable excipient(s).

In another aspect, the present disclosure provides a pharmaceutical composition comprising a compound disclosed herein and a pharmaceutically acceptable excipient(s), which further comprises other therapeutic agent(s).

In another aspect, the present disclosure provides a kit comprising a compound disclosed herein, other therapeutic agent(s), and a pharmaceutically acceptable carrier(s), adjuvant(s) or vehicle(s).

In another aspect, the present disclosure provides a use of a compound disclosed herein in the manufacture of a medicament for treating and/or preventing a disease mediated by CDK kinase.

In another aspect, the present disclosure provides a method of treating and/or preventing a disease mediated by CDK kinase in a subject, comprising administering to the subject a compound disclosed herein or a composition disclosed herein.

In another aspect, the present disclosure provides a compound disclosed herein or a composition disclosed herein, for use in treating and/or preventing a disease mediated by CDK kinase.

In a specific embodiment, the disease includes cell proliferative diseases, for example, solid tumor, such as sarcoma and cancer (such as fibrosarcoma, myxoid sarcoma, liposarcoma, chondrosarcoma, osteogenic sarcoma, chordoma, angiosarcoma, endotheliosarcoma, lymphangiosarcoma, lymphangioendotheliosarcoma, synovial tumor, mesothelioma, ewing's tumor, leiomyosarcoma, rhabdomyosarcoma, colon cancer, pancreatic adenocarcinoma, breast cancer, ovarian cancer, prostate cancer, squamous cell carcinoma, basal cell carcinoma, adenocarcinoma, sweat gland tumor, sebaceous gland carcinoma, papillary carcinoma, papillary adenocarcinoma, cystadenocarcinoma, medullary carcinoma, bronchopulmonary carcinoma, renal cell carcinoma, hepatocellular carcinoma, cholangiocarcinoma, choriocarcinoma, seminoma, embryonal carcinoma, embryonal carcinosarcoma, cervical cancer, uterine cancer, testicular cancer, lung cancer, small cell lung cancer, bladder cancer, upper cutaneous carcinoma, glioma, astrocytoma, medulloblastoma, craniopharyngioma, ependymoma, pineal tumor, hemangioblastoma, acoustic neuroma, oligodendroglioma, schwannoma, meningioma, melanoma, neuroblastoma and retinoblastoma).

Other objects and advantages of the present disclosure will be apparent to those skilled in the art from the specific embodiments, examples and claims disclosed herein.

Definition

Chemical Definitions

Definitions of specific functional groups and chemical terms are described in more detail below.

When a range of values is listed, it is intended to encompass each value and sub-range within the range. For example "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_{1-6}$ alkyl" refers to a radical of a straight or branched, saturated hydrocarbon group having 1 to 6 carbon atoms. In some embodiments, $C_{1-4}$ alkyl is preferred. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$) or i-Bu (—CH$_2$CH(CH$_3$)$_2$).

"C$_{2-6}$ alkenyl" refers to a radical of a straight or branched hydrocarbon group having 2 to 6 carbon atoms and at least one carbon-carbon double bond. In some embodiments, C$_{2-4}$ alkenyl is preferred. Examples of C$_{2-6}$ alkenyl include vinyl (C$_2$), 1-propenyl (C$_3$), 2-propenyl (C$_3$), 1-butenyl (C$_4$), 2-butenyl (C$_4$), butadienyl (C$_4$), pentenyl (C$_5$), pentadienyl (C$_5$), hexenyl (C$_6$), etc. The term "C$_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"C$_{2-6}$ alkynyl" refers to a radical of a straight or branched hydrocarbon group having 2 to 6 carbon atoms, at least one carbon-carbon triple bond, and optionally one or more carbon-carbon double bonds. In some embodiments, C$_{2-4}$ alkynyl is preferred. Examples of C$_{2-6}$ alkynyl include, but are not limited to, ethynyl (C$_2$), 1-propynyl (C$_3$), 2-propynyl (C$_3$), 1-butynyl (C$_4$), 2-butynyl (C$_4$), pentynyl (C$_5$), hexynyl (C$_6$), etc. The term "C$_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"—C$_{1-6}$ alkylene-, —C$_{2-6}$ alkenylene- or —C$_{2-6}$ alkynylene-" refers to a divalent group of the "C$_{1-6}$ alkyl, C$_{2-6}$ alkenyl or C$_{2-6}$ alkynyl" as defined above.

"C$_{1-6}$ alkylene" refers to a divalent group formed by removing another hydrogen of the C$_{1-6}$ alkyl, and can be a substituted or unsubstituted alkylene. In some embodiments, C$_{1-4}$ alkylene is particularly preferred. The unsubstituted alkylene groups include, but are not limited to, methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), etc. Examples of substituted alkylene groups, such as those substituted with one or more alkyl (methyl) groups, include, but are not limited to, substituted methylene (—CH(CH$_3$)—, —C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), etc.

"C$_{0-6}$ alkylene" means a chemical bond, and "C$_{1-6}$ alkylene" as defined above.

"C$_{2-6}$ alkenylene" refers to a divalent group formed by removing another hydrogen of the C$_{2-6}$ alkenyl, and can be substituted or unsubstituted alkenylene. In some embodiments, C$_{2-4}$ alkenylene is particularly preferred. Exemplary unsubstituted alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethenylene (—C(CH$_3$)=CH—, —CH=C(CH$_3$)—), substituted propenylene (e.g., —C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"C$_{2-6}$ alkynylene" refers to a divalent group formed by removing another hydrogen of the C$_{2-6}$ alkynyl, and can be substituted or unsubstituted alkynylene. In some embodiments, C$_{2-4}$ alkynylene is particularly preferred. Exemplary alkynylene groups include, but are not limited to, ethynylene (—C≡C—), substituted or unsubstituted propynylene (—C≡CCH$_2$—), and the like.

"Halo" or "halogen" refers to fluorine (F), chlorine (C$_1$), bromine (Br) and iodine (I).

"C$_{1-6}$ haloalkyl" means the above "C$_{1-6}$ alkyl" which is substituted with one or more halogen groups. Examples include mono-, di-, and poly-halogenated, including perhalogenated, alkyl. A monohalogen substituent in the group may be an iodine, bromine, chlorine or fluorine atom; dihalogen substituents and polyhalogen substituents may be two or more identical halogen atoms or a combination of different halogens. Examples of preferred haloalkyl groups include monofluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The haloalkyl group can be substituted at any available point of attachment, for example, with 1 to 5 substituents, 1 to 3 substituents or 1 substituent.

"C$_{3-7}$ cycloalkyl" refers to a radical of a non-aromatic cyclic hydrocarbon group having from 3 to 7 ring carbon atoms and zero heteroatom. In some embodiments, C$_{3-6}$ cycloalkyl is especially preferred, C$_{4-6}$ cycloalkyl is more preferred, and C$_{5-6}$ cycloalkyl is even more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continues to designate the number of carbons in the cycloalkyl ring system. Exemplary cycloalkyl groups include, but is not limited to, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), cycloheptyl (C$_7$), cycloheptenyl (C$_7$), cycloheptadienyl (C$_7$), cycloheptatrienyl (C$_7$), and the like.

"3- to 11-membered heterocyclyl" refers to a radical of a 3- to 11-membered non-aromatic ring system having ring carbon atoms and 1 to 5 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as long as valency permits. In some embodiments, 3- to 9-membered heterocyclyl is preferred, which is a radical of a 3- to 9-membered non-aromatic ring system having ring carbon atoms and 1 to 5 ring heteroatoms; in some embodiments, 3- to 7-membered heterocyclyl is preferred, which is a radical of a 3- to 7-membered non-aromatic ring system having ring carbon atoms and 1 to 4 ring heteroatoms; 3- to 6-membered heterocyclyl is preferred, which is a radical of a 3- to 6-membered non-aromatic ring system having ring carbon atoms and 1 to 3 ring heteroatoms; 4- to 7-membered heterocyclyl is preferred, which is a radical of a 4- to 7-membered non-aromatic ring system having ring carbon atoms and 1 to 3 ring heteroatoms; 4- to 6-membered heterocyclyl is preferred, which is a radical of a 4- to 6-membered non-aromatic ring system having ring carbon atoms and 1 to 3 ring heteroatoms; 5- to 6-membered heterocyclyl is more preferred, which is a radical of a 5- to 6-membered non-aromatic ring system having ring carbon atoms and 1 to 3 ring heteroatoms. Heterocyclyl also includes ring systems wherein the heterocyclyl ring, as defined above, is fused with one or more cycloalkyl groups, and the point of attachment is on the cycloalkyl ring; or wherein the heterocyclyl ring, as defined above, is fused with one or more aryl or heteroaryl groups, and the point of attachment is on the heterocyclyl ring; and in such instances, the number of ring members continues to designate the number of ring members in the heterocyclyl ring system. Exemplary 3-membered heterocyclyl groups containing one heteroatom include, but are not limited to, azirdinyl, oxiranyl, and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidinyl, tetrahydropyranyl, dihydropyridinyl, and thianyl. Exemplary 6-membered heterocyclyl groups containing two heteroatoms include, but are not limited to, piperazinyl, morpholinyl, dithianyl, and dioxanyl. Exemplary 6-membered heterocyclyl groups containing three heteroatoms include, but are not limited to, triazinanyl. Exemplary 7-membered heterocyclyl groups containing one heteroatom include, but are not limited to, azepanyl, oxepanyl and thiepanyl. Exemplary 5-membered heterocyclyl groups fused to a $C_6$ aryl ring (also referred to herein as a 5,6-bicyclic heterocyclic ring) include, but are not limited to, indolinyl, isoindolinyl, dihydrobenzofuranyl, dihydrobenzothienyl, benzoxazolinonyl, and the like. Exemplary 6-membered heterocyclyl groups fused to a $C_6$ aryl ring (also referred to herein as a 6,6-bicyclic heterocyclic ring) include, but are not limited to, tetrahydroquinolinyl, tetrahydroisoquinolinyl, and the like.

The 3- to 11-membered heterocyclyl also includes a spiroheterocyclic group, that is, a group in which two rings (e.g., a heterocyclyl and a carbocyclyl) share one carbon atom, wherein at least one ring is a heterocyclyl as defined above. More specifically, the spiroheterocyclyl is a spiro ring formed by two 4-membered rings, two 5-membered rings, two 6-membered rings, one 4-membered ring and one 5-membered ring, one 4-membered ring and one 6-membered ring, or one 5-membered ring and one 6-membered ring, wherein at least one ring is a 4- to 6-membered heterocyclyl as defined above, a 4- to 6-membered heterocyclyl containing 1, 2 or 3 O, N or S heteroatoms is preferred, and a 4- to 6-membered heterocyclyl containing 1 N heteroatom is more preferred. Specific spiroheterocyclyl groups include, but are not limited to:

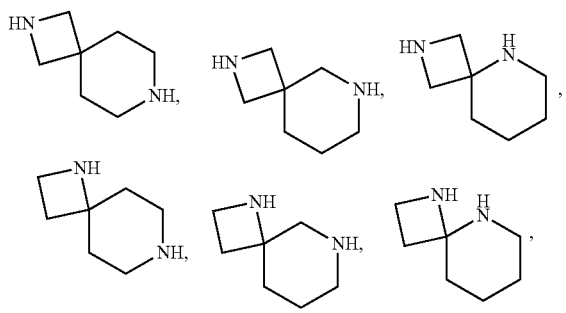

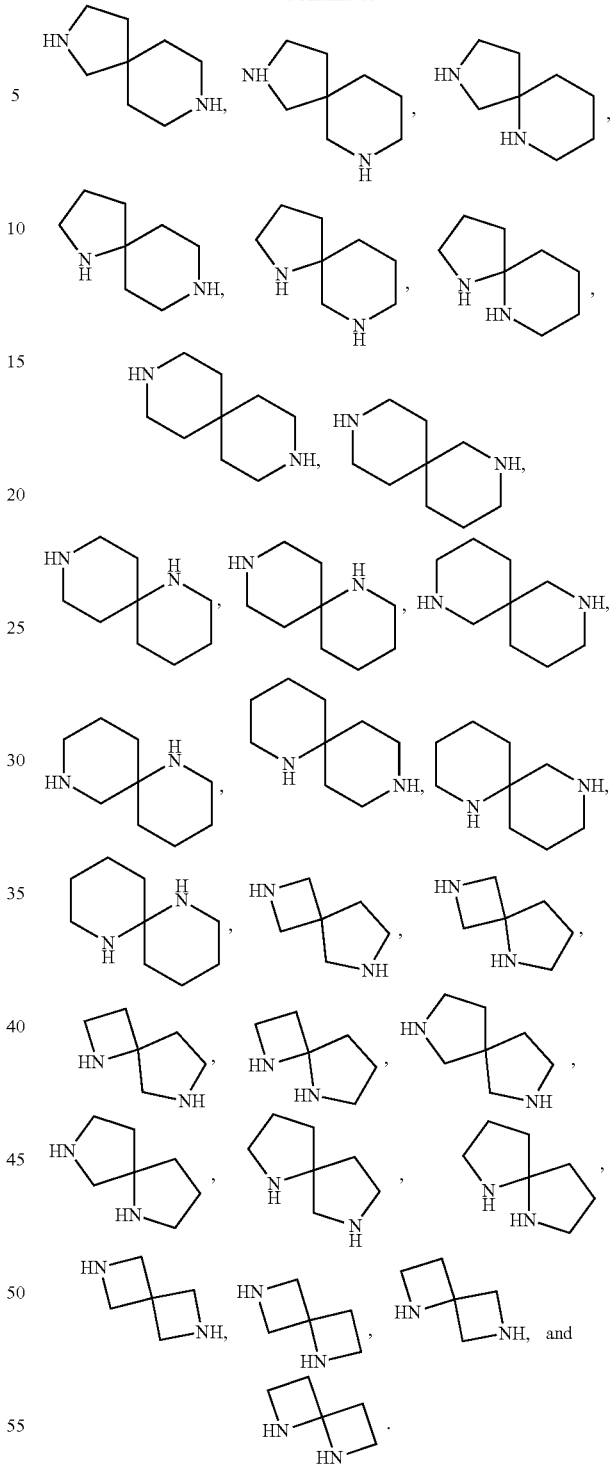

"$C_{6-10}$ aryl" refers to a radical of a monocyclic or polycyclic (e.g., bicyclic) 4n+2 aromatic ring system (e.g, having 6 or 10 π electrons shared in a cyclic array) having 6-10 ring carbon atoms and zero heteroatom. In some embodiments, an aryl group has six ring carbon atoms ("$C_6$ aryl"; e.g., phenyl). In some embodiments, an aryl group has ten ring carbon atoms ("$C_{10}$ aryl"; e.g, naphthyl such as 1-naphthyl and 2-naphthyl). Aryl also includes ring systems wherein the aryl ring, as defined above, is fused with one or more cycloalkyl, or heterocyclyl groups and the point of attachment is on the aryl ring, and in such instances, the number of carbon atoms continues to designate the number of carbon atoms in the aryl ring system.

"5- to 10-membered heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as long as valency permits. Heteroaryl bicyclic ring systems can include one or more heteroatoms in one or both rings. Heteroaryl further includes ring systems wherein the heteroaryl ring, as defined above, is fused with one or more cycloalkyl, or heterocyclyl groups and the point of attachment is on the heteroaryl ring, and in such instances, the number of ring members continues to designate the number of ring members in the heteroaryl ring system. In some embodiments, 5- to 6-membered heteroaryl is especially preferred, which is a radical of a 5-6 membered monocyclic or bicyclic 4n+2 aromatic ring system having ring carbon atoms and 1-4 ring heteroatoms. Exemplary 5-membered heteroaryl groups containing one heteroatom include, but are not limited to, pyrrolyl, furanyl and thiophenyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (e.g., 1,2,4-oxadiazolyl), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridinyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, but are not limited to, naphthyridinyl, pteridinyl, quinolinyl, isoquinolinyl, cinnolinyl, quinoxalinyl, phthalazinyl, and quinazolinyl.

"Carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents on a carbon atom include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$_a$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$_a$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$_a$)$_2$, —B(OR$^{cc}$)$_2$, —BR$^{aa}$(OR$^{cc}$), alkyl, haloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from alkyl, haloalkyl, alkenyl, alkynyl, carbocyclyl, heterocyclyl, aryl, and heteroaryl, or two R$^{aa}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$_c$)$_2$, —CO$_2$R$_a$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl, and heteroaryl, or two R$^{bb}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, alkyl, haloalkyl, alkenyl, alkynyl, carbocyclyl, heterocyclyl, aryl, and heteroaryl, or two R$^{cc}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from alkyl, haloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, alkyl, haloalkyl, alkenyl, alkynyl, carbocyclyl, heterocyclyl, aryl and heteroaryl, or two $R^{ff}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal $R^{gg}$ substituents can be joined to form =O or =S; wherein X$^-$ is a counterion.

Exemplary substituents on a nitrogen atom include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$_c$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl, and heteroaryl, or two $R^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Other Definitions

As used herein, "cancer" refers to any disease that is caused by or results in inappropriately high levels of cell division, inappropriately low levels of apoptosis, or both. Examples of cancer include, but are not limited to, leukemias (e.g., acute leukemia, acute lymphocytic leukemia, acute myelocytic leukemia, acute myeloblasts leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors.

The term "treating/treatment" as used herein relates to reversing, alleviating, inhibiting the progression or prophylaxis of a disorder or condition to which the term applies, or one or more symptoms of such disorder or condition. The noun "treating/treatment" as used herein relates to the action of treat, which is a verb, and the latter is as just defined The term "pharmaceutically acceptable" as used herein denotes within the scope of sound medical judgment, the substances are suitable for use in contact with the patient's tissue without undue toxicity, irritation, allergic response and the like, and are commensurate with a reasonable benefit/risk ratio, and are effective for their intended use, including, if possible, the zwitterionic form of the compounds disclosed herein.

The term "salt" denotes relatively non-toxic, inorganic and organic acid addition salts of the compounds disclosed herein. These salts can be prepared in situ during the final isolation and purification of the compound, or by isolating salts produced by separately reacting the purified compound in the free base form with a suitable organic or inorganic acid.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19, which is incorporated herein by reference).

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "humam", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, the term "compound disclosed herein" refers to the following compounds of formulae (I), or a pharmaceutically acceptable salt, enantiomer, diastereomer, racemate, solvate, hydrate, polymorph, prodrug, or isotopic variant thereof, or a mixture thereof.

In the present disclosure, compounds are named generally described herein using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E. Compounds which exist in different tautomeric forms, one of which is not limited to any particular tautomer, but is intended to cover all tautomeric forms.

In one embodiment, the present disclosure refers to a compound of formula (I), or a pharmaceutically acceptable salt, enantiomer, diastereomer, racemate, solvate, hydrate, polymorph, prodrug, or isotopic variant thereof, or a mixture thereof:

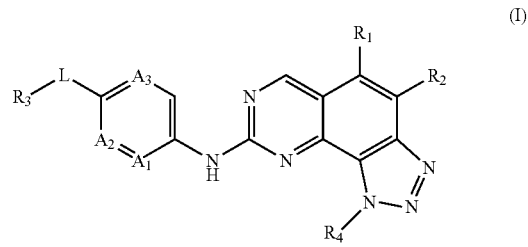

(I)

wherein:
$A_1$ is selected from $CR_5$ or N;
$A_2$ is selected from $CR_6$ or N;
$A_3$ is selected from $CR_7$ or N;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);

$R_4$ is selected from H, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

wherein, $R_5$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_8$ is selected from H, D, —$NH_2$, —NH$C_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R'" are taken together with the nitrogen atoms to which they are attached to form 3- to 7-membered heterocyclyl;

m represents 0, 1 or 2;

and, $R_1$—$R_2$ and $R_4$—$R_8$ are optionally substituted with 1, 2 or 3 R group(s), wherein R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl; wherein the $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is optionally further substituted with one or more of the following groups:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, or —O—C(S)—$NR_bR_c$;

$R_a$, $R_b$ and $R_c$ are optionally further substituted with one or more of the following groups:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In another embodiment, the present disclosure refers to a compound of formula (I), or a pharmaceutically acceptable salt, enantiomer, diastereomer, racemate, solvate, hydrate, polymorph, prodrug, or isotopic variant thereof, or a mixture thereof:

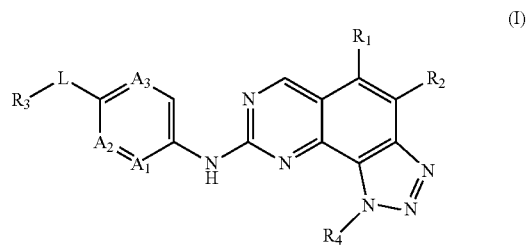

(I)

wherein:

$A_1$ is selected from $CR_5$ or N;
$A_2$ is selected from $CR_6$ or N;
$A_3$ is selected from $CR_7$ or N;
$R_1$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_3$ is selected from H, halogen, —CN, —$NO_2$, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);
$R_4$ is selected from H, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;
wherein,
$R_5$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;
$R_6$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;
$R_7$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;
$R_8$ is selected from H, —$NH_2$, —NH$C_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;
$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;
$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, $R_b$ and $R_c$ are taken together with the nitrogen atoms to which they are attached to form 3- to 7-membered heterocyclyl;
m represents 0, 1 or 2;
and,
$R_1$—$R_2$ and $R_4$—$R_8$ are optionally substituted with 1, 2 or 3 R' group(s), wherein R' is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl; wherein the $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is optionally further substituted with one or more of the following groups:
—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$ or —O—C(S)—$NR_bR_c$;

$R_a$, $R_b$ and $R_c$ are optionally further substituted with one or more of the following groups:
$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

$A_1$, $A_2$ and $A_3$

In a specific embodiment, $A_1$ is $CR_5$; in another specific embodiment, $A_1$ is CH; in another specific embodiment, $A_1$ is C(OMe); in another specific embodiment, $A_1$ is CF; in another specific embodiment, $A_1$ is N.

In a specific embodiment, $A_2$ is $CR_6$; in another specific embodiment, $A_2$ is CH; in another specific embodiment, $A_2$ is CF; in another specific embodiment, $A_2$ is CMe; in another specific embodiment, $A_2$ is N.

In a specific embodiment, $A_3$ is $CR_7$; in another specific embodiment, $A_3$ is CH; in another specific embodiment, $A_3$ is CMe; in another specific embodiment, $A_3$ is CF; in another specific embodiment, $A_3$ is N.

$R_1$

In a specific embodiment, $R_1$ is H; in another specific embodiment, $R_1$ is D; in another specific embodiment, $R_1$ is halogen; in another specific embodiment, $R_1$ is —CN; in another specific embodiment, $R_1$ is —$OR_a$; in another specific embodiment, $R_1$ is —$SR_a$; in another specific embodiment, $R_1$ is —$NR_bR_c$; in another specific embodiment, $R_1$ is —C(O)$R_a$; in another specific embodiment, $R_1$ is —C(O)$OR_a$; in another specific embodiment, $R_1$ is —C(O)$NR_bR_c$; in another specific embodiment, $R_1$ is $C_{1-6}$ alkyl; in another specific embodiment, $R_1$ is Me; in another specific embodiment, $R_1$ is $C_{1-6}$ haloalkyl; in another specific embodiment, $R_1$ is $C_{3-7}$ cycloalkyl; in another specific embodiment, $R_1$ is 3- to 7-membered heterocyclyl; in another specific embodiment, $R_1$ is $C_{6-10}$ aryl; in another specific embodiment, $R_1$ is 5- to 10-membered heteroaryl.

In the above specific embodiments of $R_1$, the $C_{3-7}$ cycloalkyl or 3- to 7-membered heterocyclyl is optionally substituted with oxo; in the above specific embodiments of $R_1$, the $C_{3-7}$ cycloalkyl or 3- to 7-membered heterocyclyl is optionally substituted with thioxo.

$R_2$

In a specific embodiment, $R_2$ is H; in another specific embodiment, $R_2$ is D; in another specific embodiment, $R_2$ is halogen; in another specific embodiment, $R_2$ is —CN; in another specific embodiment, $R_2$ is $C_{1-6}$ alkyl; in another specific embodiment, $R_2$ is $C_{1-6}$ haloalkyl; in another specific embodiment, $R_2$ is $C_{3-7}$ cycloalkyl; in another specific embodiment, R₂ is 3- to 7-membered heterocyclyl; in another specific embodiment, R₂ is $C_{6-10}$ aryl; in another specific embodiment, R₂ is 5- to 10-membered heteroaryl.

In the above specific embodiment of R₂, the $C_{3-7}$ cycloalkyl or 3- to 7-membered heterocyclyl is optionally substituted with oxo; In the above specific embodiment of R₂, the $C_{3-7}$ cycloalkyl or 3- to 7-membered heterocyclyl is optionally substituted with thioxo.

R₃

In a specific embodiment, R₃ is H; in another specific embodiment, R₃ is D; in another specific embodiment, R₃ is halogen; in another specific embodiment, R₃ is —CN; in another specific embodiment, R₃ is —NO₂; in another specific embodiment, R₃ is —OR$_a$; in another specific embodiment, R₃ is —SR$_a$; in another specific embodiment, R₃ is —NR$_b$R$_c$; in another specific embodiment, R₃ is —C(O)R$_a$; in another specific embodiment, R₃ is —C(O)OR$_a$; in another specific embodiment, R₃ is —C(O)NR$_b$R$_c$; in another specific embodiment, R₃ is —S(O)$_m$R$_a$; in another specific embodiment, R₃ is —S(O)$_m$OR$_a$; in another specific embodiment, R₃ is —S(O)$_m$NR$_b$R$_c$; in another specific embodiment, R₃ is —O—$C_{1-6}$ alkylene-R₈; in another specific embodiment, R₃ is $C_{1-6}$ alkyl; in another specific embodiment, R₃ is $C_{1-6}$ haloalkyl; in another specific embodiment, R₃ is $C_{3-7}$ cycloalkyl; in another specific embodiment, R₃ is 3- to 11-membered heterocyclyl; in another specific embodiment, R₃ is 4- to 7-membered heterocyclyl; in another specific embodiment, R₃ is 5- to 6-membered heterocyclyl; in another specific embodiment, R₃ is piperazinyl; in another specific embodiment, R₃ is 3- to 9-membered heterocyclyl; in another specific embodiment, R₃ is $C_{6-10}$ aryl; in another specific embodiment, R₃ is 5- to 10-membered heteroaryl.

In the above specific embodiment of R₃, each of which is optionally substituted with 1, 2, 3, 4 or 5 R₈ group(s). In a specific embodiment, each of which is optionally substituted with one R₈ group; in another specific embodiment, each of which is optionally substituted with 2 R₈ groups; in another specific embodiment, each of which is optionally substituted with 3 R₈ groups; in another specific embodiment, each of which is optionally substituted with 4 R₈ groups; in another specific embodiment, each of which is optionally substituted with 5 R₈ groups.

In a more specific embodiment, R₃ is selected from the following groups, each of which is optionally substituted with 1, 2, 3, 4 or 5 R₈ group(s):

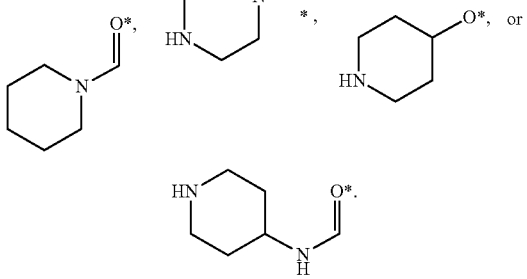

wherein * represents the point of attachment.

In a more specific embodiment, R₃ is selected from the following groups:

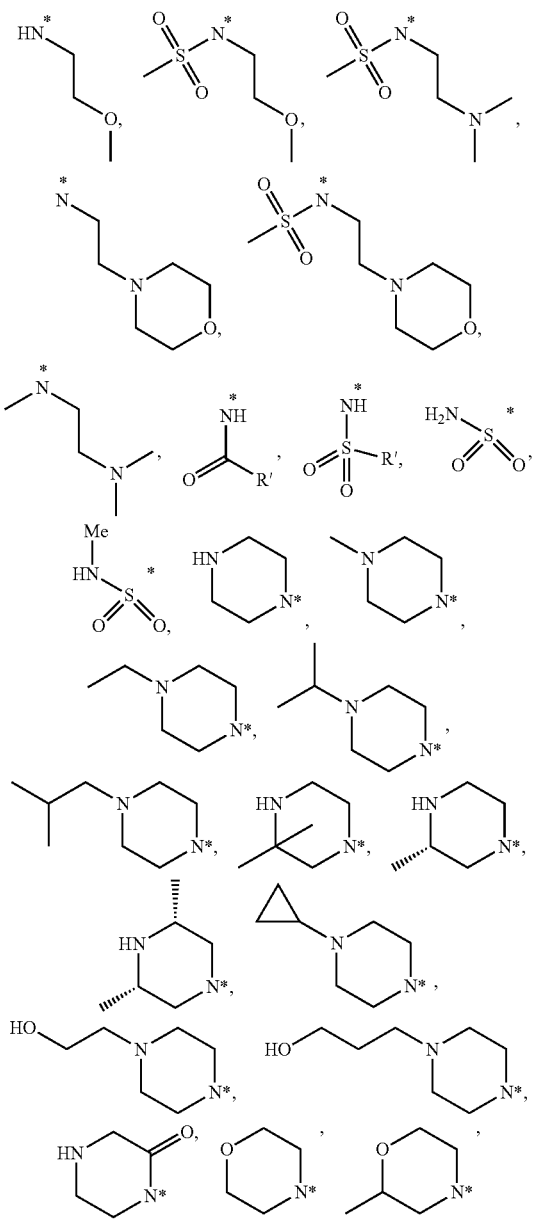

23

-continued

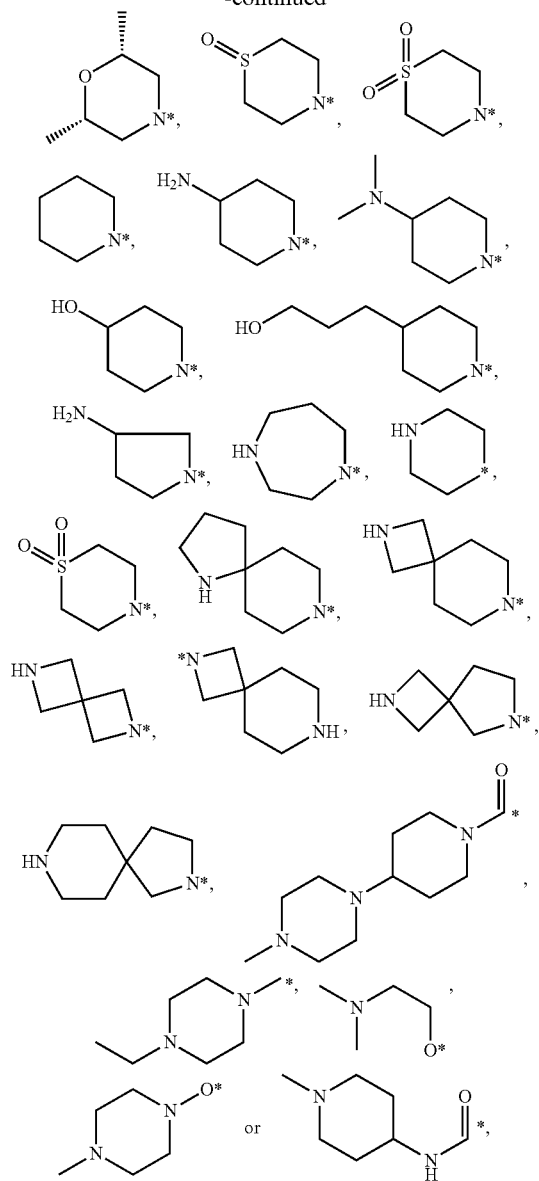

wherein * represents the point of attachment.

In a more specific embodiment, $R_3$ is selected from the following groups:

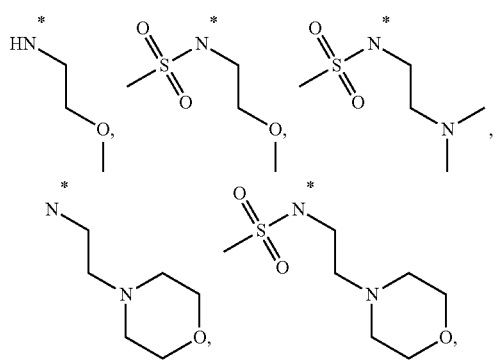

24

-continued

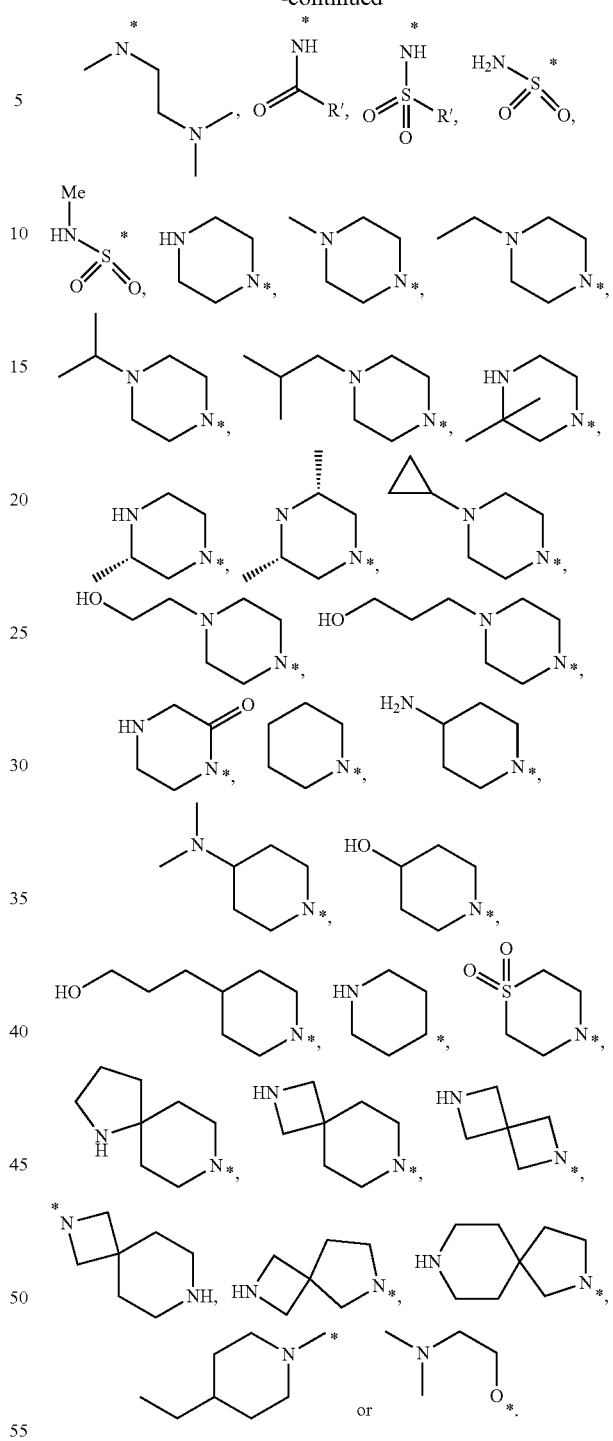

$R_4$

In a specific embodiment, $R_4$ is H; in another specific embodiment, $R_4$ is —C(O)$R_a$; in another specific embodiment, $R_4$ is —C(O)O$R_a$; in another specific embodiment, $R_4$ is —C(O)N$R_b R_c$; in another specific embodiment, $R_4$ is $C_{1-6}$ alkyl; in another specific embodiment, $R_4$ is $C_{1-6}$ haloalkyl; in another specific embodiment, $R_4$ is $C_{3-7}$ cycloalkyl; in another specific embodiment, $R_4$ is 3- to 7-membered heterocyclyl; in another specific embodiment, $R_4$ is $C_{6-10}$ aryl; in another specific embodiment, $R_4$ is 5- to 10-membered heteroaryl; in another specific embodiment, R₄ is isopropyl, isobutyl or cyclopentyl.

L

In a specific embodiment, L is bond; in another specific embodiment, L is —O—; in another specific embodiment, L is —NH—; in another specific embodiment, L is —C(O)—; in another specific embodiment, L is —C(O)NH—; in another specific embodiment, L is —NHC(O)—; in another specific embodiment, L is —C₁₋₆ alkylene-; in another specific embodiment, L is —C₂₋₆ alkenylene-; in another specific embodiment, L is —C₂₋₆ alkynylene-.

R₅

In a specific embodiment, R₅ is H; in a specific embodiment, R₅ is D; in a specific embodiment, R₅ is halogen; in a specific embodiment, R₅ is —CN; in a specific embodiment, R₅ is —OR$_a$; in a specific embodiment, R₅ is —SR$_a$; in a specific embodiment, R₅ is —NR$_b$R$_c$; in a specific embodiment, R₅ is —C(O)R$_a$; in a specific embodiment, R₅ is —C(O)OR$_a$; in a specific embodiment, R₅ is —C(O)NR$_b$R$_c$; in a specific embodiment, R₅ is —S(O)$_m$R$_a$; in a specific embodiment, R₅ is —S(O)$_m$OR$_a$; in a specific embodiment, R₅ is —S(O)$_m$NR$_b$R$_c$; in another specific embodiment, R₅ is C₁₋₆ alkyl; in another specific embodiment, R₅ is C₁₋₆ haloalkyl.

R₆

In a specific embodiment, R₆ is H; in a specific embodiment, R₆ is D; in a specific embodiment, R₆ is halogen; in a specific embodiment, R₆ is —CN; in a specific embodiment, R₆ is —OR$_a$; in a specific embodiment, R₆ is —SR$_a$; in a specific embodiment, R₆ is —NR$_b$R$_c$; in a specific embodiment, R₆ is —C(O)R$_a$; in a specific embodiment, R₆ is —C(O)OR$_a$; in a specific embodiment, R₆ is —C(O)NR$_b$R$_c$; in a specific embodiment, R₆ is —S(O)$_m$R$_a$; in a specific embodiment, R₆ is —S(O)$_m$OR$_a$; in a specific embodiment, R₆ is —S(O)$_m$NR$_b$R$_c$; in another specific embodiment, R₆ is C₁₋₆ alkyl; in another specific embodiment, R₆ is C₁₋₆ haloalkyl.

R₇

In a specific embodiment, R₇ is H; in a specific embodiment, R₇ is D; in a specific embodiment, R₇ is halogen; in a specific embodiment, R₇ is F; in a specific embodiment, R₇ is —CN; in a specific embodiment, R₇ is —OR$_a$; in a specific embodiment, R₇ is —SR$_a$; in a specific embodiment, R₇ is —NR$_b$R$_c$; in a specific embodiment, R is —C(O)R$_a$; in a specific embodiment, R₇ is —C(O)OR$_a$; in a specific embodiment, R₇ is —C(O)NR$_b$R$_c$; in a specific embodiment, R₇ is —S(O)$_m$R$_a$; in a specific embodiment, R is —S(O)$_m$OR$_a$; in a specific embodiment, R₇ is —S(O)$_m$NR$_b$R$_c$; in another specific embodiment, R is C₁₋₆ alkyl; in another specific embodiment, R₇ is C₁₋₆ haloalkyl.

R₈

In a specific embodiment, R₈ is H; in a specific embodiment, R₈ is D; in another specific embodiment, R₈ is —NH₂; in another specific embodiment, R₈ is —NHC₁₋₆ alkyl; in another specific embodiment, R₈ is —N(C₁₋₆ alkyl)₂; in another specific embodiment, R₈ is C₁₋₆ alkyl; in another specific embodiment, R₈ is C₁₋₆ haloalkyl; in another specific embodiment, R₈ is —C₀₋₆ alkylene-OR$_a$; in another specific embodiment, R₈ is C₃₋₇ cycloalkyl; in another specific embodiment, R₈ is 3- to 7-membered heterocyclyl; in another specific embodiment, R₈ is C₆₋₁₀ aryl; in another specific embodiment, R₈ is 5- to 10-membered heteroaryl; in another specific embodiment, two R₈ groups on the same carbon atom are taken together to form oxo. in another specific embodiment, two R₈ groups on the same carbon atom are taken together to form thioxo.

m

In a specific embodiment, m is 0; in another specific embodiment, m is 1; in another specific embodiment, m is 2.

Any technical solution in any one of the above specific embodiments, or any combination thereof, may be combined with any technical solution in other specific embodiments or any combination thereof. For example, any technical solution of A₁ or any combination thereof may be combined with any technical solution of A₂, A₃, R₁—R⁸, R', R$_a$, R$_b$, R$_c$, L, m or any combination thereof. The present disclosure is intended to include all combination of such technical solutions, which are not exhaustively listed here to save space.

In a specific embodiment, the present disclosure provides compounds of the following formula:

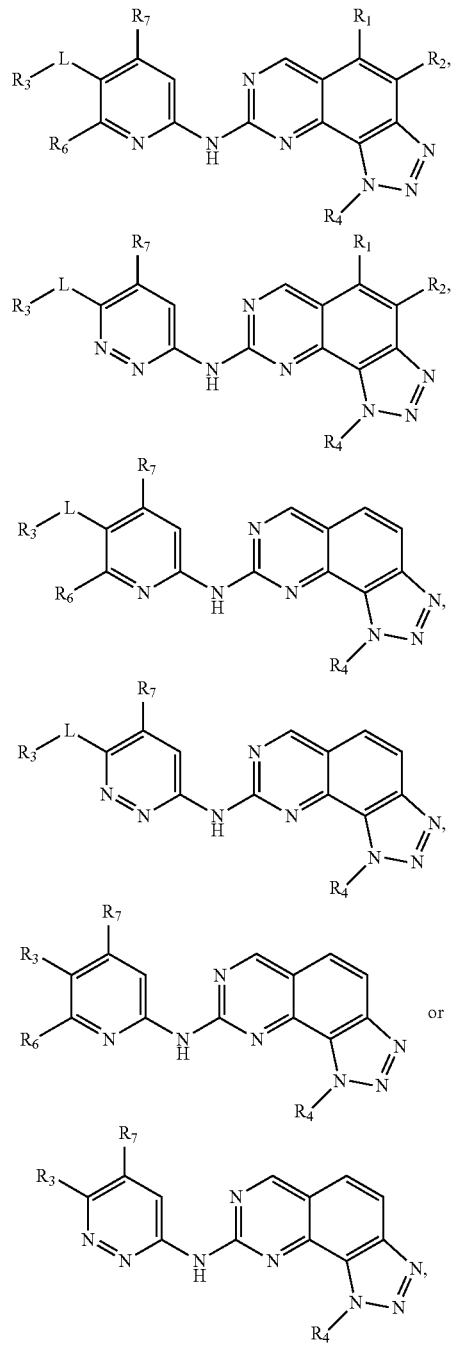

wherein each group is as defined in the context.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is N.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is $CR_5$.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_2$ is $CR_6$.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_3$ is $CR_7$.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $R_1$ is selected from H, D, halogen, —CN, $C_{1-6}$ alkyl or $C_{1-6}$ haloalkyl; alternatively, $R_1$ is H or D.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $R_2$ is selected from H, D, halogen, —CN, $C_{1-6}$ alkyl or $C_{1-6}$ haloalkyl; alternatively, $R_2$ is H or D.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein,
  $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R^8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);
  alternatively, $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl, $C_{1-6}$ haloalkyl, $C_{3-7}$ cycloalkyl or 4- to 7-membered heterocyclyl, each of which is optionally substituted with 1, 2 or 3 $R_8$ group(s);
  alternatively, $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{3-7}$ cycloalkyl or 4- to 7-membered heterocyclyl, each of which is optionally substituted with 1 or 2 $R_8$ group(s);
  alternatively, $R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{4-6}$ cycloalkyl or 5- to 6-membered heterocyclyl (e.g. piperazinyl), each of which is optionally substituted with one $R_8$ group;
  alternatively, $R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$ or —$S(O)_mNR_bR_c$, or the following groups optionally substituted with 1, 2, 3, 4 or 5 $R_8$ group(s):

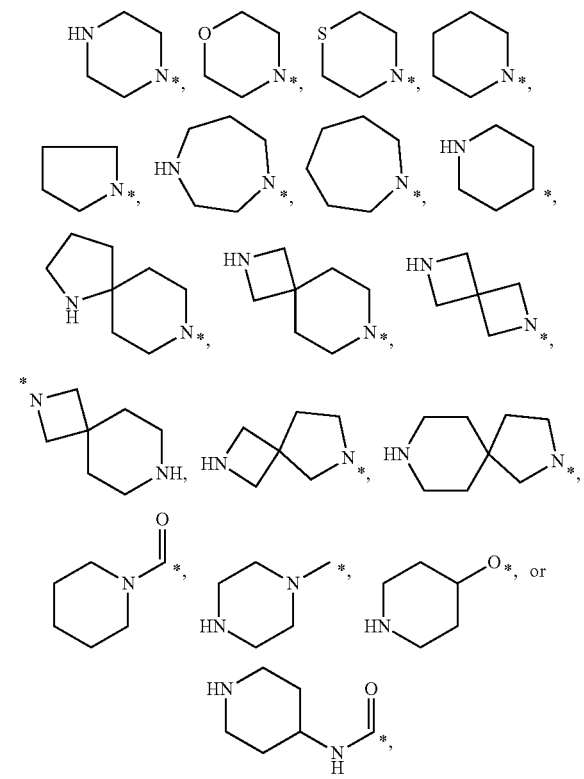

wherein * represents the point of attachment;
alternatively, $R_3$ is selected from the following groups:

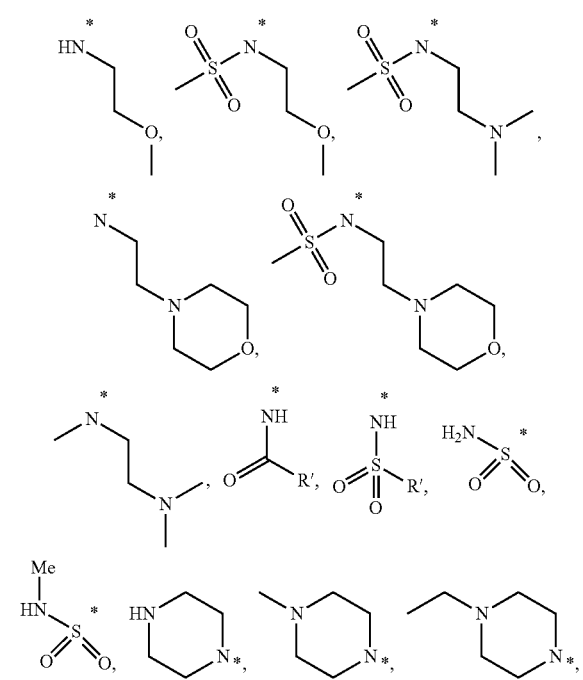

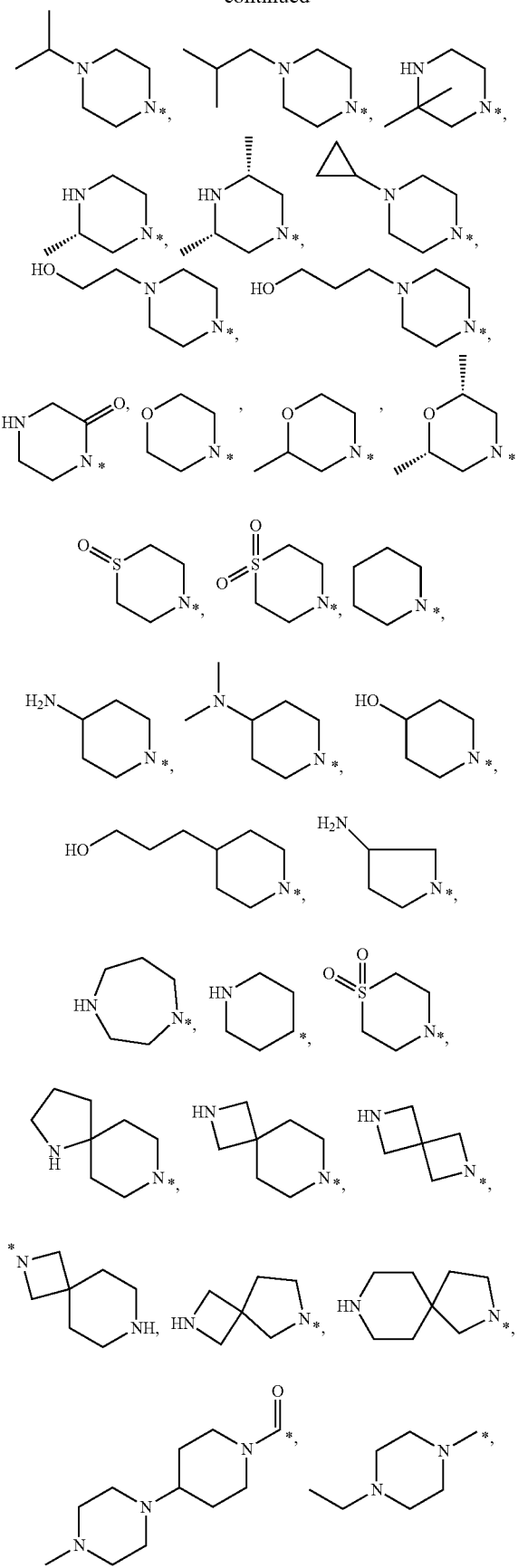
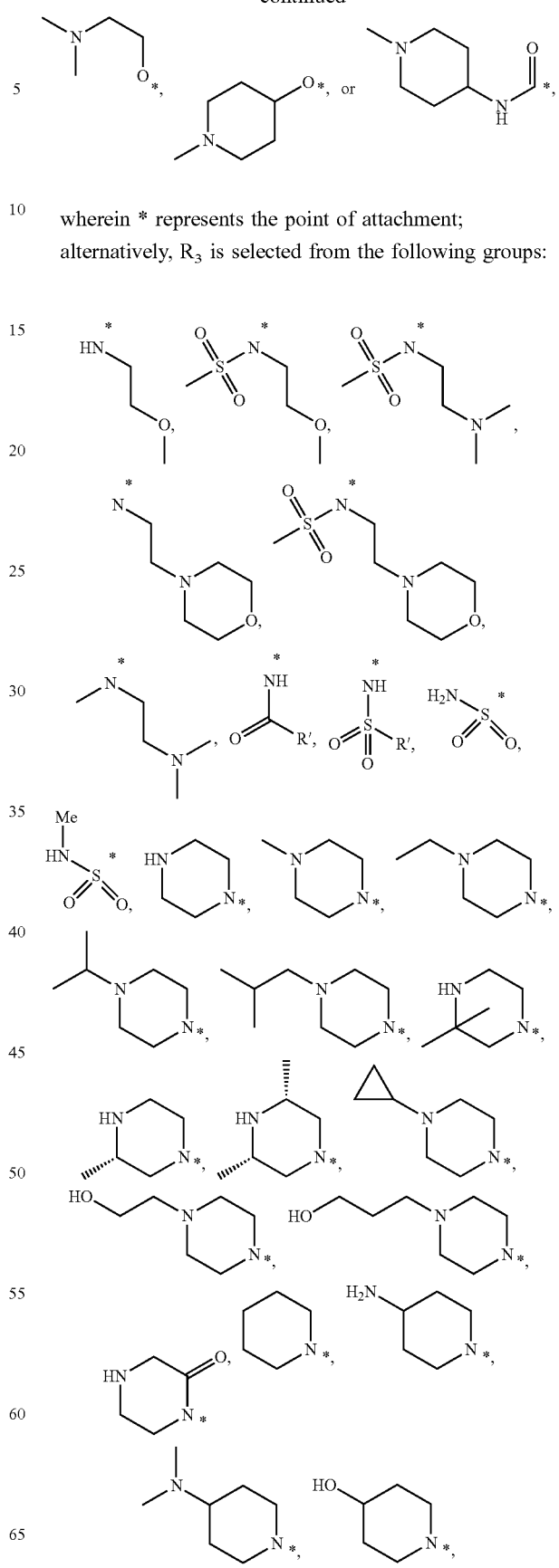
wherein * represents the point of attachment;
alternatively, $R_3$ is selected from the following groups:

-continued

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein,
$R_4$ is selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
alternatively, $R_4$ is selected from H, $C_{1-6}$ alkyl, $C_{1-6}$ haloalkyl, $C_{3-7}$ cycloalkyl or 3- to 7-membered heterocyclyl;
alternatively, $R_4$ is selected from $C_{1-6}$ alkyl, $C_{1-6}$ haloalkyl, $C_{3-7}$ cycloalkyl or 3- to 7-membered heterocyclyl;
alternatively, $R_4$ is selected from isopropyl, isobutyl or cyclopentyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, L is bond.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein,
$R_5$, $R_6$ and $R_7$ are independently selected from H, D, halogen, —CN, —$OR_a$, —$SR_a$, —$NR_bR_c$, —C(O)$R_a$, —C(O)O$R_a$, —C(O)N$R_bR_c$, —S(O)$_m$$R_a$, —S(O)$_m$O$R_a$, —S(O)$_m$N$R_bR_c$, $C_{1-6}$ alkyl or $C_{1-6}$ haloalkyl;
alternatively, wherein $R_5$ is selected from H, D, halogen, —CN, —$OR_a$, —$SR_a$, —$NR_bR_c$, $C_{1-6}$ alkyl or $C_{1-6}$ haloalkyl;
alternatively, $R_5$, $R_6$ and $R_7$ are independently selected from H, D, halogen, —C(O)$R_a$, —C(O)O$R_a$, —C(O)N$R_bR_c$, —S(O)$_m$$R_a$, —S(O)$_m$O$R_a$ or —S(O)$_m$N$R_bR_c$;
alternatively, wherein $R_5$ is selected from H, D, halogen, —$OR_a$, —$SR_a$ or —$NR_bR_c$;
alternatively, $R_5$, $R_6$ and $R_7$ are independently selected from H, halogen, —CN, —$OR_a$, —$SR_a$, —$NR_bR_c$, $C_{1-6}$ alkyl or $C_{1-6}$ haloalkyl;
alternatively, $R_5$, $R_6$ and $R_7$ are independently selected from H, halogen, —CN, —$OR_a$, $C_{1-6}$ alkyl or $C_{1-6}$ haloalkyl;
alternatively, $R_7$ is H or halogen; alternatively, $R_7$ is F.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein,
$R_8$ is selected from H, D, —NH$_2$, —NHC$_{1-6}$ alkyl, —N(C$_{1-6}$ alkyl)$_2$, $C_{1-6}$ alkyl, $C_{1-6}$ haloalkyl, —$C_{0-6}$ alkylene-O$R_a$, $C_{3-7}$ cycloalkyl or 3- to 7-membered heterocyclyl; or two $R_8$ groups on the same atom are taken together to form oxo or thioxo;
alternatively, $R_8$ is selected from H, D, —NH$_2$, —NHC$_{1-6}$ alkyl, —N(C$_{1-6}$ alkyl)$_2$, $C_{1-6}$ alkyl or $C_{1-6}$ haloalkyl; or two $R_8$ groups on the same atom are taken together to form oxo or thioxo;
alternatively, $R_8$ is selected from H, D, $C_{1-6}$ alkyl or $C_{1-6}$ haloalkyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein,
$A_1$ is selected from C$R_5$ or N;
$A_2$ is selected from C$R_6$ or N;
$A_3$ is selected from C$R_7$ or N;
$R_1$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_3$ is selected from H, halogen, —CN, —NO$_2$, —$OR_a$, —$SR_a$, —$NR_bR_c$, —C(O)$R_a$, —C(O)O$R_a$, —C(O)N$R_bR_c$, —S(O)$_m$$R_a$, —S(O)$_m$O$R_a$, —S(O)$_m$N$R_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);
$R_4$ is selected from H, —C(O)$R_a$, —C(O)O$R_a$, —C(O)N$R_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;
wherein,
$R_5$ is selected from H, halogen, —CN, —$OR_a$, —$SR_a$, —$NR_bR_c$, $C_{1-6}$ alkyl or $C_{1-6}$ haloalkyl;
$R_6$ is selected from H, halogen, —CN, —$OR_a$, —$SR_a$, —$NR_bR_c$, $C_{1-6}$ alkyl or $C_{1-6}$ haloalkyl;
$R_7$ is selected from H, halogen, —CN, —$OR_a$, —$SR_a$, —$NR_bR_c$, $C_{1-6}$ alkyl or $C_{1-6}$ haloalkyl;
$R_8$ is selected from H, —NH$_2$, —NHC$_{1-6}$ alkyl, —N(C$_{1-6}$ alkyl)$_2$, $C_{1-6}$ alkyl, $C_{1-6}$ haloalkyl, —$C_{0-6}$ alkylene-O$R_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;
$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;
$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, $R_b$ and $R_c$ are taken together with the nitrogen atoms to which they are attached to form 3- to 7-membered heterocyclyl;

m represents 0, 1 or 2;

and, $R_1$—$R_2$ and $R_4$—$R_8$ are optionally substituted with 1, 2 or 3 R' group(s), wherein R' is independently selected from H, —OH, halogen, —$NO_2$, carbonyl, —CN, —$OR_a$, —$SR_a$, —$NR_bR_c$, —$C(O)R_a$, —$C(S)R_a$, —$C(O)OR_a$, —$C(S)OR_a$, —$C(O)$—$NR_bR_c$, —$C(S)$—$NR_bR_c$, —O—$C(O)R_a$, —O—$C(S)R_a$, —$N(R_b)$—$C(O)$—$R_a$, —$N(R_b)$—$C(S)$—$R_a$, —$S(O)_mR_a$, —$S(O)_mOR_a$, —$S(O)_mNR_bR_c$, —$N(R_b)$—$S(O)_m$—$R_a$, —$N(R_b)$—$S(O)_m$—$NR_bR_c$, —$N(R_b)$—$C(O)OR_a$, —$N(R_b)$—$C(S)OR_a$, —O—$C_{1-6}$ alkylene-$OR_a$, —$C(O)$—$C_{1-6}$ alkylene-$NR_bR_c$, —$N(R_b)$—$C(O)$—$NR_bR_c$, —$N(R_b)$—$C(S)$—$NR_bR_c$, —O—$C(O)$—$NR_bR_c$, —O—$C(S)$—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl;

$R_a$, $R_b$ and $R_c$ are optionally further substituted with one or more of the following groups:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is selected from $CR_5$ or N;

$A_2$ is selected from $CR_6$ or N;

$A_3$ is selected from $CR_7$ or N;

$R_1$ is selected from H, halogen, —CN, $C_{1-6}$ alkyl, $C_{1-6}$ haloalkyl, $C_{3-7}$ cycloalkyl or 5- to 10-membered heteroaryl; wherein the $C_{3-7}$ cycloalkyl or 3- to 7-membered heterocyclyl is optionally substituted with oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_3$ is selected from H, halogen, —CN, —$NO_2$, —$OR_a$, —$SR_a$, —$NR_bR_c$, —$C(O)R_a$, —$C(O)OR_a$, —$C(O)NR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);

$R_4$ is selected from H, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

wherein, $R_5$ is selected from H, halogen, —CN, —$OR_a$, $C_{1-6}$ alkyl or $C_{1-6}$ haloalkyl;

$R_6$ is selected from H, halogen, —CN, —$OR_a$, $C_{1-6}$ alkyl or $C_{1-6}$ haloalkyl;

$R_7$ is selected from H, halogen, —CN, —$OR_a$, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl, $C_{2-6}$ alkenyl, $C_{2-6}$ alkynyl, or $C_{1-6}$ haloalkyl;

$R_b$ and $R_c$ are independently selected from H, $C_{1-6}$ alkyl, $C_{2-6}$ alkenyl, $C_{2-6}$ alkynyl, or $C_{1-6}$ haloalkyl; or, $R_b$ and $R_c$ are taken together with the nitrogen atoms to which they are attached to form 3- to 7-membered heterocyclyl;

and, $R_1$—$R_2$ and $R_4$—$R_5$ are optionally substituted with 1, 2 or 3 R' group(s), wherein R' is independently selected from H, —OH, halogen, —$NO_2$, carbonyl, —CN, —$OR_a$, —$SR_a$, —$NR_bR_c$, —$C(O)R_a$, —$C(S)R_a$, —$C(O)OR_a$, —$C(S)OR_a$, —$C(O)$—$NR_bR_c$, —$C(S)$—$NR_bR_c$, —O—$C(O)R_a$, —O—$C(S)R_a$, —$N(R_b)$—$C(O)$—$R_a$, —$N(R_b)$—$C(S)$—$R_a$, —$N(R_b)$—$C(O)OR_a$, —$N(R_b)$—$C(S)OR_a$, —O—$C_{1-6}$ alkylene-$OR_a$, —$C(O)$—$C_{1-6}$ alkylene-$NR_bR_c$, —$N(R_b)$—$C(O)$—$NR_bR_c$, —$N(R_b)$—$C(S)$—$NR_bR_c$, —O—$C(O)$—$NR_bR_c$, —O—$C(S)$—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl;

$R_a$, $R_b$ and $R_c$ are optionally further substituted with one or more of the following groups: $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is selected from $CR_5$ or N;

$A_2$ is selected from $CR_6$ or N;

$A_3$ is selected from $CR_7$ or N;

$R_1$ is selected from H, halogen, —CN, $C_{1-6}$ alkyl or $C_{1-6}$ haloalkyl;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;

$R_3$ is selected from H, halogen, —CN, —$NO_2$, —$OR_a$, —$SR_a$, —$NR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);

$R_4$ is selected from H, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

wherein, $R_5$ is selected from H, halogen, —CN, —$OR_a$, $C_{1-6}$ alkyl or $C_{1-6}$ haloalkyl;

$R_6$ is selected from H, halogen, —CN, —$OR_a$, $C_{1-6}$ alkyl or $C_{1-6}$ haloalkyl;

$R_7$ is selected from H, halogen, —CN, —$OR_a$, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene- $OR_a$, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl, $C_{2-6}$ alkenyl, $C_{2-6}$ alkynyl, or $C_{1-6}$ haloalkyl;

$R_b$ and $R_c$ are independently selected from H, $C_{1-6}$ alkyl, $C_{2-6}$ alkenyl, $C_{2-6}$ alkynyl, or $C_{1-6}$ haloalkyl; or, $R_b$ and $R_c$ are taken together with the nitrogen atoms to which they are attached to form 3- to 7-membered heterocyclyl;

and, $R_1$—$R_2$ and $R_4$—$R_8$ are optionally substituted with 1, 2 or 3 R' group(s), wherein R' is independently selected from H, —OH, halogen, —$NO_2$, carbonyl, —CN, —$OR_a$, —$SR_a$, —$NR_bR_c$, —$C(O)R_a$, —$C(O)OR_a$, —$C(O)$—$NR_bR_c$, —O—$C(O)R_a$, —$N(R_b)$—$C(O)$—$R_a$, —$N(R_b)$—$C(O)OR_a$, —O—$C_{1-6}$ alkylene-$OR_a$, —$C(O)$—$C_{1-6}$ alkylene-$NR_bR_c$, —$N(R_b)$—$C(O)$—$NR_bR_c$, —O—$C(O)$—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl;

$R_a$, $R_b$ and $R_c$ are optionally further substituted with one or more of the following groups:

$C_{1-6}$ alkyl, $C_{2-6}$ alkenyl, $C_{2-6}$ alkynyl, or $C_{1-6}$ haloalkyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is selected from $CR_5$ or N;
$A_2$ is selected from $CR_6$ or N;
$A_3$ is selected from $CR_7$ or N;
$R_1$ is selected from H, halogen, —CN, $C_{1-6}$ alkyl or $C_{1-6}$ haloalkyl;
$R_2$ is selected from H, halogen, —CN, $C_{1-6}$ alkyl or $C_{1-6}$ haloalkyl;
$R_3$ is selected from H, halogen, —CN, —O—$C_{1-6}$ alkylene-$R_8$, $C_{1-6}$ alkyl, $C_{1-6}$ haloalkyl, $C_{3-7}$ cycloalkyl or 3- to 11-membered heterocyclyl, each of which is optionally substituted with 1, 2, 3, 4 or 5 $R_8$ group(s);
$R_4$ is selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, halogen, —CN, —$OR_a$, $C_{1-6}$ alkyl or $C_{1-6}$ haloalkyl;
$R_6$ is selected from H, halogen, —CN, —$OR_a$, $C_{1-6}$ alkyl or $C_{1-6}$ haloalkyl;
$R_7$ is selected from H, halogen, —CN, —$OR_a$, $C_{1-6}$ alkyl or $C_{1-6}$ haloalkyl;
$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl, $C_{2-6}$ alkenyl, $C_{2-6}$ alkynyl, or $C_{1-6}$ haloalkyl;

$R_b$ and $R_c$ are independently selected from H, $C_{1-6}$ alkyl, $C_{2-6}$ alkenyl, $C_{2-6}$ alkynyl, or $C_{1-6}$ haloalkyl; or, $R_b$ and $R_c$ are taken together with the nitrogen atoms to which they are attached to form 3- to 7-membered heterocyclyl;

and, $R_1$—$R_2$ and $R_4$—$R_8$ are optionally substituted with 1, 2 or 3 R' group(s), wherein R' is independently selected from H, —OH, halogen, —$NO_2$, carbonyl, —CN, —$OR_a$, —$NR_bR_c$, —O—$C_{1-6}$ alkylene-$OR_a$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is selected from $CR_5$ or N;
$A_2$ is selected from $CR_6$ or N;
$A_3$ is selected from $CR_7$ or N;
$R_1$ is selected from H, $C_{1-6}$ alkyl or $C_{1-6}$ haloalkyl;
$R_2$ is selected from H, halogen, —CN, $C_{1-6}$ alkyl or $C_{1-6}$ haloalkyl;
$R_3$ is selected from H, —O—$C_{1-6}$ alkylene-$R_8$, $C_{1-6}$ alkyl, $C_{1-6}$ haloalkyl, $C_{3-7}$ cycloalkyl or 3- to 11-membered heterocyclyl, each of which is optionally substituted with 1, 2, 3, 4 or 5 $R_8$ group(s);
$R_4$ is selected from H, $C_{1-6}$ alkyl, $C_{1-6}$ haloalkyl, $C_{3-7}$ cycloalkyl or 3- to 7-membered heterocyclyl;
L is selected from bond, —O—, —NH—, —C(O)—, —C(O)NH—, —NHC(O)— or —$C_{1-6}$ alkylene-;

and wherein, $R_5$ is selected from H, halogen, —CN, —$OR_a$, $C_{1-6}$ alkyl or $C_{1-6}$ haloalkyl;
$R_6$ is selected from H, halogen, —CN, —$OR_a$, $C_{1-6}$ alkyl or $C_{1-6}$ haloalkyl;
$R_7$ is selected from H, halogen, —CN, —$OR_a$, $C_{1-6}$ alkyl or $C_{1-6}$ haloalkyl;
$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 3- to 7-membered heterocyclyl;

and, $R_8$ is optionally substituted with 1, 2 or 3 R' group(s), wherein R' is independently selected from H, —OH, halogen, —$NO_2$, carbonyl, —CN, —$OR_a$, —$NR_bR_c$, —O—$C_{1-6}$ alkylene-$OR_a$, $C_{1-6}$ alkyl or $C_{1-6}$ haloalkyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, wherein, $A_1$ is selected from $CR_5$ or N;
$A_2$ is selected from $CR_6$ or N;
$A_3$ is selected from $CR_7$;
$R_1$ is selected from H or $C_{1-6}$ alkyl;
$R_2$ is selected from H or —CN;
$R_3$ is selected from H, —O—$C_{1-6}$ alkylene-$R_8$, $C_{3-7}$ cycloalkyl or 3- to 11-membered heterocyclyl, each of which is optionally substituted with 1, 2, 3, 4 or 5 $R_8$ group(s);

$R_4$ is selected from H, $C_{1-6}$ alkyl or $C_{3-7}$ cycloalkyl;

L is selected from bond, —O—, —C(O)—, —C(O)NH—, —NHC(O)— or —$C_{1-6}$ alkylene-;

and wherein, $R_5$ is selected from H, halogen or —$OR_a$;

$R_6$ is selected from H or $C_{1-6}$ alkyl;

$R_7$ is selected from H, halogen or $C_{1-6}$ alkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ taken together with the nitrogen atoms to which they are attached to form 3- to 7-membered heterocyclyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (II):

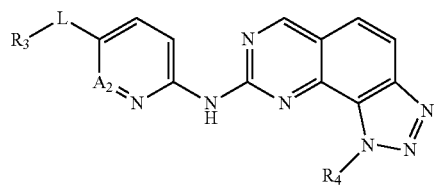

(II)

wherein:

$A_2$ is selected from $CR_6$ or N;

$R_3$ is selected from the following groups, each of which is optionally substituted with 1, 2, 3, 4 or 5 $R_8$ group(s):

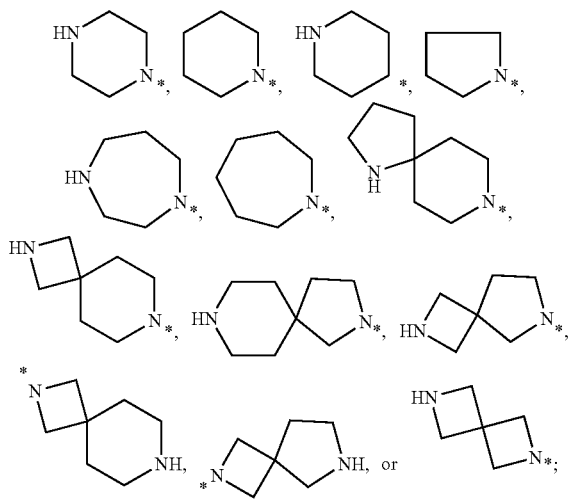

$R_4$ is selected from $C_{1-6}$ alkyl, $C_{1-6}$ haloalkyl or $C_{3-7}$ cycloalkyl;

L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

$R_6$ is selected from H, halogen, —CN, —$OR_a$, —$SR_a$, —$NR_bR_c$, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, $C_{3-7}$ cycloalkyl or 3- to 7-membered heterocyclyl; or two $R_8$ groups on the same atom are taken together to form oxo or thioxo;

$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, $R_b$ and $R_c$ are taken together with the nitrogen atoms to which they are attached to form 3- to 7-membered heterocyclyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (II):

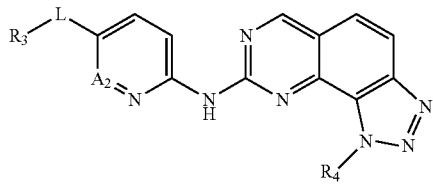

(II)

wherein:

$A_2$ is selected from $CR_6$ or N;

$R_3$ is selected from the following groups, each of which is optionally substituted with 1, 2 or 3 $R_8$ group(s):

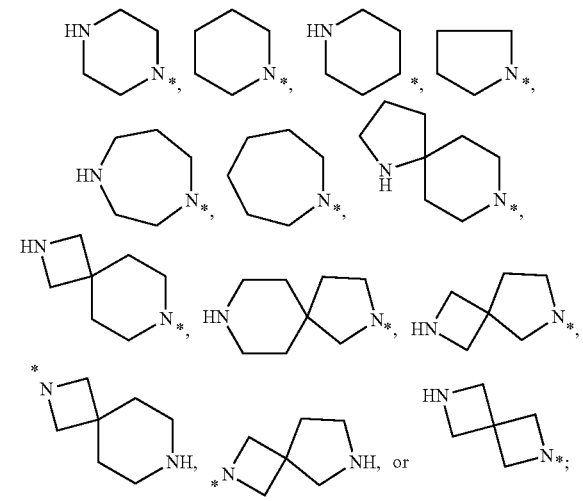

$R_4$ is selected from $C_{1-6}$ alkyl, $C_{1-6}$ haloalkyl or $C_{3-7}$ cycloalkyl;

L is selected from bond, —$C_{1-6}$ alkylene-, —$C_{2-6}$ alkenylene- or —$C_{2-6}$ alkynylene-;

$R_6$ is selected from H, halogen, —CN, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, $C_{3-7}$ cycloalkyl or 3- to 7-membered heterocyclyl; or two $R_8$ groups on the same atom are taken together to form oxo or thioxo.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (II):

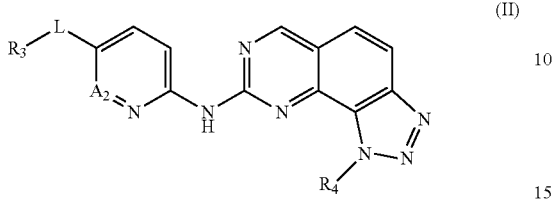

wherein:
$A_2$ is selected from $CR_6$ or N;
$R_3$ is selected from the following groups:

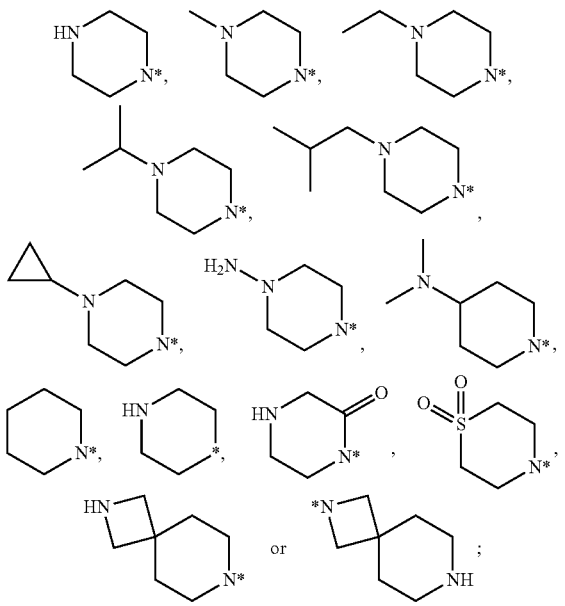

$R_4$ is selected from $C_{1-6}$ alkyl or $C_{3-7}$ cycloalkyl;
L is selected from bond, or —$C_{1-6}$ alkylene-;
$R_6$ is selected from H or $C_{1-6}$ alkyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (III) or (III-1):

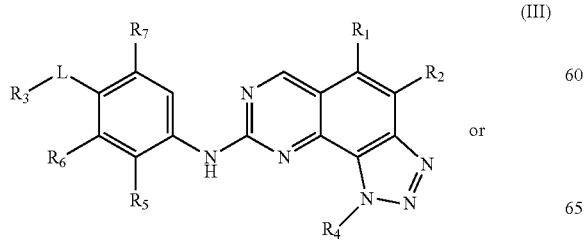

or

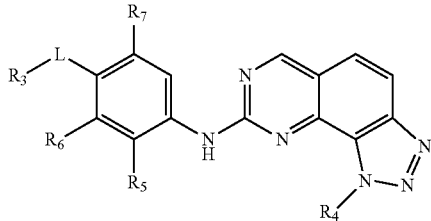

wherein:
$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 $R_8$ group(s);
$R_4$ is selected from H, D, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
$R_5$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
$R_6$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
$R_7$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;
L is selected from bond, —O—, —NH—, —C(O)—, —C(O)NH— or —NHC(O)—;
$R_8$ is selected from H, D, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;
$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_mR'$, —$C_{0-6}$ alkylene-$S(O)_mOR'$, —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R'" are taken together with the nitrogen atoms to which they are attached to form 3- to 7-membered heterocyclyl;

m represents 0, 1 or 2.

In a more specific embodiment, the present disclosure provides a compound of the above formula (III) or (III-1), or a pharmaceutically acceptable salt, enantiomer, diastereomer, racemate, solvate, hydrate, polymorph, prodrug, or isotopic variant thereof, or a mixture thereof, wherein:

$R_1$ is selected from H, D, halogen, —CN, —$OR_a$, —$SR_a$, —$NR_bR_c$, $C_{1-6}$ alkyl or $C_{1-6}$ haloalkyl;

$R_2$ is selected from H, D, halogen, —CN, —$OR_a$, —$SR_a$, —$NR_bR_c$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{1-6}$ alkyl, $C_{1-6}$ haloalkyl, $C_{3-7}$ cycloalkyl or 4- to 7-membered heterocyclyl, each of which is optionally substituted with 1, 2 or 3 $R_8$ group(s);

$R_4$ is selected from H, D, $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —NH$C_{1-6}$ alkyl, —N($C_{1-6}$ alkyl)$_2$, $C_{1-6}$ alkyl or $C_{1-6}$ haloalkyl; or two $R_8$ groups on the same atom are taken together to form oxo or thioxo;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R'" are taken together with the nitrogen atoms to which they are attached to form 3- to 7-membered heterocyclyl;

m represents 0, 1 or 2.

In a more specific embodiment, the present disclosure provides a compound of the above formula (III) or (III-1), or a pharmaceutically acceptable salt, enantiomer, diastereomer, racemate, solvate, hydrate, polymorph, prodrug, or isotopic variant thereof, or a mixture thereof, wherein:

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{3-7}$ cycloalkyl or 4- to 7-membered heterocyclyl, each of which is optionally substituted with 1 or 2 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)O$R_a$, —C(O)N$R_bR_c$, —S(O)$_mR_a$, —S(O)$_m$O$R_a$, —S(O)$_m$N$R_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —NH$C_{1-6}$ alkyl, —N($C_{1-6}$ alkyl)$_2$, $C_{1-6}$ alkyl or $C_{1-6}$ haloalkyl;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R''' are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R''' are taken together with the nitrogen atoms to which they are attached to form 3- to 7-membered heterocyclyl;

m represents 0, 1 or 2.

In a more specific embodiment, the present disclosure provides a compound of the above formula (III) or (III-1), or a pharmaceutically acceptable salt, enantiomer, diastereomer, racemate, solvate, hydrate, polymorph, prodrug, or isotopic variant thereof, or a mixture thereof, wherein:

$R_1$ is selected from H or D;

$R_2$ is selected from H or D;

$R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{4-6}$ cycloalkyl or 5- to 6-membered heterocyclyl, each of which is optionally substituted with one $R_8$ group;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —$OR_a$, —$SR_a$ or —$NR_bR_c$;

$R_6$ is selected from H, D, halogen, —$C(O)R_a$, —$C(O)OR_a$, —$C(O)NR_bR_c$, —$S(O)_mR_a$, —$S(O)_mOR_a$ or —$S(O)_mNR_bR_c$;

$R_7$ is selected from H, D, halogen, —$C(O)R_a$, —$C(O)OR_a$, —$C(O)NR_bR_c$, —$S(O)_mR_a$, —$S(O)_mOR_a$ or —$S(O)_mNR_bR_c$;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, —$C_{0-6}$ alkylene-OR', —$C_{0-6}$ alkylene-NR"R''', —$C_{0-6}$ alkylene-C(O)R', —$C_{0-6}$ alkylene-S(O)$_m$R', $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-NR"R''', —$C_{0-6}$ alkylene-C(O)R', —$C_{0-6}$ alkylene-S(O)$_m$R', $C_{1-6}$ alkyl, $C_{1-6}$ haloalkyl, —$C_{0-6}$ alkylene-$C_{37}$ cycloalkyl or —$C_{0-6}$ alkylene-3- to 7-membered heterocyclyl; or, $R_b$ and $R_c$ are taken together with the nitrogen atoms to which they are attached to form 5- to 6-membered heterocyclyl;

R' is independently selected from H, $C_{1-6}$ alkyl or $C_{1-6}$ haloalkyl;

R" and R''' are independently selected from H, $C_{1-6}$ alkyl or $C_{1-6}$ haloalkyl; or, R" and R''' are taken together with the nitrogen atoms to which they are attached to form 5- to 6-membered heterocyclyl;

m represents 0, 1 or 2.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (III), (III-1) or (III-2):

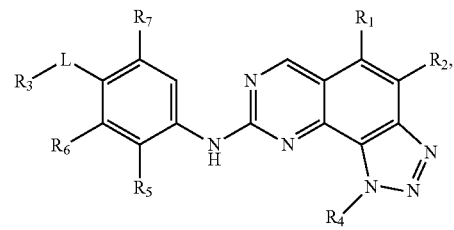

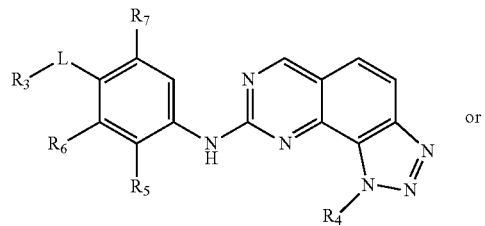

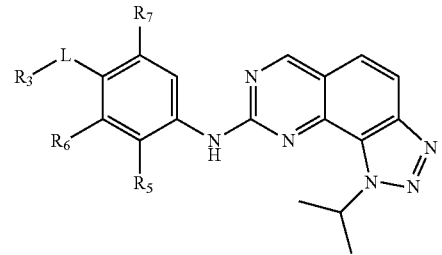

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, —$OR_a$, —$NR_bR_c$, $C_{1-6}$ alkyl, $C_{1-6}$ haloalkyl or 5- to 6-membered heterocyclyl, each of which is optionally substituted with 1, 2 or 3 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

In a more specific embodiment, the present disclosure provides a compound of the above formula (III), (III-1) or (III-2), or a pharmaceutically acceptable salt, enantiomer, diastereomer, racemate, solvate, hydrate, polymorph, prodrug, or isotopic variant thereof, or a mixture thereof, wherein:

$R_1$ is selected from H, D, halogen, —CN or —$OR_a$;

$R_2$ is selected from H, D, halogen, —CN or —$OR_a$;

R₃ is selected from H, D, —OR_a, —NR_bR_c, C_{1-6} alkyl, C_{1-6} haloalkyl or piperazinyl, each of which is optionally substituted with 1 or 2 R_8 group(s);

R₄ is selected from C_{1-6} alkyl, C_{1-6} haloalkyl, C_{3-7} cycloalkyl or 3- to 7-membered heterocyclyl;

R₅ is selected from H, D, halogen, —CN, —OR_a, —SR_a or —NR_bR_c;

R₆ is selected from H, D, halogen, —CN, —OR_a, —SR_a or —NR_bR_c;

R₇ is selected from H, D, halogen, —CN, —OR_a, —SR_a or —NR_bR_c;

L is selected from bond, —O—, —NH—, —C(O)—, —C(O)NH— or —NHC(O)—;

R_8 is selected from H, D, —NH₂, —NHC_{1-6} alkyl, —N(C_{1-6} alkyl)₂, C_{1-6} alkyl or C_{1-6} haloalkyl;

R_a is independently selected from H, C_{1-6} alkyl or C_{1-6} haloalkyl;

R_b and R_c are independently selected from H, C_{1-6} alkyl or C_{1-6} haloalkyl; or, R_b and R_c are taken together with the nitrogen atoms to which they are attached to form 5- to 6-membered heterocyclyl.

In a more specific embodiment, the present disclosure provides a compound of the above formula (III), (III-1) or (III-2), or a pharmaceutically acceptable salt, enantiomer, diastereomer, racemate, solvate, hydrate, polymorph, prodrug, or isotopic variant thereof, or a mixture thereof, wherein:

R₁ is selected from H or D;

R₂ is selected from H or D;

R₃ is selected from H, D, —OR_a, —NR_bR_c, C_{1-6} alkyl, C_{1-6} haloalkyl or piperazinyl, each of which is optionally substituted with one R_8 group;

R₄ is selected from C_{1-6} alkyl, C_{1-6} haloalkyl, C_{3-7} cycloalkyl or 3- to 7-membered heterocyclyl;

R₅ is selected from H, D, halogen, —CN, —OR_a, —SR_a or —NR_bR_c;

R₆ is selected from H, D or halogen;

R₇ is selected from H, D or halogen;

L is selected from bond, —O—, —NH— or —C(O)—;

R_8 is selected from H, D, —NH₂, —NHC_{1-6} alkyl, —N(C_{1-6} alkyl)₂, C_{1-6} alkyl or C_{1-6} haloalkyl;

R_a is independently selected from H, C_{1-6} alkyl or C_{1-6} haloalkyl;

R_b and R_c are independently selected from H, C_{1-6} alkyl or C_{1-6} haloalkyl; or, R_b and R_c are taken together with the nitrogen atoms to which they are attached to form 5- to 6-membered heterocyclyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (IV) or (IV-1):

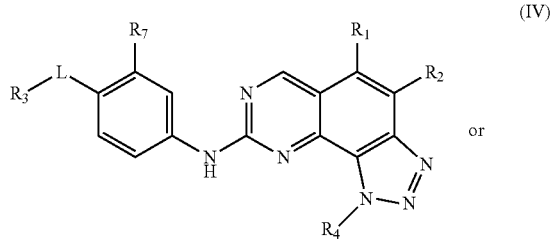

(IV)

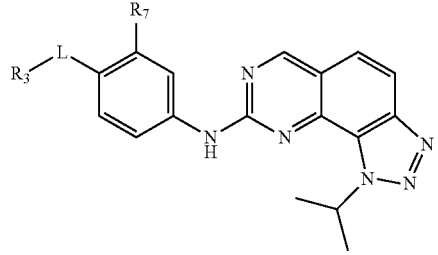

(IV-1)

wherein,

R₁ is selected from H, D, halogen, —CN, —OR_a, C_{1-6} alkyl or C_{1-6} haloalkyl;

R₂ is selected from H, D, halogen, —CN, —OR_a, C_{1-6} alkyl or C_{1-6} haloalkyl;

R₃ is selected from H, D, —OR_a, —NR_bR_c, C_{1-6} alkyl, C_{1-6} haloalkyl or 5- to 6-membered heterocyclyl, each of which is optionally substituted with 1, 2 or 3 R_8 group(s);

R₄ is selected from C_{1-6} alkyl, C_{1-6} haloalkyl, C_{3-7} cycloalkyl or 3- to 7-membered heterocyclyl;

L is selected from bond, —O—, —NH—, —C(O)—, —C(O)NH— or —NHC(O)—;

R₇ is selected from H, D, halogen, —CN, —OR_a, C_{1-6} alkyl or C_{1-6} haloalkyl;

R_8 is selected from H, —NH₂, —NHC_{1-6} alkyl, —N(C_{1-6} alkyl)₂, C_{1-6} alkyl, C_{1-6} haloalkyl or —C_{0-6} alkylene-OR_a;

R_a is independently selected from H, C_{1-6} alkyl or C_{1-6} haloalkyl;

R_b and R_c are independently selected from H, C_{1-6} alkyl or C_{1-6} haloalkyl; or, R_b and R_c are taken together with the nitrogen atoms to which they are attached to form 5- to 6-membered heterocyclyl.

In a more specific embodiment, the present disclosure provides a compound of the above formula (IV) or (IV-1), or a pharmaceutically acceptable salt, enantiomer, diastereomer, racemate, solvate, hydrate, polymorph, prodrug, or isotopic variant thereof, or a mixture thereof, wherein:

R₁ is selected from H, D, halogen, —CN or —OR_a;

R₂ is selected from H, D, halogen, —CN or —OR_a;

R₃ is selected from H, D, —OR_a, —NR_bR_c, C_{1-6} alkyl, C_{1-6} haloalkyl or piperazinyl, each of which is optionally substituted with 1 or 2 R_8 group(s);

R₄ is selected from C_{1-6} alkyl, C_{1-6} haloalkyl, C_{3-7} cycloalkyl or 3- to 7-membered heterocyclyl;

L is selected from bond, —O—, —NH—, —C(O)—, —C(O)NH— or —NHC(O)—;

R₇ is selected from H, D, halogen, —CN, —OR_a, C_{1-6} alkyl or C_{1-6} haloalkyl;

R_8 is selected from H, D, —NH₂, —NHC_{1-6} alkyl, —N(C_{1-6} alkyl)₂, C_{1-6} alkyl or C_{1-6} haloalkyl;

R_a is independently selected from H, C_{1-6} alkyl or C_{1-6} haloalkyl;

R_b and R_c are independently selected from H, C_{1-6} alkyl or C_{1-6} haloalkyl; or, R_b and R_c are taken together with the nitrogen atoms to which they are attached to form 5- to 6-membered heterocyclyl.

In a more specific embodiment, the present disclosure provides a compound of the above formula (IV) or (IV-1), or a pharmaceutically acceptable salt, enantiomer, diastereomer, racemate, solvate, hydrate, polymorph, prodrug, or isotopic variant thereof, or a mixture thereof, wherein:
- $R_1$ is selected from H or D;
- $R_2$ is selected from H or D;
- $R_3$ is selected from H, D, —$OR_a$, —$NR_bR_c$, $C_{1-6}$ alkyl, $C_{1-6}$ haloalkyl or piperazinyl, each of which is optionally substituted with one $R_8$ group;
- $R_4$ is selected from $C_{1-6}$ alkyl, $C_{1-6}$ haloalkyl, $C_{3-7}$ cycloalkyl or 3- to 7-membered heterocyclyl;
- L is selected from bond, —O—, —NH— or —C(O)—;
- $R_7$ is selected from H, D or halogen;
- $R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;
- $R_a$ is independently selected from H, $C_{1-6}$ alkyl or $C_{1-6}$ haloalkyl;
- $R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

In a more specific embodiment, the present disclosure provides a compound of formula (I), or a pharmaceutically acceptable salt, enantiomer, diastereomer, racemate, solvate, hydrate, polymorph, prodrug, or isotopic variant thereof, or a mixture thereof, which is the compound of formula (V) or (V-1):

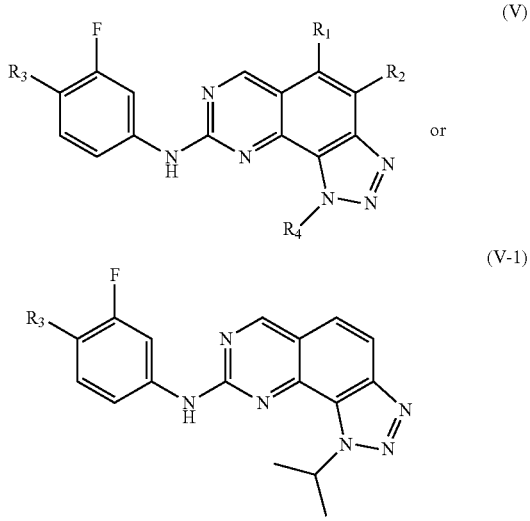

wherein,
- $R_1$ is selected from H, D, halogen, —CN, —$OR_a$, $C_{1-6}$ alkyl or $C_{1-6}$ haloalkyl;
- $R_2$ is selected from H, D, halogen, —CN, —$OR_a$, $C_{1-6}$ alkyl or $C_{1-6}$ haloalkyl;
- $R_3$ is 5- to 6-membered heterocyclyl optionally substituted with 1, 2 or 3 $R_8$ group(s);
- $R_4$ is selected from $C_{1-6}$ alkyl, $C_{1-6}$ haloalkyl, $C_{3-7}$ cycloalkyl or 3- to 7-membered heterocyclyl;
- $R_8$ is selected from H, —$NH_2$, —$NHC_{1-6}$ alkyl, —$N(C_{1-6}$ alkyl$)_2$, $C_{1-6}$ alkyl or $C_{1-6}$ haloalkyl;
- $R_a$ is independently selected from H, $C_{1-6}$ alkyl or $C_{1-6}$ haloalkyl.

In a more specific embodiment, the present disclosure provides a compound of the above formula (V) or (V-1), or a pharmaceutically acceptable salt, enantiomer, diastereomer, racemate, solvate, hydrate, polymorph, prodrug, or isotopic variant thereof, or a mixture thereof, wherein:
- $R_1$ is selected from H, D, halogen, —CN or —$OR_a$;
- $R_2$ is selected from H, D, halogen, —CN or —$OR_a$;
- $R_3$ is piperazinyl, each of which is optionally substituted with 1 or 2 $R_8$ group(s);
- $R_4$ is selected from $C_{1-6}$ alkyl, $C_{1-6}$ haloalkyl, $C_{3-7}$ cycloalkyl or 3- to 7-membered heterocyclyl;
- $R_8$ is selected from H, D, $C_{1-6}$ alkyl or $C_{1-6}$ haloalkyl;
- $R_a$ is independently selected from H, $C_{1-6}$ alkyl or $C_{1-6}$ haloalkyl.

In a more specific embodiment, the present disclosure provides a compound of the above formula (V) or (V-1), or a pharmaceutically acceptable salt, enantiomer, diastereomer, racemate, solvate, hydrate, polymorph, prodrug, or isotopic variant thereof, or a mixture thereof, wherein:
- $R_1$ is selected from H or D;
- $R_2$ is selected from H or D;
- $R_3$ is piperazinyl, each of which is optionally substituted with one $R_8$ group(s);
- $R_4$ is selected from $C_{1-6}$ alkyl, $C_{1-6}$ haloalkyl, $C_{3-7}$ cycloalkyl or 3- to 7-membered heterocyclyl;
- $R_8$ is selected from H, D, $C_{1-6}$ alkyl or $C_{1-6}$ haloalkyl.

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R.x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 H₂O)) and polyhydrates (x is a number greater than 1, for example, dihydrates (R·2 H₂O) and hexahydrates (R·6 H₂O)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes (isotope variants), which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P $^{35}$S, $^{18}$F and $^{36}$Cl, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^3$H and $^{14}$C), can be used for the measurement of the distribution of drug and/or substrate in tissue. Tritium, which is $^3$H and carbon-14, which is $^{14}$C isotope, are particularly preferred, because they are easy to prepare and detect. Furthermore, replaced by heavier isotopes, such as deuterium, which is $^2$H, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The present disclosure also provides a pharmaceutical formulation comprising a therapeutically effective amount of a compound of formula (I) or therapeutically acceptable salts thereof, and pharmaceutically acceptable carrier(s), diluent(s) or excipient(s) thereof. All of these forms belong to the present disclosure.

The preferred compounds disclosed herein include but are not limited to the following compounds, or the pharmaceutically acceptable salt, enantiomer, diastereomer, racemate, solvate, hydrate, polymorph, prodrug, or isotopic variant thereof, or a mixture thereof:

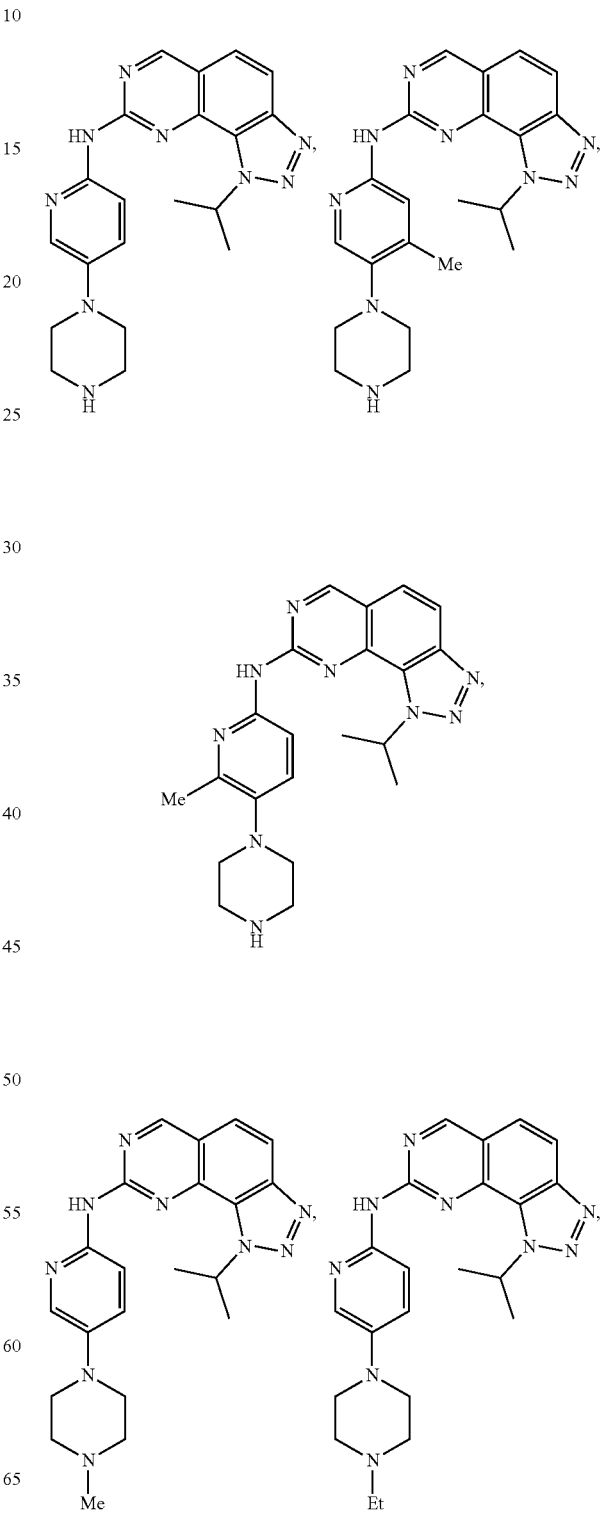

51
-continued
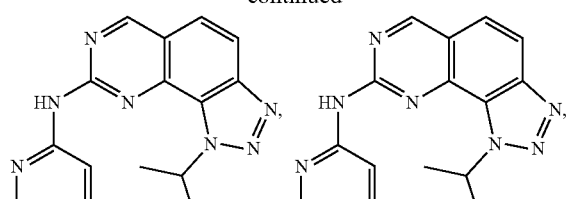
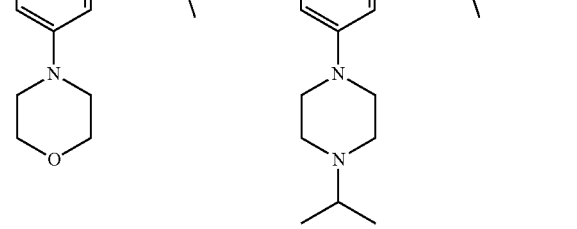
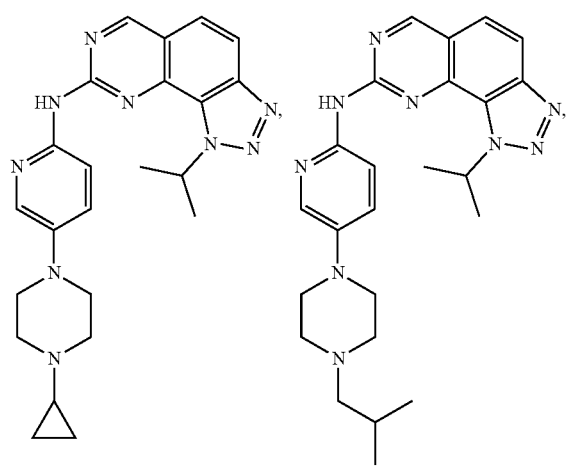
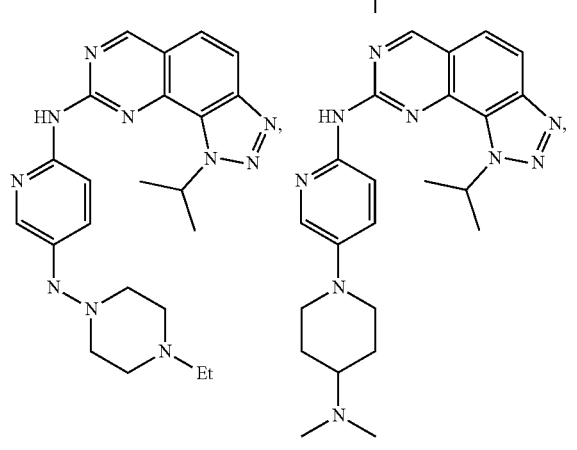
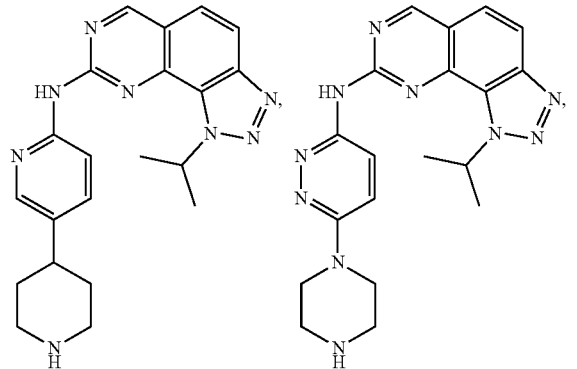
52
-continued
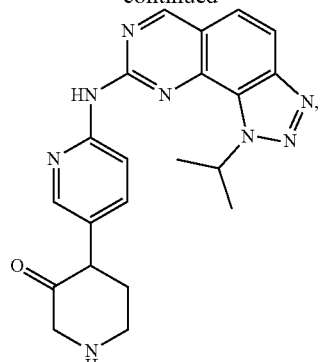
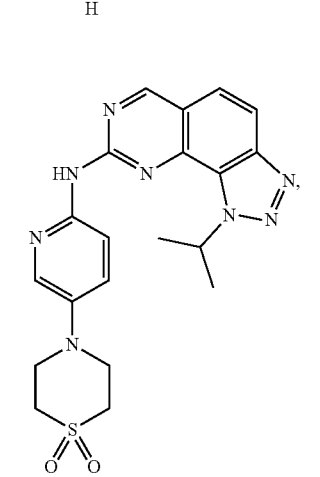
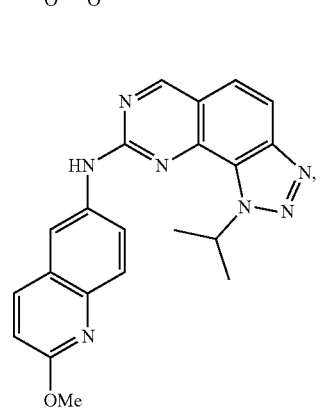
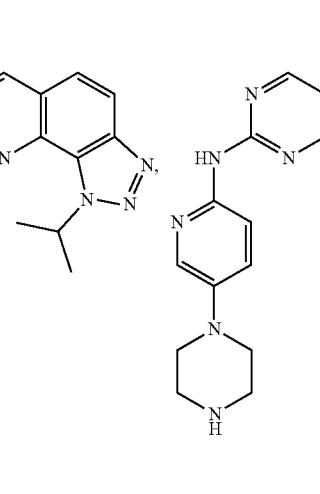

53
-continued
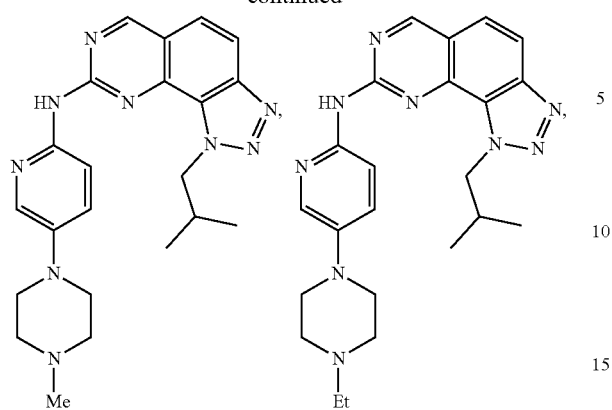
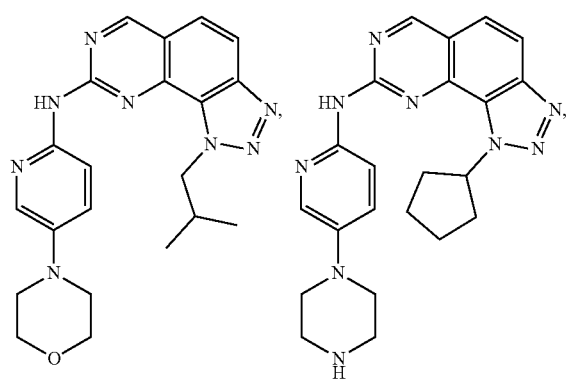
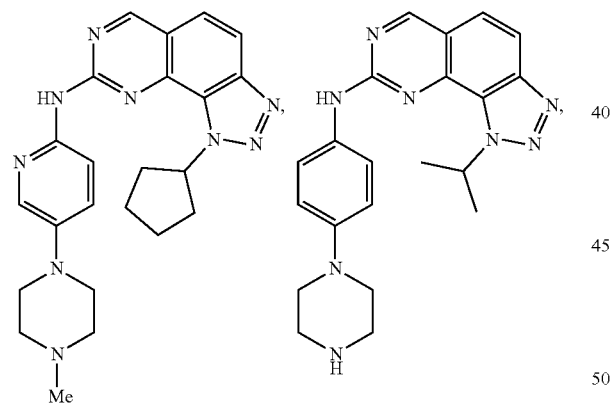
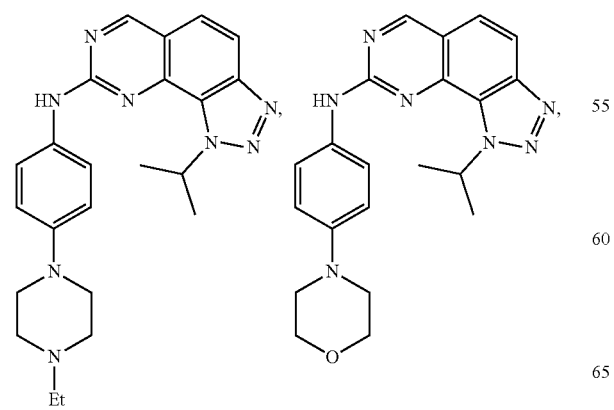
54
-continued
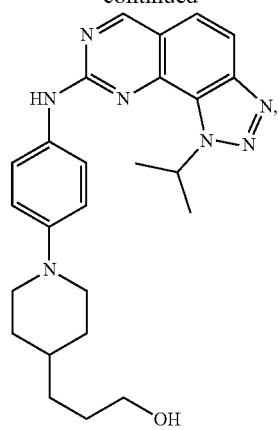
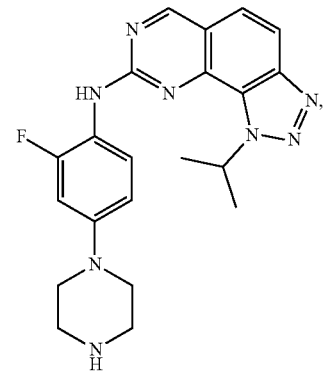
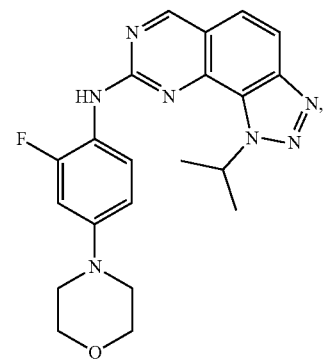
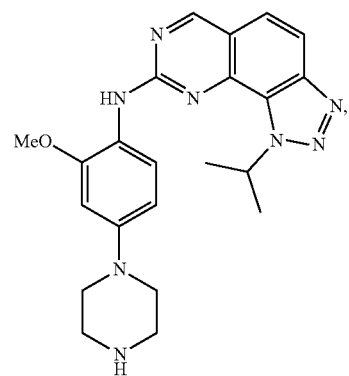

-continued
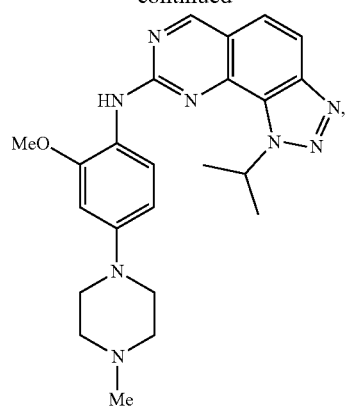
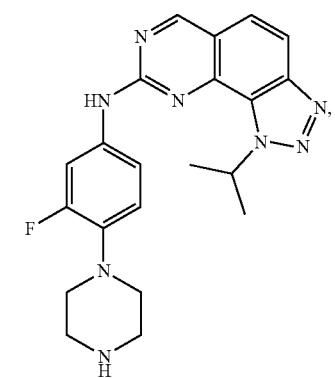
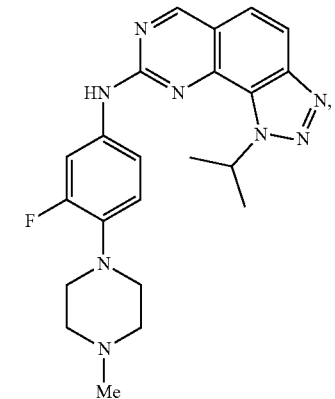
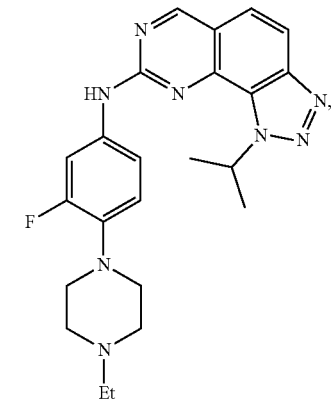
-continued
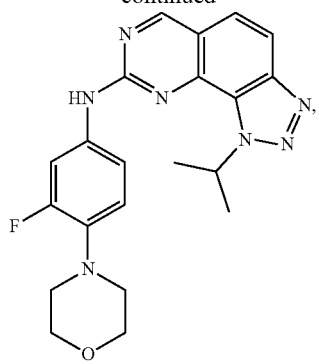
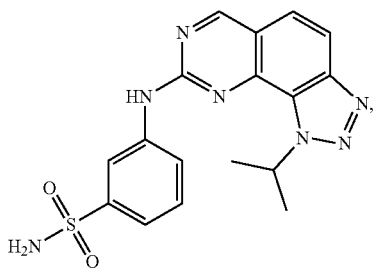
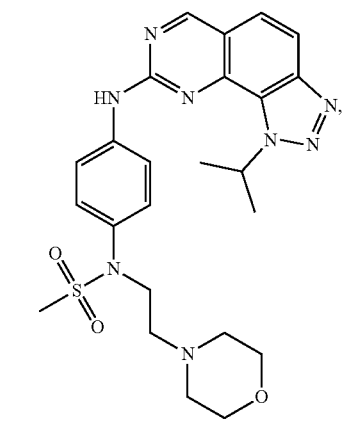

57
-continued

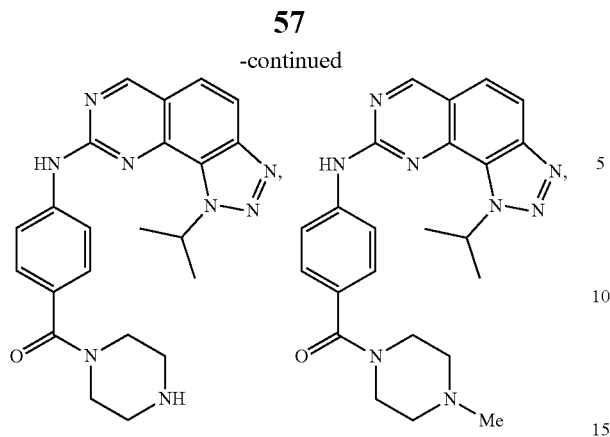
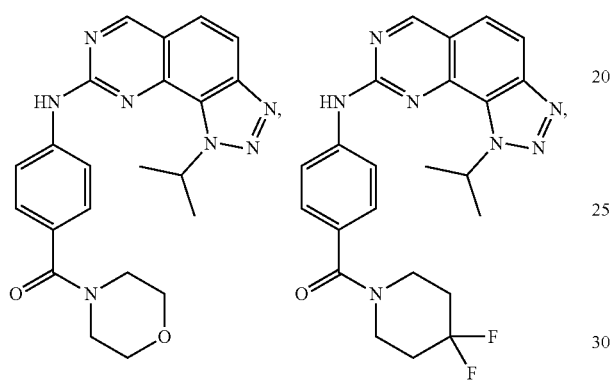
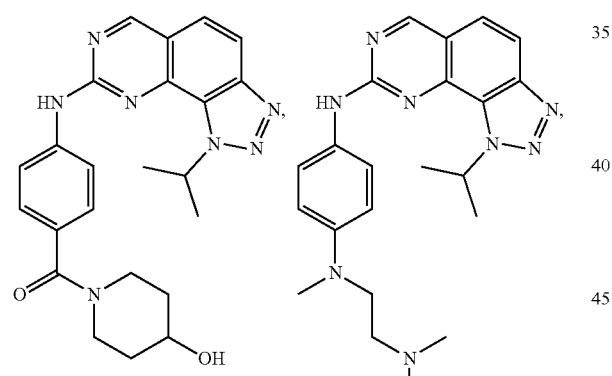
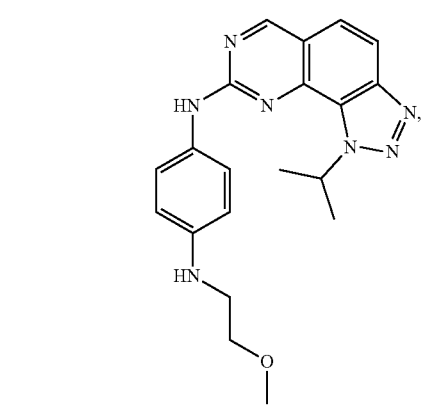

58
-continued

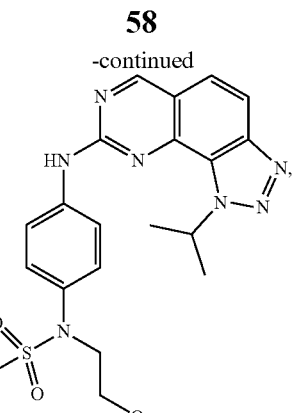
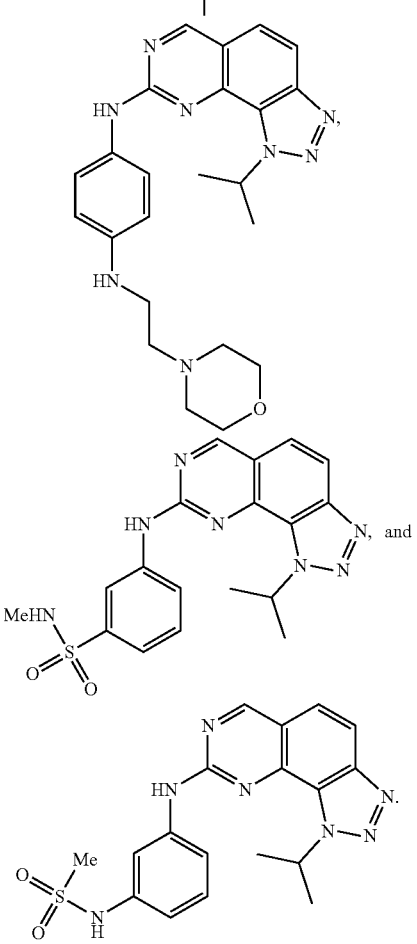

Pharmaceutical Compositions, Kits and Administration

In another aspect, the present disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agent(s), and a first and a second containers (e.g., vials, ampoules, bottles, syringes, and/or dispersible packages or other materials) containing the compound disclosed herein or other therapeutic agent(s). In some embodiments, kits provided can also optionally include a third container containing a pharmaceutically acceptable excipient for diluting or suspending the compound disclosed herein and/or other therapeutic agent(s). In some embodiments, the compound disclosed herein provided in the first container and the other therapeutic agent(s) provided in the second container is combined to form a unit dosage form.

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

EXAMPLES

The following examples are provided in order to provide those skilled in the art with a complete disclosure and description of how to implement, prepare and evaluate the methods and compounds claimed herein, and are intended to merely illustrate the present invention and not to limit the scope of the present disclosure.

The preparation scheme of the compounds of the present disclosure is shown in reaction scheme 1 for example.

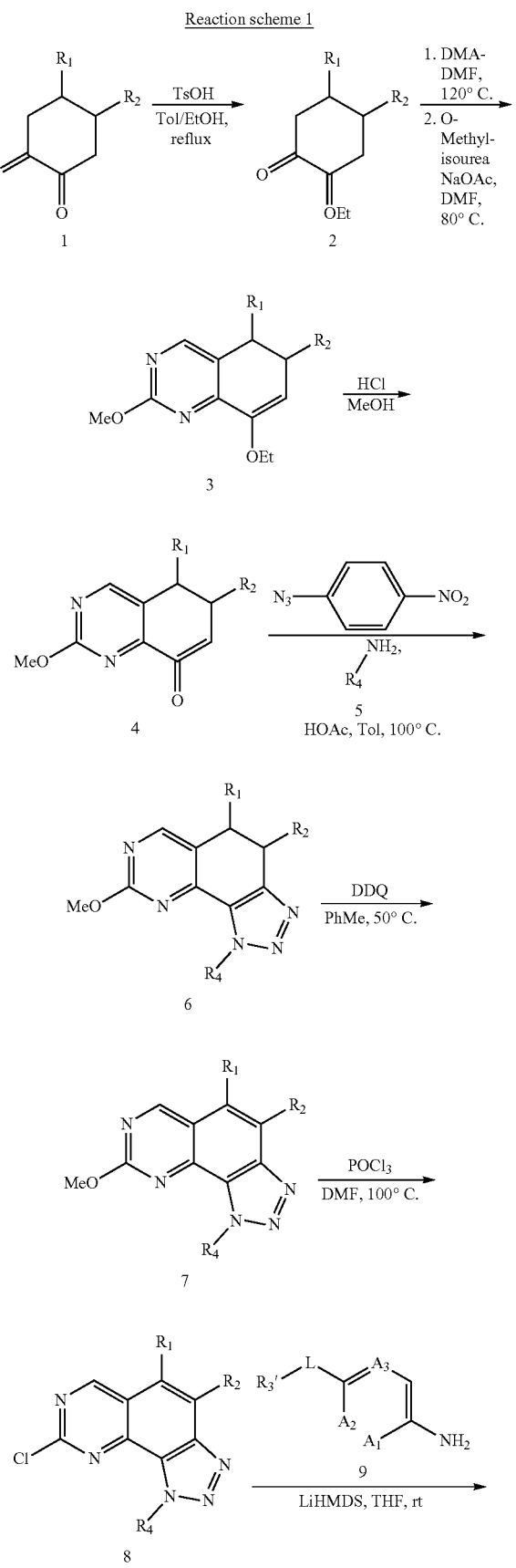

Example I-1

1-Isopropyl-N-(5-(piperazin-1-yl)pyridin-2-yl)-1H-[1,2,3]triazolo[4,5-h]quinazolin-8-amine hydrochloride (I-1)

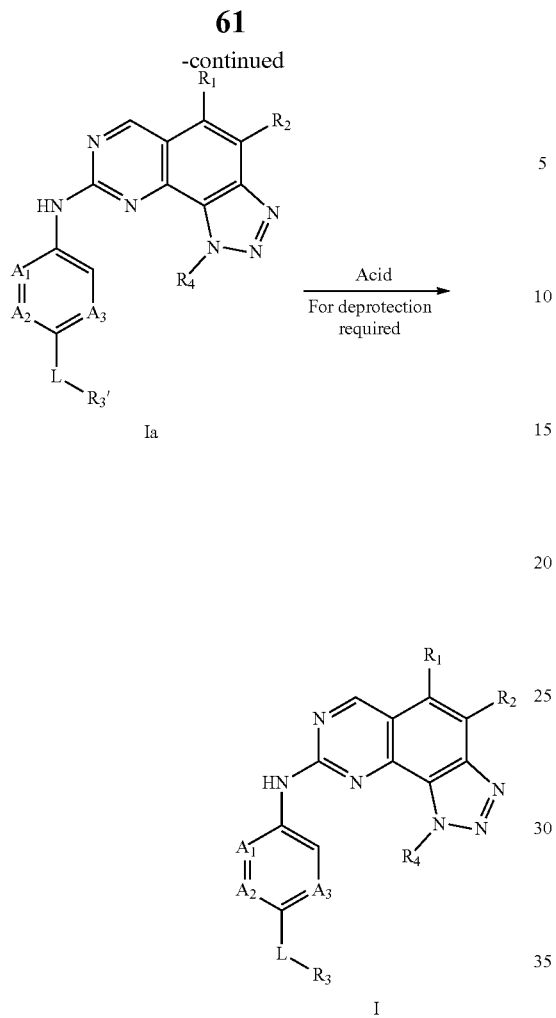

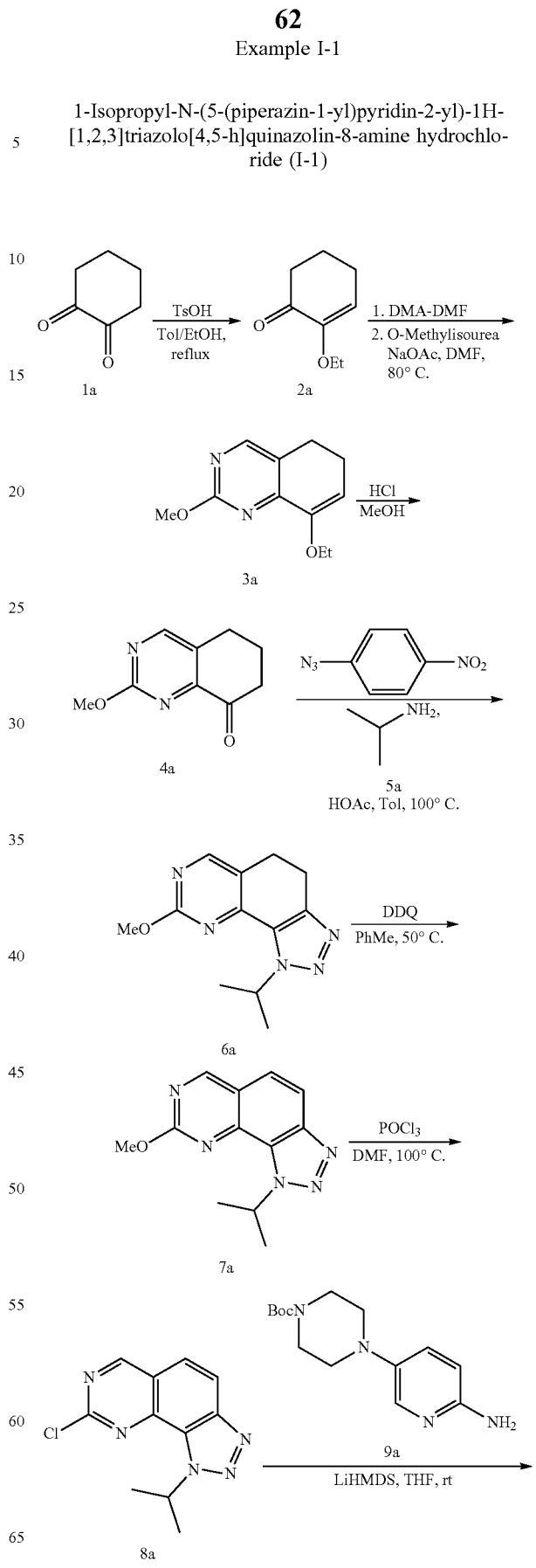

The compound of formula I can be prepared according to the above general reaction scheme. First, 1,2-cyclohexanedione (1) was catalyzed by p-toluenesulfonic acid and refluxed in toluene/ethanol to afford the enone intermediate (2). Then, the intermediate (2) was reacted with N,N-dimethylformamide dimethyl acetal, and the resulting enamine intermediate was further reacted with O-methyl isourea sulfate to afford 8-ethoxy-2-methoxy-5,6-dihydroquinazoline (3). Compound (3) was reacted with hydrogen chloride to afford 2-methoxy-6,7-dihydroquinazoline-8(5H)-one (4). Compound (4) was reacted with 1-azido-4-nitrobenzene and amine (5) to afford 1-substituted 8-methoxy-4,5-dihydro-1H-[1,2,3]triazolo[4,5-H]quinazoline (6). Then, the chlorinated compound (8) was obtained by the oxidation-aromatization reaction of compound 6 in the presence of 2,3-dichloro-5,6-dicyano-1,4-benzoquinone (DDQ) and the subsequent chlorination reaction in the presence of $POCl_3$. Compound (8) was coupled with the amine (9) to afford the compound of formula (Ia), wherein $R_3'$ represents $R_3$ protected by a protecting group (e.g. Boc), which is deprotected to afford the compound of formula (I); or when there is no need for a protecting group on $R_3$, $R_3'$ is $R_3$, and the compound of formula (Ia) is the compound of formula (I).

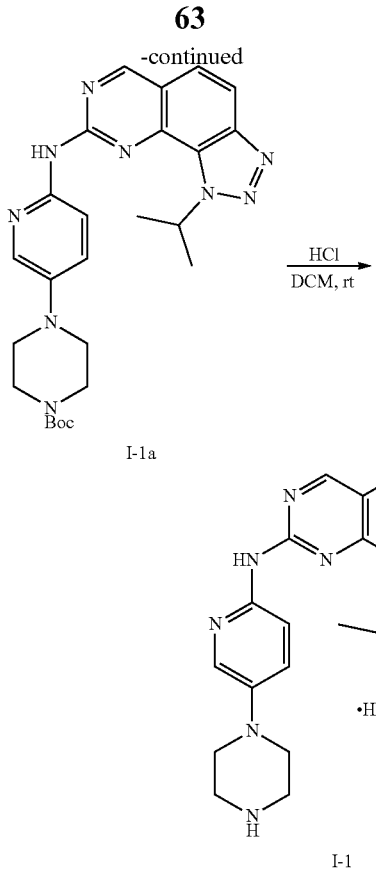

I-1a

•HCl

I-1

1): 2-ethoxycyclohex-2-en-1-one (2a)

1,2-Cyclohexanedione 1a (90 g, 803.2 mmol) and p-toluenesulfonic acid monohydrate (15.3 g, 80.3 mmol) were suspended in toluene/ethanol (2:1, 1000 mL), the suspension was heated to reflux and the reaction continued for 36 hours. After the reaction solution was cooled to room temperature, most of the solvent was removed by distillation under reduced pressure. Then, the mixture was neutralized with a saturated sodium bicarbonate aqueous solution (500 mL), and extracted three times with dichloromethane (200 mL). The organic layers were combined, dried (anhydrous sodium sulfate), suction filtered, and concentrated. The resulting residue was purified by flash silica gel column chromatography (petroleum ether/ethyl acetate=20:1) to afford a light yellow oily product, which was the title compound 2a (91.1 g, 650.6 mmol, 81%). $^1$H NMR (400 MHz, chloroform-d, ppm) δ 5.84 (t, J=4.6 Hz, 1H), 3.74 (q, J=7.0 Hz, 2H), 2.56-2.45 (m, 2H), 2.41 (q, J=5.5 Hz, 3H), 1.95 (p, J=6.2 Hz, 2H), 1.36 (t, J=7.0 Hz, 3H).

2): 8-ethoxy-2-methoxy-5,6-dihydroquinazoline (3a)

The solution of compound 2a (21 g, 150.0 mmol) and N,N-dimethylformamide dimethylacetal (99.3 mL, 750.0 mol, 5 equiv.) in N,N-dimethylformamide (300 mL) was stirred at 120° C. for 13 hours. After the mixture was cooled to room temperature, the brown oily product obtained by vacuum concentration was enamine intermediate. The crude product can be directly used in the next reaction without further purification. LC-MS (ESI), $C_{13}H_{20}N_3O$ [M+H]$^+$: m/z=234.2.

The crude product obtained in the above step, O-methylisourea sulfate (73.9 g, 300.0 mmol) and anhydrous sodium acetate (49.2 g, 600.0 mmol) were suspended in N,N-dimethylformamide (500 ml). The temperature of the mixture was raised to 80° C. and the reaction was continued for 24 hours. After the mixture was cooled to room temperature, the mixture was diluted with dichloromethane (500 mL), suction filtered, and concentrated. The resulting residue was purified by flash silica gel column chromatography (petroleum ether/ethyl acetate=1:1) to afford light yellow solid product which was the title compound 3a (16.4 g, 79.5 mmol, 53%). 1H NMR (400 MHz, chloroform-d, ppm) δ 8.20 (s, 1H), 5.46 (t, J=4.7 Hz, 1H), 3.99 (s, 3H), 3.92 (q, J=7.0 Hz, 2H), 2.70 (t, J=7.9 Hz, 2H), 2.40 (td, J=7.9, 4.8 Hz, 2H), 1.44 (t, J=7.0 Hz, 3H).

3): 2-methoxy-6,7-dihydroquinazolin-8(5H)-one (4a)

In an ice-water bath, hydrogen chloride (37.5 mL, 4M in dioxane, 150 mmol) was slowly added to the solution of compound 3a (15 g, 72.8 mmol) in methanol (200 mL). The mixture was heated to room temperature and reacted overnight. In an ice-water bath, saturated aqueous sodium bicarbonate solution was dripped to the mixture until pH≈8. The mixture was extracted three times with dichloromethane (200 mL), and the organic layers were combined, dried (anhydrous sodium sulfate), suction filtered, and concentrated. The resulting light yellow solid product was the title compound 4a (12.0 g, 67.4 mmol, 93%). 1H NMR (400 MHz, chloroform-d, ppm) δ 8.66 (s, 1H), 4.05 (s, 3H), 2.92 (t, J=6.1 Hz, 2H), 2.84-2.72 (m, 2H), 2.18 (ddd, J=12.7, 7.2, 5.7 Hz, 2H).

4): 1-Isopropyl-8-methoxy-4,5-dihydro-1H-[1,2,3]triazolo[4,5-h]quinazoline (6a)

Compound 4a (11.5 g, 64.6 mmol) was dissolved in toluene. Isopropylamine 5a (16.6 mL, 193.8 mmol), 1-azido-4-nitrobenzene (21.2 g, 129.2 mmol) and glacial acetic acid (1.1 mL, 19.4 mmol) were added in order at room temperature. The mixture was heated to 100° C., stirred and reacted overnight. The mixture was cooled to room temperature and concentrated under reduced pressure, and the resulting residue was purified by flash silica gel column chromatography (petroleum ether/ethyl acetate=3:1) to afford a light yellow solid product, which was the title compound 6a (9.2 g, 37.5 mmol, 58%). 1H NMR (400 MHz, chloroform-d, ppm) δ 8.38 (s, 1H), 5.73 (p, J=6.7 Hz, 1H), 4.03 (s, 3H), 3.08 (ddd, J=7.9, 6.6, 1.8 Hz, 2H), 3.05-2.92 (m, 2H), 1.70 (d, J=6.7 Hz, 6H).

5): 1-Isopropyl-8-methoxy-1H-[1,2,3]triazolo[4,5-h]quinazoline (7a)

2,3-Dichloro-5,6-dicyano-1,4-benzoquinone (23.6 g, 104.1 mmol) was added to the solution of compound 6a (8.5 g, 34.7 mmol) in toluene (200 mL), and the mixture was heated to 50° C. and reacted for 24 hours. The mixture was concentrated under reduced pressure, and the resulting residue was purified by flash silica gel column chromatography (petroleum ether/ethyl acetate=20:1 to 6:1) to afford a light yellow solid product, which was the title compound 7a (6.4 g, 26.4 mmol, 76%). 1H NMR (400 MHz, chloroform-d, ppm) δ 9.32 (s, 1H), 8.00 (d, J=8.8 Hz, 1H), 7.68 (d, J=8.9 Hz, 1H), 6.15 (p, J=6.7 Hz, 1H), 4.21 (s, 3H), 1.87 (d, J=6.8 Hz, 6H).

6): 8-Chloro-1-isopropyl-TH-[1,2,3]triazolo[4,5-h]quinazoline (8a)

In an ice-water bath, phosphorus oxychloride (22.3 mL, 239.0 mmol) was slowly dripped to the solution of compound 7a (5.8 g, 23.9 mmol) in N,N-dimethylformamide (200 mL). After dripping, the mixture was heated to 100° C. and reacted for 1 hour. The reaction was moved to an ice-water bath again, and diluted with ethyl acetate (600 mL). Sodium hydroxide aqueous solution (1M) was slowly dripped under vigorous stirring to adjust pH to about 8. The organic phase was separated, washed three times with water (80 mL) and once with saturated brine (80 mL), dried (anhydrous sodium sulfate), suction filtered, and concentrated, and the resulting residue was purified by flash silica gel column chromatography (petroleum ether/ethyl acetate=4:1) to afford a light yellow solid product, which was the title compound 8a (4.7 g, 19.1 mmol). 1H NMR (400 MHz, chloroform-d, ppm) δ 9.39 (s, 1H), 8.21 (dd, J=8.9, 0.8 Hz, 1H), 7.76 (dd, J=8.9, 0.9 Hz, 1H), 6.14 (p, J=6.7 Hz, 1H), 1.94-1.80 (m, 6H).

7): Tert-butyl 4-(6-((1-isopropyl-1H-[1,2,3]triazolo[4,5-h]quinazolin-8-yl)amino) pyridin-3-yl)piperazine-1-carboxylate (I-1a)

Lithium bistrimethylsilylamide (0.606 mL, 1M in THF, LiHMDS) was slowly dripped to the solution of tert butyl 4-(6-aminopyridine-3-yl) piperazine-1-carboxylate 9a (168.6 mg, 0.606 mmol) in toluene (0.8 mL). After the mixture was reacted and stirred at room temperature for 30 minutes, compound 8a (50 mg, 0.202 mmol) was added, and the reaction was continued to stir for 4 hours. Saturated aqueous sodium bicarbonate solution (5 mL) was added to quench the reaction. The mixture was extracted with dichloromethane (8 mL) for 3 times, and the organic layers were combined, dried (anhydrous sodium sulfate), suction filtered, and concentrated. The resulting residue was purified by flash silica gel column chromatography (dichloromethane/methanol=30:1) to afford a light yellow solid product, which was the title compound I-1a (56 mg, 0.114 mmol, 56.4%). $^1$H NMR (400 MHz, chloroform-d, ppm) δ 9.23 (s, 1H), 8.46 (s, 1H), 8.33 (d, J=9.0 Hz, 1H), 8.11 (s, 1H), 7.89 (d, J=8.8 Hz, 1H), 7.59 (d, J=8.8 Hz, 1H), 7.37 (dd, J=9.1, 2.9 Hz, 1H), 6.20 (p, J=6.7 Hz, 1H), 3.64 (t, J=5.1 Hz, 4H), 3.14 (d, J=5.2 Hz, 4H), 1.86 (d, J=6.7 Hz, 6H), 1.50 (s, 9H).

8): 1-Isopropyl-N-(5-(piperazin-1-yl)pyridin-2-yl)-1H-[1,2,3]triazolo[4,5-h]quinazolin-8-amine hydrochloride (I-1)

Compound I-1a (14.7 mg, 0.03 mmol) was dissolved in dichloromethane (2 mL), and the solution of hydrogen chloride in 1,4-dioxane (4 M, 0.76 mL) was added. After the mixture was stirred at room temperature for 2 hours, the mixture was suction filtered. The resulting filter residue was vacuum-dried by an oil pump to constant weight, and the resulting yellow powder was the title compound I-1 (12.6 mg, 99%).

TABLE 1

Examples I-2 to I-17

| Compound No. | Chemical structure | Chemical name | LC-MS (ESI) [M + H]$^+$ |
|---|---|---|---|
| I-2 | 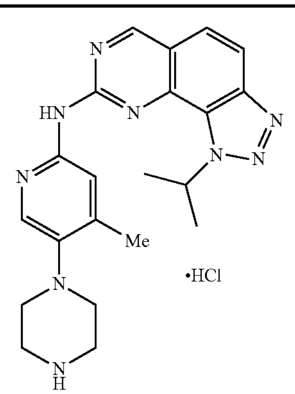 | 1-Isopropyl-N-(4-methyl-5-(piperazin-1-yl)pyridin-2-yl)-1H-[1,2,3]triazolo[4,5-h]quinazolin-8-amine hydrochloride | 404.2 |
| I-3 | 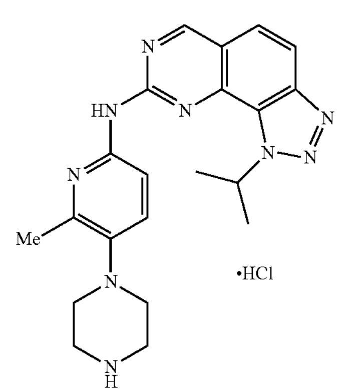 [SMILES: Cc1nc(Nc2ncc3ccc4nnn(C(C)C)c4c3n2)ccc1N1CCNCC1 ; Cl] | 1-Isopropyl-N-(6-methyl-5-(piperazin-1-yl)pyridin-2-yl)-1H-[1,2,3]triazolo[4,5-h]quinazolin-8-amine hydrochloride | 404.2 |

TABLE 1-continued

Examples I-2 to I-17

| Compound No. | Chemical structure | Chemical name | LC-MS (ESI) [M + H]⁺ |
| --- | --- | --- | --- |
| I-4 | 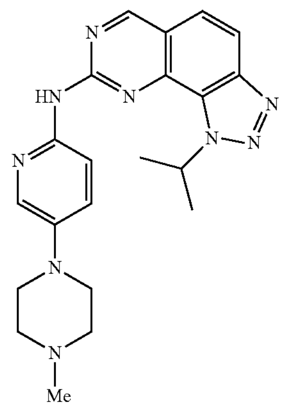 [SMILES: CC(C)n1nnc2ccc3cnc(Nc4ccc(N5CCN(C)CC5)cn4)nc3c21] | 1-Isopropyl-N-(5-(4-methylpiperazin-1-yl)pyridin-2-yl)-1H-[1,2,3]triazolo[4,5-h]quinazolin-8-amine hydrochloride | 404.1 |
| I-5 | 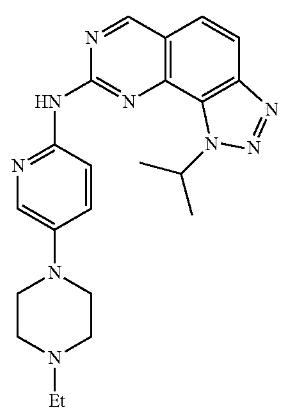 [SMILES: CCN1CCN(c2ccc(Nc3ncc4ccc5nnn(C(C)C)c5c4n3)nc2)CC1] | N-(5-(4-Ethylpiperazin-1-yl)pyridin-2-yl)-1-isopropyl-1H-[1,2,3]triazolo[4,5-h]quinazolin-8-amine hydrochloride | 418.2 |
| I-6 | 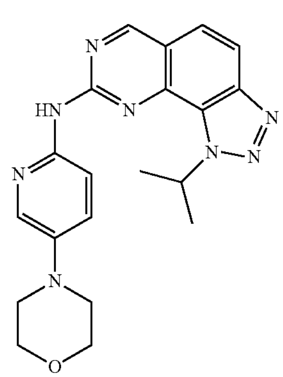 [SMILES: CC(C)n1nnc2ccc3cnc(Nc4ccc(N5CCOCC5)cn4)nc3c21] | 1-Isopropyl-N-(5-morpholinopyridin-2-yl)-1H-[1,2,3]triazolo[4,5-h]quinazolin-8-amine hydrochloride | 391.2 |

TABLE 1-continued

Examples I-2 to I-17

| Compound No. | Chemical structure | Chemical name | LC-MS (ESI) [M + H]⁺ |
|---|---|---|---|
| I-7 | 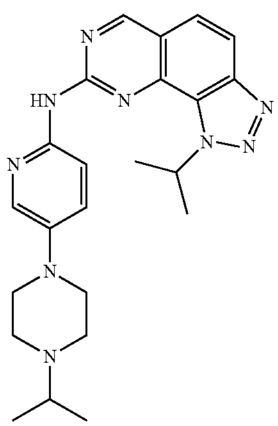 [SMILES: CC(C)N1CCN(c2ccc(Nc3ncc4ccc5nnn(C(C)C)c5c4n3)nc2)CC1] | 1-Isopropyl-N-(5-(4-isopropylpiperazin-1-yl)pyridin-2-yl)-1H-[1,2,3]triazolo[4,5-h]quinazolin-8-amine hydrochloride | 432.3 |
| I-8 | 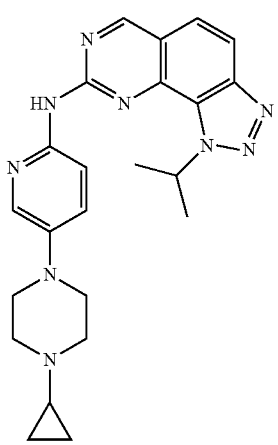 [SMILES: CC(C)n1nnc2ccc3cnc(Nc4ccc(N5CCN(C6CC6)CC5)cn4)nc3c21] | N-(5-(4-Cyclopropylpiperazin-1-yl)pyridin-2-yl)-1-isopropyl-1H-[1,2,3]triazolo[4,5-h]quinazolin-8-amine hydrochloride | 430.2 |
| I-9 | 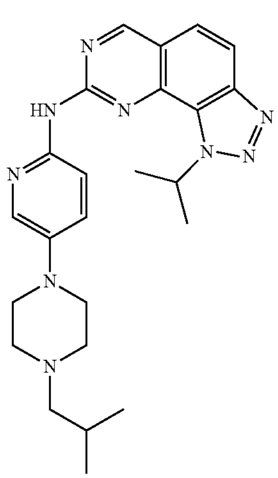 [SMILES: CC(C)CN1CCN(c2ccc(Nc3ncc4ccc5nnn(C(C)C)c5c4n3)nc2)CC1] | N-(5-(4-Isobutylpiperazin-1-yl)pyridin-2-yl)-1-isopropyl-1H-[1,2,3]triazolo[4,5-h]quinazolin-8-amine hydrochloride | 446.1 |

TABLE 1-continued

Examples I-2 to I-17

| Compound No. | Chemical structure | Chemical name | LC-MS (ESI) [M + H]+ |
|---|---|---|---|
| I-10 | 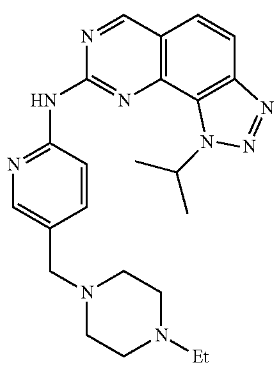 [SMILES: CCN1CCN(Cc2ccc(Nc3ncc4ccc5nnn(C(C)C)c5c4n3)nc2)CC1] | N-(5-((4-Ethylpiperazin-1-yl)methyl)pyridin-2-yl)-1-isopropyl-1H-[1,2,3]triazolo[4,5-h]quinazolin-8-amine hydrochloride | 432.2 |
| I-11 | 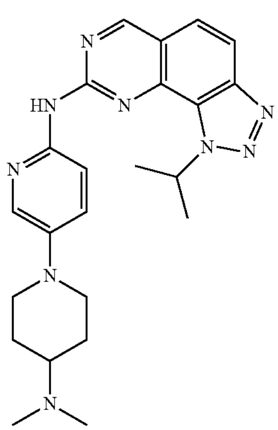 [SMILES: CC(C)n1nnc2ccc3cnc(Nc4ccc(N5CCC(N(C)C)CC5)cn4)nc3c21] | N-(5-(4-(Dimethylamino)piperidin-1-yl)pyridin-2-yl)-1-isopropyl-1H-[1,2,3]triazolo[4,5-h]quinazolin-8-amine hydrochloride | 432.2 |
| I-12 | 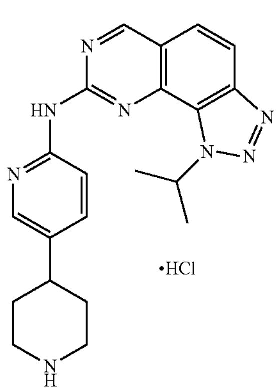 [SMILES: CC(C)n1nnc2ccc3cnc(Nc4ccc(C5CCNCC5)cn4)nc3c21 ; Cl] | 1-Isopropyl-N-(5-(piperidin-4-yl)pyridin-2-yl)-1H-[1,2,3]triazolo[4,5-h]quinazolin-8-amine hydrochloride | 389.1 |

TABLE 1-continued

Examples I-2 to I-17

| Compound No. | Chemical structure | Chemical name | LC-MS (ESI) [M + H]+ |
|---|---|---|---|
| I-13 | 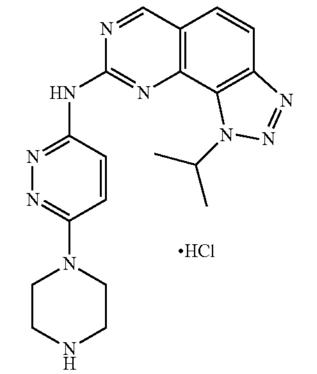 [SMILES: CC(C)n1nnc2ccc3cnc(Nc4ccc(N5CCNCC5)nn4)nc3c21 ; Cl] | 1-Isopropyl-N-(6-(piperazin-1-yl)pyridazin-3-yl)-1H-[1,2,3]triazolo[4,5-h]quinazolin-8-amine hydrochloride | 391.2 |
| I-14 | 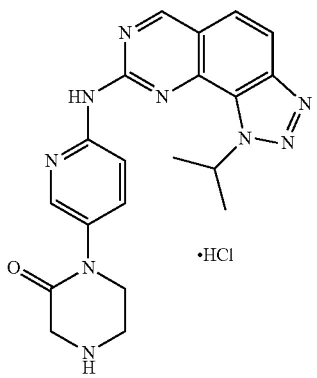 [SMILES: CC(C)n1nnc2ccc3cnc(Nc4ccc(N5CCNCC5=O)cn4)nc3c21 ; Cl] | 1-(6-((1-Isopropyl-1H-[1,2,3]triazolo[4,5-h]quinazolin-8-yl)amino)pyridin-3-yl)piperazin-2-one hydrochloride | 404.2 |
| I-15 | 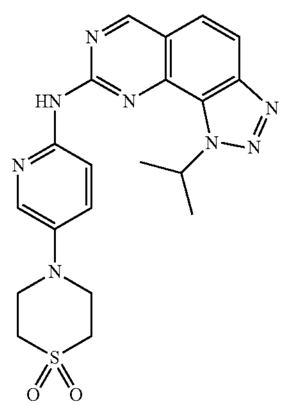 [SMILES: CC(C)n1nnc2ccc3cnc(Nc4ccc(N5CCS(=O)(=O)CC5)cn4)nc3c21] | 4-(6-((1-Isopropyl-1H-[1,2,3]triazolo[4,5-h]quinazolin-8-yl)amino)pyridin-3-yl)thiomorpholine 1,1-dioxide hydrochloride | 439.2 |
| I-16 | 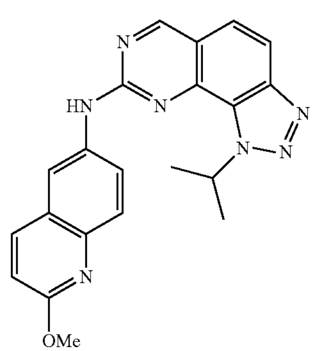 [SMILES: COc1ccc2cc(Nc3ncc4ccc5nnn(C(C)C)c5c4n3)ccc2n1] | 1-Isopropyl-N-(2-methoxyquinolin-6-yl)-1H-[1,2,3]triazolo[4,5-h]quinazolin-8-amine hydrochloride | 386.1 |

| Compound No. | Chemical structure | Chemical name | LC-MS (ESI) [M + H]+ |
|---|---|---|---|
| I-17 | 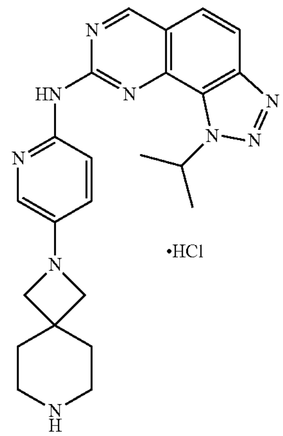 [SMILES: CC(C)n1nnc2ccc3cnc(Nc4ccc(N5CC6(CCNCC6)C5)cn4)nc3c21 ; Cl] | N-(5-(2,7-Diazaspiro[3.5]nonan-2-yl)pyridin-2-yl)-1-isopropyl-1H-[1,2,3]triazolo[4,5-h]quinazolin-8-amine hydrochloride | 430.2 |

Compound I-2 (45.2 mg, 103.0 μmmol, 51%), 1-3 (40.8 mg, 92.9 μmmol, 46%), 1-12 (61.7 mg, 145.4 μmmol, 72%), 1-13 (56.8 mg, 133.3 μmmol, 66%), 1-14 (29.3 mg, 66.7 μmmol, 33%), and I-17 (28.9 mg, 54.5 μmmol, 27%) were prepared from compound 8a (50 mg, 0.202 mmol) by referring to the synthesis method of I-1 in Example 1;

Compound I-4 (55.4 mg, 137.4 μmmol, 68%), I-5 (68.3 mg, 163.6 μmmol, 81%), I-6 (60.6 mg, 155.5 μmmol, 77%), I-7 (62.7 mg, 145.4 μmmol, 72%), I-8 (59.8 mg, 139.4 μmmol, 69%), 1-9 (71.1 mg, 159.6 μmmol, 79%), 1-10 (61.8 mg, 143.4 μmmol, 71%), 1-11 (35.7 mg, 82.8 μmmol, 41%), 1-15 (23.0 mg, 52.5 μmmol, 26%) and I-16 (55.2 mg, 143.4 μmmol, 71%) were prepared from compound 8a (50 mg, 0.202 mmol) by referring to the synthesis method of I-1a in Example 1.

I-2a 1H NMR (400 MHz, chloroform-d, ppm) δ 9.24 (s, 1H), 8.37 (s, 1H), 8.26 (s, 1H), 8.06 (s, 1H), 7.91 (d, J=8.8 Hz, 1H), 7.60 (d, J=8.8 Hz, 1H), 6.26 (p, J=6.7 Hz, 1H), 3.61 (t, J=5.0 Hz, 4H), 2.95 (t, J=5.0 Hz, 4H), 2.55-2.38 (m, 3H), 1.87 (d, J=6.7 Hz, 6H), 1.50 (s, 9H).

I-3a 1H NMR (400 MHz, chloroform-d, ppm) δ 9.21 (s, 1H), 8.20 (d, J=8.7 Hz, 1H), 8.06 (s, 1H), 7.89 (d, J=8.8 Hz, 1H), 7.59 (d, J=8.8 Hz, 1H), 7.40 (d, J=8.7 Hz, 1H), 6.21 (p, J=6.7 Hz, 1H), 3.61 (t, J=5.0 Hz, 4H), 2.88 (t, J=5.0 Hz, 4H), 2.53 (s, 3H), 1.86 (d, J=6.7 Hz, 6H), 1.50 (s, 9H).

I-4 1H NMR (400 MHz, chloroform-d, ppm) δ 9.20 (s, 1H), 8.31-8.27 (m, 1H), 8.17 (s, 1H), 8.09 (d, J=3.0 Hz, 1H), 7.88 (d, J=8.8 Hz, 1H), 7.58 (d, J=8.8 Hz, 1H), 7.36 (dd, J=9.0, 3.0 Hz, 1H), 6.21 (p, J=6.7 Hz, 1H), 3.24 (dd, J=6.1, 3.8 Hz, 4H), 2.64 (t, J=5.0 Hz, 4H), 2.39 (s, 3H), 1.86 (d, J=6.7 Hz, 6H).

I-5 1H NMR (400 MHz, chloroform-d, ppm) δ 9.24 (s, 1H), 8.69 (s, 1H), 8.30 (d, J=9.0 Hz, 1H), 8.13 (s, 1H), 7.87 (d, J=8.8 Hz, 1H), 7.58 (d, J=8.8 Hz, 1H), 7.36 (dd, J=9.0, 3.0 Hz, 1H), 6.21 (p, J=6.7 Hz, 1H), 3.26 (t, J=5.0 Hz, 4H), 2.68 (t, J=4.9 Hz, 4H), 2.52 (q, J=7.2 Hz, 2H), 1.86 (d, J=6.7 Hz, 6H), 1.16 (t, J=7.2 Hz, 3H).

I-6 1H NMR (400 MHz, chloroform-d, ppm) δ 9.22 (s, 1H), 8.39 (s, 1H), 8.33 (d, J=8.9 Hz, 1H), 8.08 (d, J=2.8 Hz, 1H), 7.88 (d, J=8.8 Hz, 1H), 7.59 (d, J=8.8 Hz, 1H), 7.35 (dd, J=9.1, 3.0 Hz, 1H), 6.21 (p, J=6.8 Hz, 1H), 3.96-3.88 (m, 4H), 3.22-3.16 (m, 4H), 1.86 (d, J=6.7 Hz, 6H).

I-7 1H NMR (400 MHz, chloroform-d, ppm) δ 9.19 (s, 1H), 8.28 (d, J=9.0 Hz, 1H), 8.10-8.02 (m, 2H), 7.87 (d, J=8.8 Hz, 1H), 7.58 (d, J=8.8 Hz, 1H), 7.36 (dd, J=9.1, 3.0 Hz, 1H), 6.21 (p, J=6.7 Hz, 1H), 3.24 (s, 4H), 2.75 (s, 5H), 1.86 (d, J=6.7 Hz, 6H), 1.12 (d, J=6.5 Hz, 6H).

I-8 1H NMR (400 MHz, chloroform-d, ppm) δ 9.20 (s, 1H), 8.27 (d, J=9.0 Hz, 1H), 8.13-8.05 (m, 2H), 7.87 (d, J=8.8 Hz, 1H), 7.58 (d, J=8.8 Hz, 1H), 7.36 (dd, J=9.0, 3.0 Hz, 1H), 6.20 (q, J=6.7 Hz, 1H), 3.19 (t, J=5.1 Hz, 4H), 2.83 (t, J=5.0 Hz, 4H), 1.86 (d, J=6.7 Hz, 6H), 1.72 (d, J=8.6 Hz, 1H), 0.55-0.42 (m, 4H).

I-9 1H NMR (400 MHz, chloroform-d, ppm) δ 9.20 (s, 1H), 8.27 (d, J=9.0 Hz, 1H), 8.14 (s, 1H), 8.08 (d, J=2.9 Hz, 1H), 7.87 (d, J=8.8 Hz, 1H), 7.58 (d, J=8.8 Hz, 1H), 7.36 (dd, J=9.1, 3.0 Hz, 1H), 6.22 (h, J=6.7 Hz, 1H), 3.22 (t, J=5.0 Hz, 4H), 2.61 (t, J=5.0 Hz, 4H), 2.17 (d, J=7.4 Hz, 2H), 1.86 (d, J=6.7 Hz, 7H), 0.94 (d, J=6.6 Hz, 6H).

I-10 1H NMR (400 MHz, chloroform-d, ppm) δ 9.24 (s, 1H), 8.41 (d, J=8.5 Hz, 1H), 8.33-8.26 (m, 1H), 8.23 (s, 1H), 7.92 (d, J=8.8 Hz, 1H), 7.74 (dd, J=8.6, 2.3 Hz, 1H), 7.61 (d, J=8.9 Hz, 1H), 6.21 (p, J=6.7 Hz, 1H), 3.54 (s, 2H), 2.57 (s, 6H), 2.47 (s, 2H), 1.88 (d, J=6.8 Hz, 6H), 1.11 (t, J=7.1 Hz, 3H).

I-11 1H NMR (400 MHz, chloroform-d, ppm) δ 9.20 (s, 1H), 8.27 (d, J=9.0 Hz, 1H), 8.13 (s, 1H), 8.09 (d, J=3.0 Hz, 1H), 7.88 (d, J=8.8 Hz, 1H), 7.58 (d, J=8.8 Hz, 1H), 7.37 (dd, J=9.1, 3.0 Hz, 1H), 6.21 (p, J=6.7 Hz, 1H), 3.69 (d, J=11.8 Hz, 2H), 2.79 (td, J=12.1, 2.5 Hz, 2H), 2.36 (s, 6H), 2.00 (d, J=12.7 Hz, 2H), 1.86 (d, J=6.7 Hz, 6H), 1.73 (td, J=12.0, 3.9 Hz, 2H), 1.68-1.57 (brs, 6H).

I-12a 1H NMR (400 MHz, chloroform-d, ppm) δ 9.25 (s, 1H), 8.39 (d, J=8.6 Hz, 1H), 8.32 (s, 1H), 8.25 (d, J=2.4 Hz, 1H), 7.92 (d, J=8.8 Hz, 1H), 7.63-7.60 (d, J=8.8 Hz 1H), 7.59 (dd, J=8.8 Hz, 2.8 Hz, 1H), 6.21 (p, J=6.7 Hz, 1H), 4.29 (s, 2H), 2.85 (t, J=12.8 Hz, 2H), 2.72 (ddd, J=12.2, 8.5, 3.6 Hz, 1H), 1.88 (d, J=6.7 Hz, 6H), 1.68 (tt, J=12.4, 6.5 Hz, 3H), 1.50 (s, 9H).

I-13a 1H NMR (400 MHz, chloroform-d, ppm) δ 9.23 (s, 1H), 8.47 (d, J=9.8 Hz, 1H), 8.37 (s, 1H), 7.91 (d, J=8.8 Hz, 1H), 7.61 (d, J=8.8 Hz, 1H), 7.08 (d, J=9.8 Hz, 1H), 6.13 (p, J=6.7 Hz, 1H), 3.62 (s, 8H), 1.85 (d, J=6.8 Hz, 6H), 1.50 (s, 9H).

I-14a 1H NMR (400 MHz, chloroform-d, ppm) δ 9.30 (d, J=1.3 Hz, 1H), 8.54 (d, J=8.9 Hz, 1H), 8.33 (d, J=2.6 Hz, 1H), 7.92 (d, J=8.8 Hz, 1H), 7.77 (dt, J=9.0, 1.9 Hz, 1H), 7.69 (dd, J=8.8, 1.5 Hz, 1H), 6.23 (p, J=6.7 Hz, 1H), 4.30 (s, 2H), 3.90-3.82 (m, 4H), 1.88 (d, J=6.7 Hz, 6H), 1.53 (s, 9H).

I-15 $^1$H NMR (400 MHz, chloroform-d, ppm) δ 9.28 (s, 1H), 8.34 (d, J=9.0 Hz, 1H), 8.11 (d, J=3.0 Hz, 1H), 7.86 (d, J=8.8 Hz, 1H), 7.71 (d, J=8.9 Hz, 1H), 7.54 (d, J=3.1 Hz, 1H), 6.25 (p, J=6.7 Hz, 1H), 3.90-3.81 (m, 4H), 3.29-3.22 (m, 4H), 1.88 (d, J=6.7 Hz, 6H).

I-16 $^1$H NMR (400 MHz, chloroform-d, ppm) δ 9.18 (s, 1H), 8.13 (d, J=1.6 Hz, 1H), 7.95 (d, J=8.8 Hz, 1H), 7.91-7.85 (m, 3H), 7.62-7.55 (m, 2H), 6.96 (d, J=8.9 Hz, 1H), 6.25 (p, J=6.7 Hz, 1H), 4.10 (s, 3H), 1.83 (d, J=6.7 Hz, 6H).

I-17a $^1$H NMR (400 MHz, chloroform-d, ppm) 9.16 (s, 1H), 8.19 (t, J=4.4 Hz, 2H), 7.68 (d, J=8.6 Hz, 1H), 7.62 (d, J=2.9 Hz, 1H), 7.52 (d, J=8.7 Hz, 1H), 6.82 (dd, J=8.8, 2.9 Hz, 1H), 6.05 (p, J=6.7 Hz, 1H), 3.71 (s, 4H), 3.40 (d, J=5.8 Hz, 4H), 1.80 (t, J=5.7 Hz, 4H), 1.71 (d, J=6.7 Hz, 6H), 1.45 (s, 9H).

Preparation of Key Intermediate 8-chloro-1-isobutyl-1H-[1,2,3]triazolo[4,5-h]quinazoline (8b)

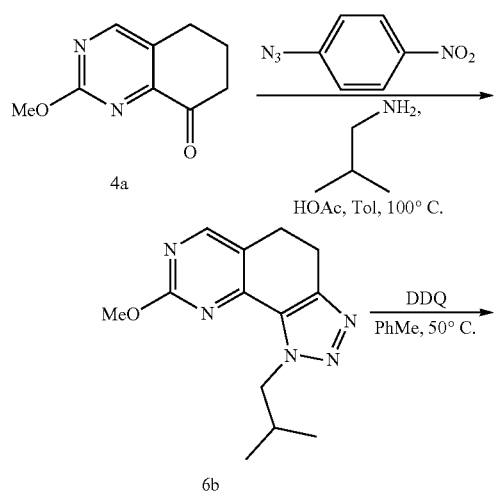

1): 1-Isobutyl-8-methoxy-4,5-dihydro-1H-[1,2,3]triazolo[4,5-h]quinazoline 6b (1.6 g, 6.2 mmol, 61%) was prepared from compound 4a (1.8 g, 10.1 mmol) by referring to the synthesis method of 6a in Example 1. $^1$H NMR (400 MHz, chloroform-d) δ 8.39 (s, 1H), 4.71 (d, J=7.4 Hz, 2H), 4.03 (s, 3H), 3.13-2.98 (m, 4H), 2.40 (dt, J=13.8, 6.9 Hz, 1H), 0.97 (d, J=6.7 Hz, 6H).

2): Compound 7b (1.22 g, 4.76 mmol, 82%) was prepared from compound 6b (1.5 g, 5.80 mmol) by referring to the synthesis method of 7a in Example 1. LC-MS (ESI), $C_{13}H_{15}N_5O$ [M+H]$^+$: m/z=257.2.

3): Compound 8b (600.3 mg, 2.3 mmol, 54%) was prepared from compound 7b (1.1 g, 4.28 mmol) by referring to the synthesis method of 8a in Example 1. 1H NMR (400 MHz, chloroform-d) δ 9.39 (s, 1H), 8.20 (d, J=8.9 Hz, 1H), 7.76 (d, J=8.9 Hz, 1H), 5.07 (d, J=7.2 Hz, 2H), 2.55 (dt, J=13.6, 6.8 Hz, 1H), 1.05 (d, J=6.7 Hz, 6H).

TABLE 2

| | Examples I-18 to I-21 | | |
|---|---|---|---|
| Compound No. | Chemical structure | Chemical name | LC-MS (ESI) [M + H]+ |
| I-18 | (structure shown) ·HCl | 1-Isobutyl-N-(5-(piperazin-1-yl)pyridin-2-yl)-1H-[1,2,3]triazolo[4,5-h]quinazolin-8-amine | 404.2 |

TABLE 2-continued

Examples I-18 to I-21

| Compound No. | Chemical structure | Chemical name | LC-MS (ESI) [M + H]+ |
|---|---|---|---|
| I-19 | 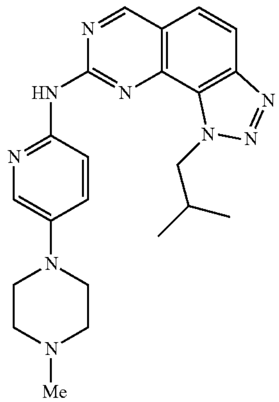 [SMILES: CC(C)Cn1nnc2ccc3cnc(Nc4ccc(N5CCN(C)CC5)cn4)nc3c21] | 1-Isobutyl-N-(5-(4-methylpiperazin-1-yl)pyridin-2-yl)-1H-[1,2,3]triazolo[4,5-h]quinazolin-8-amine hydrochloride | 418.2 |
| I-20 | 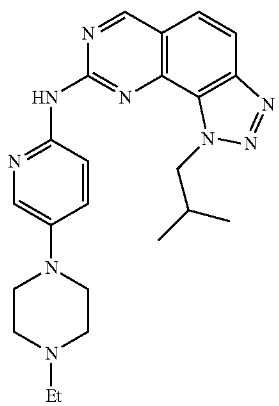 [SMILES: CCN1CCN(c2ccc(Nc3ncc4ccc5nnn(CC(C)C)c5c4n3)nc2)CC1] | N-(5-(4-Ethylpiperazin-1-yl)pyridin-2-yl)-1-isobutyl-1H-[1,2,3]triazolo[4,5-h]quinazolin-8-amine | 432.4 |
| I-21 | 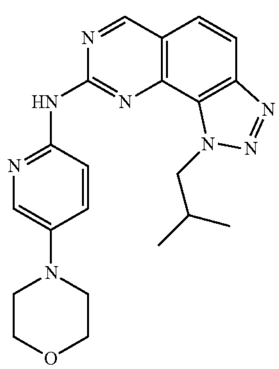 [SMILES: CC(C)Cn1nnc2ccc3cnc(Nc4ccc(N5CCOCC5)cn4)nc3c21] | 1-Isobutyl-N-(5-morpholinopyridin-2-yl)-1H-[1,2,3]triazolo[4,5-h]quinazolin-8-amine | 405.2 |

Compound I-18 (65.8 mg, 149.8 μmmol, 78%) was prepared from compound 8b (50 mg, 0.192 mmol) by referring to the synthesis method of I-1 in Example 1;

Compound I-19 (54.5 mg, 130.6 μmmol, 68%), 1-20 (67.1 mg, 155.5 μmmol, 81%), and 1-21 (57.4 mg, 142.1 μmmol, 740%) were prepared from compound 8b (50 mg, 0.192 mmol) by referring to the synthesis method of I-1a in Example 1.

I-18a $^1$H NMR (400 MHz, chloroform-d) δ 9.21 (s, 1H), 8.30 (d, J=9.0 Hz, 1H), 8.14 (s, 1H), 8.08 (d, J=2.9 Hz, 1H), 7.89 (d, J=8.9 Hz, 1H), 7.59 (d, J=8.8 Hz, 1H), 7.40 (dd, J=9.0, 3.0 Hz, 1H), 5.10 (d, J=7.6 Hz, 2H), 3.67-3.61 (m, 3H), 3.14 (t, J=5.0 Hz, 4H), 1.50 (s, 9H), 0.97 (d, J=6.6 Hz, 6H).

I-19 $^1$H NMR (400 MHz, chloroform-d) δ 9.21 (s, 1H), 8.34 (s, 1H), 8.27 (d, J=9.0 Hz, 1H), 8.11 (d, J=3.0 Hz, 1H), 7.87 (d, J=8.8 Hz, 1H), 7.59 (d, J=8.8 Hz, 1H), 7.39 (dd, J=9.0, 3.0 Hz, 1H), 5.10 (d, J=7.6 Hz, 2H), 3.28-3.19 (m, 4H), 2.68-2.60 (m, 4H), 2.57 (dd, J=13.8, 6.9 Hz, 1H), 2.38 (s, 3H), 0.96 (d, J=6.7 Hz, 6H).

I-20 $^1$H NMR (400 MHz, chloroform-d) δ 9.21 (s, 1H), 8.35 (s, 1H), 8.28-8.23 (m, 1H), 8.12 (d, J=2.9 Hz, 1H), 7.87 (d, J=8.8 Hz, 1H), 7.58 (d, J=8.8 Hz, 1H), 7.39 (dd, J=9.0, 3.0 Hz, 1H), 5.09 (d, J=7.6 Hz, 2H), 3.27-3.21 (m, 4H), 2.71-2.63 (m, 4H), 2.54 (dq, J=17.7, 7.0 Hz, 3H), 1.67 (s, 3H), 1.15 (t, J=7.2 Hz, 3H), 0.96 (d, J=6.7 Hz, 6H).

I-21 ¹H NMR (400 MHz, chloroform-d) δ 9.20 (s, 1H), 8.29 (d, J=8.9 Hz, 1H), 8.11-8.06 (m, 2H), 7.88 (d, J=8.8 Hz, 1H), 7.59 (d, J=8.9 Hz, 1H), 7.38 (dd, J=9.0, 3.1 Hz, 1H), 5.10 (d, J=7.6 Hz, 2H), 3.95-3.88 (m, 4H), 3.23-3.13 (m, 4H), 0.97 (d, J=6.7 Hz, 6H).

Preparation of Intermediate 8-chloro-1-cyclopentyl-1H-[1,2,3]triazolo[4,5-h]quinazoline (8c)

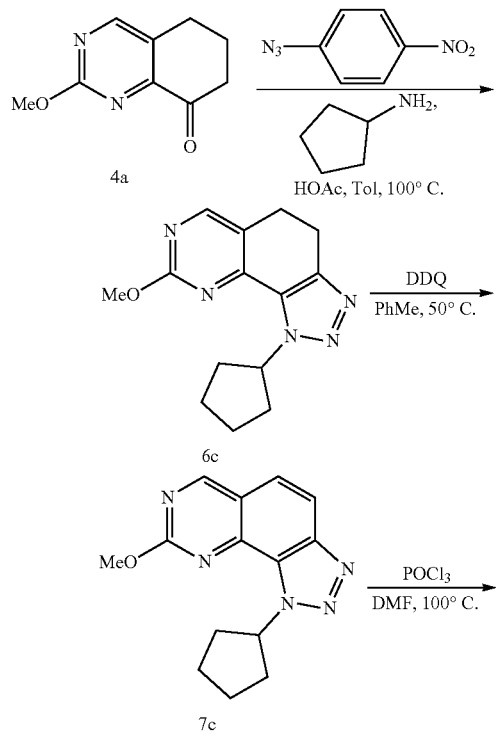

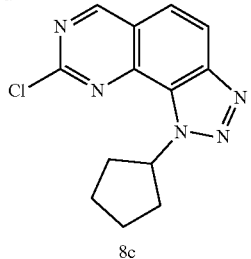

1): 1-Cyclopentyl-8-methoxy-4,5-dihydro-1H-[1,2,3]triazolo[4,5-h]quinazoline 6c (1.06 g, 3.91 mmol, 58%) was prepared from compound 4a (1.2 g, 6.74 mmol) by referring to the synthesis method of 6a in Example 1. ¹H NMR (400 MHz, chloroform-d) δ 8.46 (s, 1H), 4.68 (d, J=7.4 Hz, 2H), 3.92 (s, 3H), 3.15-2.88 (m, 4H), 2.42 (dq, J=13.2, 6.4 Hz, 2H), 2.32 (m, 1H), 2.10 (td, J=13.2, 6.4 Hz, 2H), 1.88 (d, J=8.0 Hz, 4H).

2): Compound 7c (705 mg, 2.62 mmol, 71%) was prepared from compound 6c (1.0 g, 3.69 mmol) by referring to the synthesis method of 7a in Example 1. LC-MS (ESI), $C_{14}H_{16}N_5O$ [M+H]⁺: m/z=270.1.

3): Compound 8c (350.5 mg, 1.28 mmol, 49%) was prepared from compound 7c (705 mg, 2.62 mmol) by referring to the synthesis method of 8a in Example 1. 1H NMR (400 MHz, chloroform-d) δ 9.41 (s, 1H), 8.32 (s, 1H), 8.18 (d, J=8.7 Hz, 1H), 7.78 (d, J=8.7 Hz, 1H), 6.05 (p, J=6.7 Hz, 1H), 2.48 (dq, J=13.3, 6.6 Hz, 2H), 2.06 (td, J=13.8, 6.8 Hz, 2H), 1.91 (d, J=8.1 Hz, 4H).

TABLE 3

| | Examples I-22 and I-23 | | |
|---|---|---|---|
| Compound No. | Chemical structure | Chemical name | LC-MS (ESI) [M + H]⁺ |
| I-22 | (structure) | 1-Cyclopentyl-N-(5-(piperazin-1-yl)pyridin-2-yl)-1H-[1,2,3]triazolo[4,5-h]quinazolin-8-amine hydrochloride | 416.3 |

TABLE 3-continued

Examples I-22 and I-23

| Compound No. | Chemical structure | Chemical name | LC-MS (ESI) [M + H]+ |
|---|---|---|---|
| I-23 | 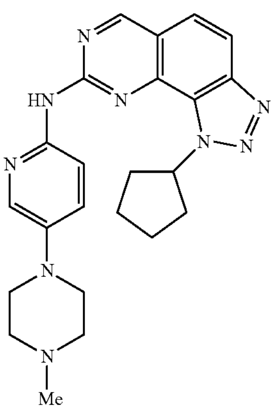 [SMILES: CN1CCN(c2ccc(Nc3ncc4ccc5nnn(C6CCCC6)c5c4n3)nc2)CC1] | 1-Cyclopentyl-N-(5-(4-methylpiperazin-1-yl)pyridin-2-yl)-1H-[1,2,3]triazolo[4,5-h]quinazolin-8-amine | 430.2 |

Compound I-22 (27.7 mg, 61.4 μmmol, 48%) was prepared from compound 8c (35 mg, 0.128 mmol) by referring to the synthesis method of I-1 in Example 1;

Compound I-23 (22.5 mg, 52.5 μmmol, 41%) was prepared from compound 8c (35 mg, 0.128 mmol) by referring to the synthesis method of I-1a in Example 1.

I-22a 1H NMR (400 MHz, chloroform-d) δ 9.35 (s, 1H), 8.26 (d, J=9.6 Hz, 1H), 8.10-7.92 (m, 2H), 7.82 (d, J=8.8 Hz, 1H), 7.72 (d, J=9.5 Hz, 1H), 6.13 (p, J=7.1 Hz, 1H), 3.53-3.41 (m, 4H), 3.52-3.43 (m, 4H), 2.48 (dt, J=12.2, 6.0 Hz, 2H), 2.12-2.02 (m, 2H), 2.10-1.96 (m, 4H), 1.48 (s, 9H).

I-23 $^1$H NMR (400 MHz, chloroform-d) δ 9.16 (s, 1H), 8.32 (d, J=9.0 Hz, 1H), 8.12 (s, 1H), 8.06 (d, J=2.9 Hz, 1H), 7.68 (d, J=8.7 Hz, 1H), 7.44 (d, J=8.6 Hz, 1H), 7.28 (dd, J=9.1, 3.0 Hz, 1H), 6.05 (p, J=7.0 Hz, 1H), 4.01 (dd, J=5.8, 3.7 Hz, 4H), 3.12 (dd, J=5.8, 3.7 Hz, 4H), 2.44 (dt, J=13.8, 7.3 Hz, 2H), 2.36 (s, 3H), 2.15-1.99 (m, 4H), 1.85 (dq, J=9.9, 3.9 Hz, 2H).

Example 1-24

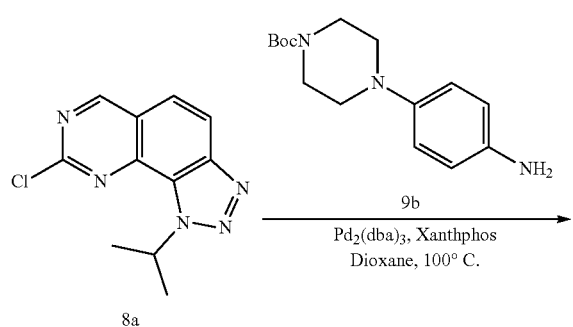

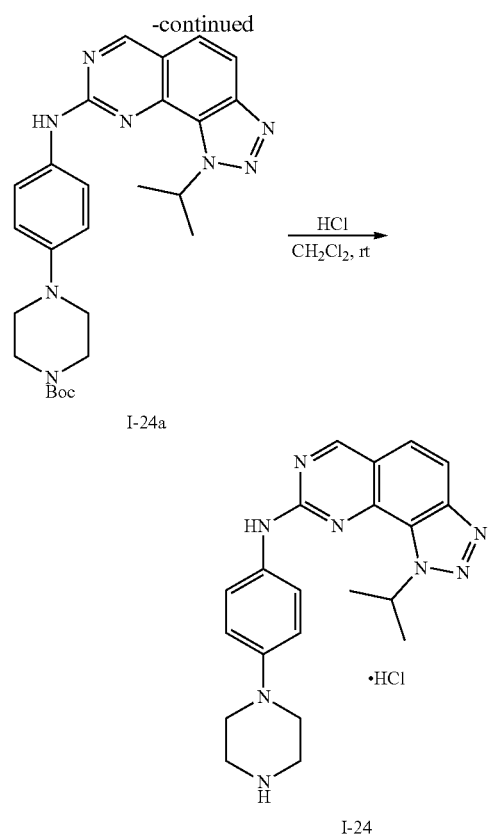

1): Preparation of tert-butyl 4-(4-((1-isopropyl-1H-[1,2,3]triazolo[4,5-h]quinazolin-8-yl)amino)phenyl)piperazine-1-carboxylate (I-24a)

At room temperature, tris(dibenzylideneacetone)dipalladium (7.0 mg, 10 mol %) and 4,5-bisdiphenylphosphine-9,9-dimethylxanthene (14 mg, 0.024 mmol) were added to the solution of compound 8a (30 mg, 0.121 mmol) and 9b (67.1 mg, 0.242 mmol) in 1,4-dioxane (1.5 mL). After adding, the reaction was replaced with argon twice, the mixture was heated to 100° C. and reacted in a sealed tube for 4 hours. After the mixture was cooled to room temperature, ethyl acetate (5 mL) and half-saturated aqueous sodium bicarbonate solution (8 mL) were added to dilute the mixture. Organic layer was separated, and the aqueous layer was extracted with ethyl acetate (5 ml) for 3 times. The organic layers were combined, washed with saturated brine (5 mL), anhydrous sodium sulfate dried, suction filtered, and concentrated. The resulting residue was purified by flash silica gel column chromatography (dichloromethane/methanol=100:1 to 30:1) to afford a light yellow solid product, which was the title compound I-24a (16.1 mg, 0.033 mmol). $^1$H NMR (400 MHz, chloroform-d, ppm) δ 9.10 (s, 1H), 7.81 (d, J=8.8 Hz, 1H), 7.66-7.56 (m, 2H), 7.52 (d, J=8.9 Hz, 1H), 7.42 (s, 1H), 7.05-6.92 (m, 2H), 6.16 (p, J=6.7 Hz, 1H), 3.62 (t, J=5.1 Hz, 4H), 3.14 (t, J=5.1 Hz, 4H), 1.79 (d, J=6.7 Hz, 6H), 1.50 (s, 9H).

2): Preparation of 1-isopropyl-N-(4-(piperazin-1-yl)phenyl)-1H-[1,2,3]triazolo[4,5-h]quinazolin-8-amine hydrochloride (1-24)

Compound I-24a (12.2 mg, 0.025 mmol) was dissolved in dichloromethane (2 mL), and the solution of hydrogen chloride in 1,4-dioxane (4 M, 0.13 mL) was added. After being stirred at room temperature for 2 hours, the mixture was suction filtered. The resulting filter residue was vacuum-dried by an oil pump to constant weight, and the resulting yellow powder was the title compound I-24 (13.1 mg). LC-MS (ESI), $C_{21}H_{25}N_8$ [M+H]$^+$: m/z=389.2.

TABLE 4

Examples I-25 to I-35

| Compound No. | Chemical structure | Chemical name | LC-MS (ESI) [M + H]$^+$ |
|---|---|---|---|
| I-25 | 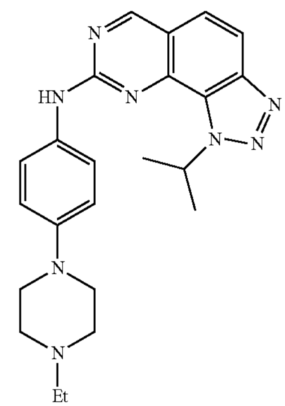 [SMILES: CCN1CCN(c2ccc(Nc3ncc4ccc5nnn(C(C)C)c5c4n3)cc2)CC1] | N-(4-(4-Ethylpiperazin-1-yl)phenyl)-1-isopropyl-1H-[1,2,3]triazolo[4,5-h]quinazolin-8-amine | 417.2 |
| I-26 | 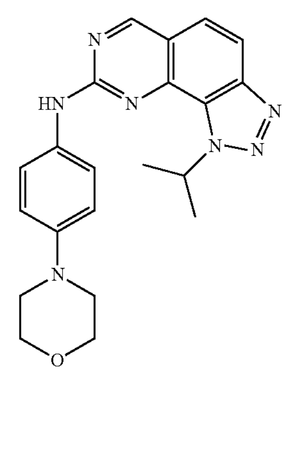 [SMILES: CC(C)n1nnc2ccc3cnc(Nc4ccc(N5CCOCC5)cc4)nc3c21] | 1-Isopropyl-N-(4-morpholinophenyl)-1H-[1,2,3]triazolo[4,5-h]quinazolin-8-amine | 390.2 |

TABLE 4-continued

Examples I-25 to I-35

| Compound No. | Chemical structure | Chemical name | LC-MS (ESI) [M + H]+ |
|---|---|---|---|
| I-27 | 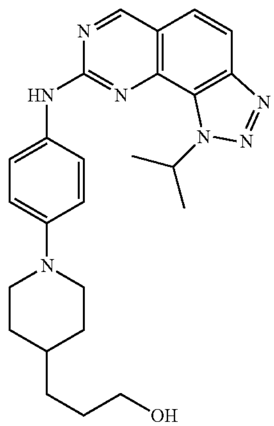 [SMILES: CC(C)n1nnc2ccc3cnc(Nc4ccc(N5CCC(CCCO)CC5)cc4)nc3c21] | 3-(1-(4-((1-isopropyl-1H-[1,2,3]triazolo[4,5-h]quinazolin-8-yl)amino)phenyl)piperidin-4-yl)propan-1-ol | 446.2 |
| I-28 | 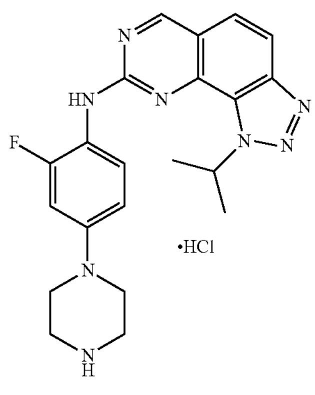 [SMILES: CC(C)n1nnc2ccc3cnc(Nc4ccc(N5CCNCC5)cc4F)nc3c21 ; Cl] | N-(2-Fluoro-4-(piperazin-1-yl)phenyl)-1-isopropyl-1H-[1,2,3]triazolo[4,5-h]quinazolin-8-amine hydrochloride | 407.2 |
| I-29 | 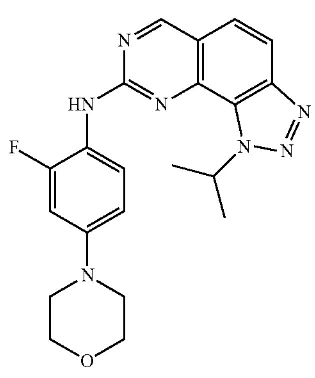 [SMILES: CC(C)n1nnc2ccc3cnc(Nc4ccc(N5CCOCC5)cc4F)nc3c21] | N-(2-Fluoro-4-morpholinophenyl)-1-isopropyl-1H-[1,2,3]triazolo[4,5-h]quinazolin-8-amine | 408.1 |

TABLE 4-continued
Examples I-25 to I-35
| Compound No. | Chemical structure | Chemical name | LC-MS (ESI) [M + H]⁺ |
|---|---|---|---|
| I-30 | 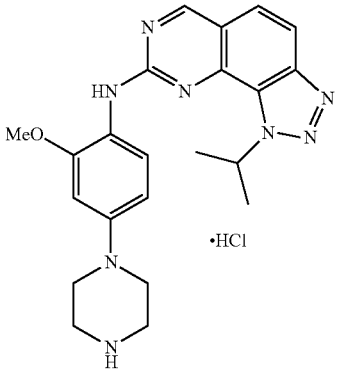 [SMILES: COc1cc(N2CCNCC2)ccc1Nc1ncc2ccc3nnn(C(C)C)c3c2n1 ; Cl] | 1-Isopropyl-N-(2-methoxy-4-(piperazin-1-yl)phenyl)-1H-[1,2,3]triazolo[4,5-h]quinazolin-8-amine hydrochloride | 419.1 |
| I-31 | 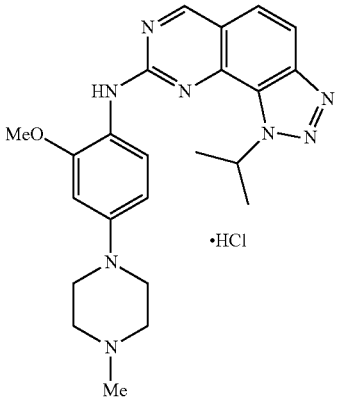 [SMILES: COc1cc(N2CCN(C)CC2)ccc1Nc1ncc2ccc3nnn(C(C)C)c3c2n1 ; Cl] | 1-Isopropyl-N-(2-methoxy-4-(4-methyl-piperazin-1-yl)phenyl)-1H-[1,2,3]triazolo[4,5-h]quinazolin-8-amine | 433.1 |
| I-32 | 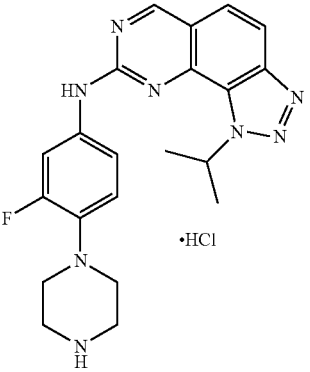 [SMILES: CC(C)n1nnc2ccc3cnc(Nc4ccc(N5CCNCC5)c(F)c4)nc3c21 ; Cl] | N-(3-Fluoro-4-(piperazin-1-yl)phenyl)-1-isopropyl-1H-[1,2,3]triazolo[4,5-h]quinazolin-8-amine hydrochloride | 407.1 |

TABLE 4-continued

Examples I-25 to I-35

| Compound No. | Chemical structure | Chemical name | LC-MS (ESI) [M + H]+ |
|---|---|---|---|
| I-33 | 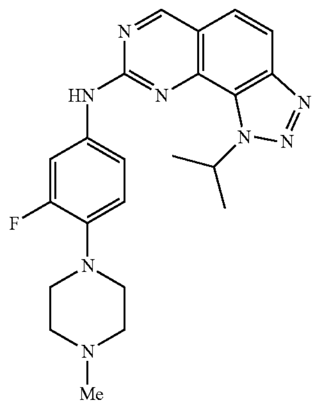 [SMILES: CC(C)n1nnc2ccc3cnc(Nc4ccc(N5CCN(C)CC5)c(F)c4)nc3c21] | N-(3-Fluoro-4-(4-methylpiperazin-1-yl)phenyl)-1-isopropyl-1H-[1,2,3]triazolo[4,5-h]quinazolin-8-amine | 421.1 |
| I-34 | 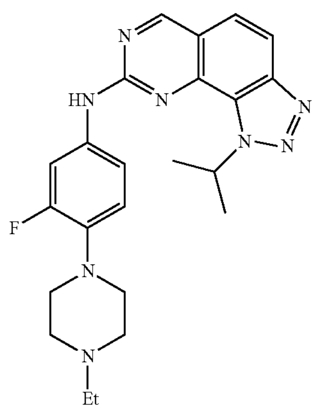 [SMILES: CCN1CCN(c2ccc(Nc3ncc4ccc5nnn(C(C)C)c5c4n3)cc2F)CC1] | N-(4-(4-Ethylpiperazin-1-yl)-3-fluorophenyl)-1-isopropyl-1H-[1,2,3]triazolo[4,5-h]quinazolin-8-amine hydrochloride | 435.1 |
| I-35 | 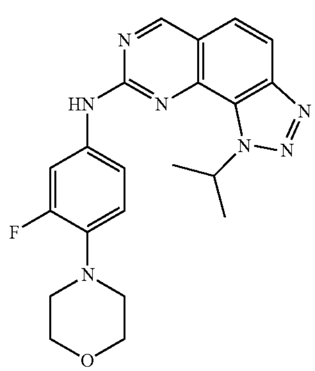 [SMILES: CC(C)n1nnc2ccc3cnc(Nc4ccc(N5CCOCC5)c(F)c4)nc3c21] | N-(3-Fluoro-4-morpholinophenyl)-1-isopropyl-1H-[1,2,3]triazolo[4,5-h]quinazolin-8-amine hydrochloride | 408.3 |

Compound I-28 (19.8 mg, 44.8 μmmol, 37%), 1-30 (12.1 mg, 26.6 μmmol, 22%) and I-32 (27.3 mg, 61.7 μmmol, 51%) were prepared from compound 8a (30 mg, 0.121 mmol) by referring to the synthesis method of I-24 in Example 24;

Compound I-25 (20.6 mg, 49.6 μmmol, 41%), I-26 (15.5 mg, 39.9 μmmol, 33%), I-27 (15.1 mg, 33.9 μmmol, 28%), 1-29 (21.2 mg, 50.8 μmmol, 42%), 1-31 (6.3 mg, 14.5 μmmol, 12%), 1-33 (14.8 mg, 35.1 μmmol, 29%), 1-34 (15.8 mg, 36.3 μmmol, 30%) and I-35 (15.3 mg, 37.5 μmmol, 31%) were prepared from compound 8a (30 mg, 0.121 mmol) by referring to the synthesis method of I-24a in Example 24.

I-25 $^1$H NMR (400 MHz, chloroform-d, ppm) δ 9.10 (s, 1H), 7.81 (d, J=8.8 Hz, 1H), 7.60-7.54 (m, 2H), 7.52 (d, J=8.8 Hz, 1H), 7.29 (s, 1H), 7.02-6.96 (m, 2H), 6.15 (p, J=6.7 Hz, 1H), 3.25 (t, J=5.0 Hz, 4H), 2.67 (t, J=5.1 Hz, 4H), 2.52 (q, J=7.2 Hz, 2H), 1.79 (d, J=6.7 Hz, 6H), 1.16 (t, J=7.2 Hz, 3H).

I-26 $^1$H NMR (400 MHz, chloroform-d, ppm) δ 9.11 (s, 1H), 7.82 (d, J=8.8 Hz, 1H), 7.66-7.57 (m, 2H), 7.53 (d, J=8.8 Hz, 1H), 7.35 (s, 1H), 7.03-6.93 (m, 2H), 6.16 (p, J=6.7 Hz, 1H), 3.91 (dd, J=6.0, 3.6 Hz, 4H), 3.18 (dd, J=5.8, 3.8 Hz, 4H), 1.80 (d, J=6.7 Hz, 6H).

I-27 ¹H NMR (400 MHz, chloroform-d, ppm) δ 9.09 (s, 1H), 7.80 (d, J=8.8 Hz, 1H), 7.59-7.54 (m, 2H), 7.52 (d, J=8.8 Hz, 1H), 7.33 (s, 1H), 7.02-6.96 (m, 2H), 6.16 (p, J=6.7 Hz, 1H), 3.67 (q, J=7.8, 7.3 Hz, 4H), 2.71 (t, J=11.0 Hz, 2H), 1.85 (d, J=8.6 Hz, 2H), 1.79 (d, J=6.7 Hz, 2H), 1.64 (q, J=7.0 Hz, 4H), 1.44-1.35 (m, 1H).

I-28a ¹H NMR (400 MHz, chloroform-d, ppm) δ 9.21 (s, 1H), 8.36 (dd, J=8.9, 5.9 Hz, 1H), 8.16 (s, 1H), 7.73 (d, J=8.8 Hz, 1H), 7.51 (d, J=8.8 Hz, 1H), 6.93 (m, 2H), 6.20 (p, J=6.7 Hz, 1H), 3.62 (t, J=5.1 Hz, 4H), 3.14 (t, J=5.1 Hz, 4H), 1.82 (d, J=6.7 Hz, 6H), 1.48 (s, 9H).

I-29 ¹H NMR (400 MHz, chloroform-d, ppm) δ 9.16 (s, 1H), 8.47 (dd, J=8.9, 5.9 Hz, 1H), 8.20 (s, 1H), 7.87 (d, J=8.8 Hz, 1H), 7.57 (d, J=8.8 Hz, 1H), 6.93 (ddd, J=17.0, 9.1, 2.9 Hz, 2H), 6.20 (p, J=6.7 Hz, 1H), 4.02-3.90 (m, 4H), 2.96 (dd, J=5.6, 3.6 Hz, 4H), 1.85 (d, J=6.7 Hz, 6H).

I-30a ¹H NMR (400 MHz, chloroform-d, ppm) δ 9.18 (s, 1H), 8.28 (d, J=8.6 Hz, 1H), 7.76 (d, J=8.8 Hz, 1H), 7.63 (s, 1H), 7.48 (d, J=8.8 Hz, 1H), 6.59-6.43 (m, 2H), 6.12 (p, J=6.7 Hz, 1H), 3.91 (s, 3H), 3.58 (t, J=5.0 Hz, 4H), 3.10 (t, J=5.0 Hz, 4H), 1.81 (d, J=6.7 Hz, 6H), 1.50 (s, 9H).

I-31 ¹H NMR (400 MHz, chloroform-d, ppm) δ 9.10 (s, 1H), 8.31 (d, J=8.6 Hz, 1H), 7.81 (d, J=8.8 Hz, 1H), 7.75 (s, 1H), 7.52 (d, J=8.8 Hz, 1H), 6.69-6.51 (m, 2H), 6.24 (p, J=6.7 Hz, 1H), 3.93 (s, 3H), 3.25 (t, J=5.0 Hz, 4H), 2.67 (t, J=4.9 Hz, 4H), 2.41 (s, 3H), 1.84 (d, J=6.7 Hz, 6H).

I-32a δ 9.11 (s, 1H), 7.92 (dd, J=14.7, 2.5 Hz, 1H), 7.80 (d, J=8.8 Hz, 1H), 7.48 (d, J=8.8 Hz, 1H), 7.41 (s, 1H), 7.18-7.27 (m, 1H), 6.87 (t, J=9.0 Hz, 1H), 6.13 (p, J=6.7 Hz, 1H), 3.32 (t, J=4.8 Hz, 4H), 2.93 (t, J=4.9 Hz, 4H), 1.85 (d, J=6.6 Hz, 6H), 1.53 (s, 9H).

I-33 ¹H NMR (400 MHz, chloroform-d, ppm) δ 9.13 (s, 1H), 7.94 (dd, J=14.7, 2.5 Hz, 1H), 7.86 (d, J=8.8 Hz, 1H), 7.55 (d, J=8.8 Hz, 1H), 7.44 (s, 1H), 7.11-7.03 (m, 1H), 6.98 (t, J=9.0 Hz, 1H), 6.21 (p, J=6.7 Hz, 1H), 3.14 (t, J=4.8 Hz, 4H), 2.66 (t, J=4.9 Hz, 4H), 2.39 (s, 3H), 1.85 (d, J=6.6 Hz, 6H).

I-34 ¹H NMR (400 MHz, chloroform-d, ppm) δ 9.14 (s, 1H), 7.94 (dd, J=14.6, 2.5 Hz, 1H), 7.87 (d, J=8.8 Hz, 1H), 7.56 (d, J=8.8 Hz, 1H), 7.40 (s, 1H), 7.07 (dd, J=8.9, 2.5 Hz, 1H), 6.99 (t, J=8.9 Hz, 1H), 6.21 (p, J=6.7 Hz, 1H), 3.17 (t, J=4.9 Hz, 4H), 2.71 (s, 4H), 2.54 (q, J=7.2 Hz, 2H), 1.85 (d, J=6.7 Hz, 6H), 1.16 (t, J=7.2 Hz, 3H).

I-35 ¹H NMR (400 MHz, chloroform-d, ppm) δ 9.14 (s, 1H), 7.96 (dd, J=14.7, 2.5 Hz, 1H), 7.87 (d, J=8.8 Hz, 1H), 7.56 (d, J=8.8 Hz, 1H), 7.47 (s, 1H), 7.09 (dd, J=9.0, 2.5 Hz, 1H), 6.97 (t, J=9.0 Hz, 1H), 6.22 (p, J=6.7 Hz, 1H), 3.96-3.86 (m, 4H), 3.15-3.05 (m, 4H), 1.86 (d, J=6.7 Hz, 6H).

Example I-36

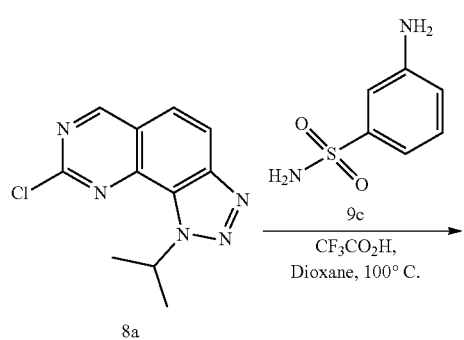

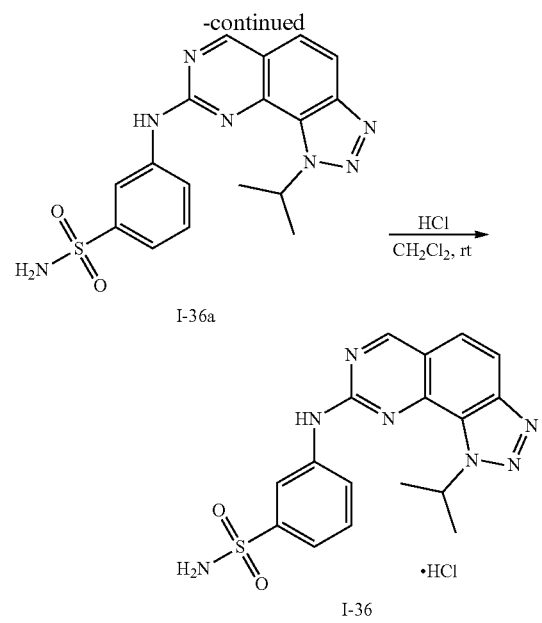

1): Preparation of 3-((1-Isopropyl-1H-[1,2,3]triazolo[4,5-h]quinazolin-8-yl)amino)benzenesulfonamide I-36a The solution of compound 8a (30 mg, 0.121 mmol) and 9c (41.6 mg, 0.242 mmol) in 1,4-dioxane (1.5 mL) was replaced with argon twice, and trifluoroacetic acid (13.5 μL, 0.182 mmol) was added. The mixture was heated to 100° C. and reacted in a sealed tube for 8 hours. After the mixture was cooled to room temperature, ethyl acetate (5 mL) and half-saturated aqueous sodium bicarbonate solution (8 mL) were added to dilute the mixture. Organic layer was separated, and the aqueous layer was extracted with ethyl acetate (5 ml) for 3 times. The organic layers were combined, washed with saturated brine (5 mL), dried by anhydrous sodium sulfate, suction filtered, and concentrated. The resulting residue was purified by flash silica gel column chromatography (dichloromethane/methanol=80:1 to 10:1) to afford a light yellow solid product, which was the title compound I-36a (16.7 mg, 43.6 μmol, 36%). ¹H NMR (400 MHz, chloroform-d, ppm) δ 9.36 (s, 1H), 8.29 (s, 1H), 8.00 (d, J=9.0 Hz, 1H), 7.86 (d, 1H, J=8.0 Hz), 7.65 (d, J=9.0 Hz, 1H), 7.51 (t, 1H, J=8.0 Hz), 7.43 (dt, 1H, J=8.0, 1.2 Hz), 5.83 (p, J=6.5 Hz, 1H), 3.73 (s, 2H), 1.68 (d, J=6.7 Hz, 6H).

2): Preparation of 3-((1-isopropyl-1H-[1,2,3]triazolo[4,5-h]quinazolin-8-yl)amino)benzenesulfonamide hydrochloride (I-36)

Compound I-36a (12 mg, 31.3 μmol) was dissolved in dichloromethane (2 mL), and the solution of hydrogen chloride in 1,4-dioxane (4 M, 0.2 mL) was added. After being stirred at room temperature for 2 hours, the mixture was concentrated and vacuum-dried by an oil pump to constant weight. The resulting yellow powder was the title compound I-36 (12.6 mg). LC-MS (ESI), $C_{17}H_{18}N_7O_2S$ [M+H]⁺: m/z=384.2.

TABLE 5
Example I-37 to I-40
| Compound No. | Chemical structure | Chemical name | LC-MS (ESI) [M + H]+ |
|---|---|---|---|
| I-37 | 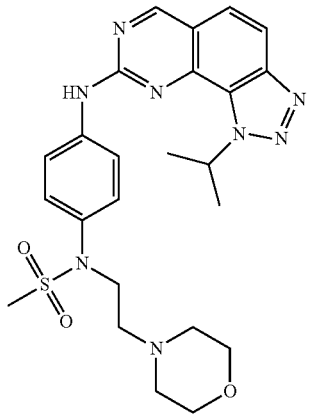 [SMILES: CC(C)n1nnc2ccc3cnc(Nc4ccc(N(CCN5CCOCC5)S(C)(=O)=O)cc4)nc3c21] | N-(4-((1-Isopropyl-1H-[1,2,3]triazolo[4,5-h]quinazolin-8-yl)amino)phenyl)-N-(2-morpholinoethyl)methanesulfonamide | 511.3 |
| I-38 | 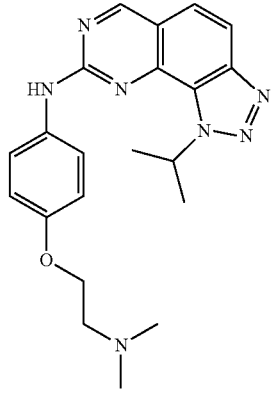 [SMILES: CC(C)n1nnc2ccc3cnc(Nc4ccc(OCCN(C)C)cc4)nc3c21] | N-(4-(2-(Dimethylamino)ethoxy)phenyl)-1-isopropyl-1H-[1,2,3]triazolo[4,5-h]quinazolin-8-amine | 392.1 |
| I-39 | 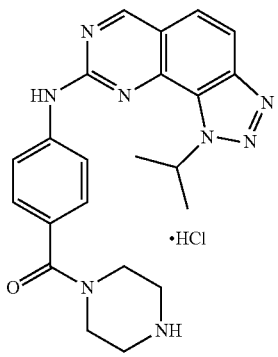 [SMILES: CC(C)n1nnc2ccc3cnc(Nc4ccc(C(=O)N5CCNCC5)cc4)nc3c21 ; Cl] | (4-((1-Isopropyl-1H-[1,2,3]triazolo[4,5-h]quinazolin-8-yl)amino)phenyl)(piperazin-1-yl)methanone hydrochloride | 417.2 |

TABLE 5-continued

Example I-37 to I-40

| Compound No. | Chemical structure | Chemical name | LC-MS (ESI) [M + H]+ |
|---|---|---|---|
| I-40 | 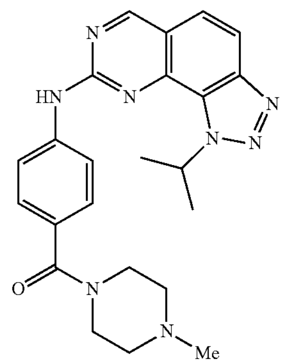 [SMILES: CC(C)n1nnc2ccc3cnc(Nc4ccc(C(=O)N5CCN(C)CC5)cc4)nc3c21] | (4-((1-(Isopropyl-1H-[1,2,3]triazolo[4,5-h]quinazolin-8-yl)amino)phenyl)(4-methylpiperazin-1-yl)methanone | 431.3 |

Compound I-39 (8.1 mg, 17.8 μmmol, 110%) was prepared from compound 8a (40 mg, 0.162 mmol) by referring to the synthesis method of I-36 in Example 36;

Compound I-37 (9.9 mg, 19.4 μmmol, 12%), I-38 (12.0 mg, 30.8 μmmol, 19%) and I-40 (9.1 mg, 21.1 μmmol, 13%) were prepared from compound 8a (40 mg, 0.162 mmol) by referring to the synthesis method of I-36a in Example 36.

I-37 $^1$H NMR (400 MHz, chloroform-d, ppm) δ 9.31 (s, 1H), 8.12 (d, J=9.0 Hz, 1H), 7.71 (d, J=8.8 Hz, 1H), 7.32 (d, J=9.0 Hz, 2H), 6.99 (d, J=9.0 Hz, 2H), 6.22 (p, J=6.7 Hz, 1H), 3.92 (brs, 4H), 3.56 (t, 2H), 3.33 (m, 4H), 2.91 (s, 3H), 2.24 (t, 2H), 1.71 (d, J=6.6 Hz, 6H).

I-38 $^1$H NMR (400 MHz, chloroform-d, ppm) δ 9.11 (s, 1H), 7.82 (d, J=8.8 Hz, 1H), 7.58 (d, J=9.0 Hz, 2H), 7.53 (d, J=8.8 Hz, 1H), 7.34 (s, 1H), 6.97 (d, J=9.0 Hz, 2H), 6.13 (p, J=6.7 Hz, 1H), 4.12 (t, J=5.7 Hz, 2H), 2.79 (t, J=5.6 Hz, 2H), 1.78 (d, J=6.7 Hz, 6H).

I-39a 1H NMR (400 MHz, chloroform-d, ppm) δ 9.19 (s, 1H), 7.90 (d, J=8.8 Hz, 1H), 7.81 (d, J=8.6 Hz, 2H), 7.70 (s, 1H), 7.59 (d, J=8.8 Hz, 1H), 7.48 (d, J=8.6 Hz, 2H), 6.20 (p, J=6.7 Hz, 1H), 3.63 (s, 4H), 3.49 (s, 4H), 1.84 (d, J=6.7 Hz, 6H), 1.48 (s, 9H).

I-40 $^1$H NMR (400 MHz, chloroform-d, ppm) δ 9.19 (s, 1H), 7.90 (d, J=8.8 Hz, 1H), 7.84-7.76 (m, 2H), 7.63 (s, 1H), 7.58 (d, J=8.9 Hz, 1H), 7.52-7.46 (m, 2H), 6.21 (p, J=6.7 Hz, 1H), 3.70 (s, 4H), 2.45 (s, 4H), 1.85 (d, J=6.7 Hz, 6H).

Biological Example 1

Kinase Activity Assay

The inhibitory effect of the compound on the kinase CDK4/cyclin D3 was tested by the Caliper Mobility Shift Assay method. The final test concentration of the compound was 10 concentrations, which started from 1p M and were obtained by three-fold dilution. 5 μL of 5-fold final concentration compound and 10 μL of CDK4/Cyclin D3 kinase solution with final concentration of 10 nM were added to the 384-well reaction plate respectively, and pre incubated at room temperature for 10 minutes (the negative control well contained 10 μL kinase buffer and 5 μL 5% DMSO; the positive control well contained 10 μL kinase solution and 5 μL 5% DMSO). The mixture of 10 μL ATP with a final concentration of 250 μM and the corresponding substrate peptide was added to initiate the reaction, and the mixture was reacted at room temperature for 150 minutes. 30 μL of stop test solution containing EDTA was added to stop the kinase reaction. Conversion rate was read by Caliper EZ Reader. Conversion inhibition rate %=(average conversion rate of positive control %−sample conversion rate %)/ (average conversion rate of positive control %−average conversion rate of negative control %). Wherein: the negative control well represents conversion rate reading of wells without enzyme activity; the positive control well represents conversion rate reading of wells without compound inhibition. The log value of concentration was taken as the X-axis and the percentage inhibition rate was the Y-axis. The dose-effect curve was fitted by log(inhibitor) vs. response— Variable slope of the analysis software GraphPad Prism 5, and the IC50 value of each compound on the enzyme activity was obtained. Calculation formula: Y=Bottom+ (Top−Bottom)/(1+10^((Log IC50−X)*HillSlope)).

The IC50 values of the compounds of the present disclosure for CDK6/cyclin D3 and CDK2/cyclin A2 were tested in a similar manner.

The results of the enzyme inhibitory activity of the most representative compounds of the present disclosure are shown in the table below, wherein A represents $IC_{50}$<10 nM, B represents 10 nM≤$IC_{50}$<50 nM, C represents 50 nM≤$IC_{50}$<100 nM, D represents $IC_{50}$≥100 nM. Positive control compound: palbociclib.

| Compound No. | CDK4/D3 IC$_{50}$ (nM) | CDK6/D3 IC$_{50}$ (nM) | CDK2/A2 IC$_{50}$ (nM) |
|---|---|---|---|
| Palbociclib | 2.2 | 5.8 | |
| I-1 | A | A | |
| I-2 | B | C | |
| I-3 | A | A | |
| I-4 | A | A | |
| I-5 | A | A | |
| I-6 | A | B | |
| I-7 | A | A | |
| I-8 | A | B | |
| I-9 | A | A | |
| I-10 | A | B | |
| I-11 | A | A | |
| I-12 | A | A | |
| I-13 | A | B | |
| I-14 | A | B | |
| I-15 | A | B | |

-continued

| Compound No. | CDK4/D3 IC$_{50}$ (nM) | CDK6/D3 IC$_{50}$ (nM) | CDK2/A2 IC$_{50}$ (nM) |
|---|---|---|---|
| I-16 | A | A | |
| I-17 | A | B | |
| I-18 | A | B | |
| I-19 | A | B | |
| I-20 | A | B | |
| I-21 | B | C | |
| I-22 | A | A | |
| I-23 | A | B | |
| I-24 | A | A | A |
| I-25 | A | A | A |
| I-26 | A | A | A |
| I-27 | C | C | C |
| I-28 | A | A | A |
| I-29 | C | C | C |
| I-30 | A | A | A |
| I-31 | C | C | C |
| I-32 | A | A | A |
| I-33 | A | A | A |
| I-34 | A | A | A |
| I-35 | B | B | B |
| I-36 | A | A | A |
| I-37 | A | A | A |
| I-38 | A | A | A |
| I-39 | A | A | A |
| I-40 | A | A | A |

The above is a further detailed description of the present disclosure in connection with the specific preferred embodiments, and the specific embodiments of the present disclosure are not limited to the description. It will be apparent to those skilled in the art that the present disclosure may be practiced by making various simple deduction and replacement, without departing from the spirit and scope of the invention.

What is claimed is:

1. A compound of formula (I), or a pharmaceutically acceptable salt, enantiomer, diastereomer, racemate, solvate, hydrate, polymorph, prodrug, or isotopic variant thereof, or a

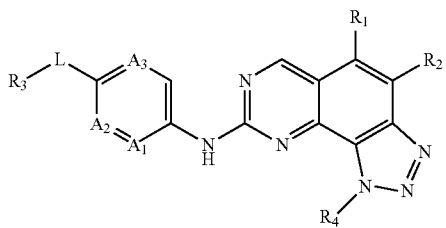

(I)

wherein:
$A_1$ is selected from $CR_5$ or N;
$A_2$ is selected from $CR_6$ or N;
$A_3$ is selected from $CR_7$ or N;
$R_1$ is selected from H, D, halogen, —CN, —OR$_a$, —SR$_a$, —NR$_b$R$_c$, —C(O)R$_a$, —C(O)OR$_a$, —C(O)NR$_b$R$_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the $C_{3-7}$ cycloalkyl or 3- to 7-membered heterocyclyl is optionally substituted with oxo or thioxo;
$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
wherein the $C_{3-7}$ cycloalkyl or 3- to 7-membered heterocyclyl is optionally substituted with oxo or thioxo;
$R_3$ is selected from H, D, halogen, —CN, —NO$_2$, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, —O—$C_{1-6}$ alkylene-R$_8$, $C_{1-6}$ alkyl, $C_{1-6}$ haloalkyl, $C_{3-7}$ cycloalkyl, 3- to 11-membered heterocyclyl, $C_{6-10}$ aryl or 5- to 10-membered heteroaryl, each of which is optionally substituted with 1, 2, 3, 4 or 5 R$_8$ group(s);
$R_4$ is selected from H, —C(O)R$_a$, —C(O)OR$_a$, —C(O)NR$_b$R$_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
L is selected from bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;
and wherein,
$R_5$ is selected from H, D, halogen, —CN, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, $C_{1-6}$ alkyl or $C_{1-6}$ haloalkyl;
$R_6$ is selected from H, D, halogen, —CN, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, $C_{1-6}$ alkyl or $C_{1-6}$ haloalkyl;
$R_7$ is selected from H, D, halogen, —CN, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, $C_{1-6}$ alkyl or $C_{1-6}$ haloalkyl;
$R_8$ is selected from H, D, —NH$_2$, —NHC$_{1-6}$ alkyl, —N($C_{1-6}$ alkyl)$_2$, $C_{1-6}$ alkyl, $C_{1-6}$ haloalkyl, —$C_{0-6}$ alkylene-OR$_a$, $C_{3-7}$ cycloalkyl, 3- to 7-membered heterocyclyl, $C_{6-10}$ aryl or 5- to 10-membered heteroaryl; or two R$_8$ groups on the same atom are taken together to form oxo or thioxo;
$R_a$ is independently selected from H, —$C_{0-6}$ alkylene-CN, —$C_{0-6}$ alkylene-NO$_2$, —$C_{0-6}$ alkylene-OR', —$C_{0-6}$ alkylene-SR', —$C_{0-6}$ alkylene-NR"R'", —$C_{0-6}$ alkylene-C(O) R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;
$R_b$ and $R_c$ are independently selected from H, —$C_{0-6}$ alkylene-CN, —$C_{0-6}$ alkylene-NO$_2$, —$C_{0-6}$ alkylene-OR', —$C_{0-6}$ alkylene-SR', —$C_{0-6}$ alkylene-NR"R'", —$C_{0-6}$ alkylene-C(O) R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$ and $R_c$ are taken together with the nitrogen atoms to which they are attached to form 3- to 7-membered heterocyclyl;
R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;
R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R'" are taken together with the nitrogen atoms to which they are attached to form 3- to 7-membered heterocyclyl;

m represents 0, 1 or 2;

and, $R_1$—$R_2$ and $R_4$—$R_8$ are optionally substituted with 1, 2 or 3 R group(s), wherein R is independently selected from H, —OH, halogen, —NO$_2$, carbonyl, —CN, —OR$_a$, —SR$_a$, —NR$_b$R$_c$, —C(O)R$_a$, —C(S) R$_a$, —C(O)OR$_a$, —C(S)OR$_a$, —C(O)—NR$_b$R$_c$, —C(S)—NR$_b$R$_c$, —O—C(O)R$_a$, —O—C(S) R$_a$, —N(R$_b$)—C(O)—R$_a$, —N(R$_b$)—C(S)—R$_a$, —S(O)$_m$R$_a$, —S(O)$_m$OR$_a$, —S(O)$_m$NR$_b$R$_c$, —N(R$_b$)—S(O)$_m$—R$_a$, —N(R$_b$)—S(O)$_m$—NR$_b$R$_c$, —N(R$_b$)—C(O)OR$_a$, —N(R$_b$)—C(S) OR$_a$, —O—C$_{1-6}$ alkylene-OR$_a$, —C(O)—C$_{1-6}$ alkylene-NR$_b$R$_c$, —N(R$_b$)—C(O)—NR$_b$R$_c$, —N(R$_b$)—C(S)—NR$_b$R$_c$, —O—C(O)—NR$_b$R$_c$, —O—C(S)—NR$_b$R$_c$, C$_{1-6}$ alkyl, C$_{1-6}$ haloalkyl, C$_{2-6}$ alkenyl, C$_{2-6}$ alkynyl, C$_{3-7}$ cycloalkyl, 3- to 7-membered heterocyclyl, C$_{6-10}$ aryl or 5- to 10-membered heteroaryl; wherein the C$_{1-6}$ alkyl, C$_{1-6}$ haloalkyl, C$_{2-6}$ alkenyl, C$_{2-6}$ alkynyl, C$_{3-7}$ cycloalkyl, 3- to 7-membered heterocyclyl, C$_{6-10}$ aryl or 5- to 10-membered heteroaryl is optionally further substituted with one or more of the following groups:—CN, —NO$_2$, carbonyl, —OR$_a$, —SR$_a$, —NR$_b$R$_c$, —C(O)R$_a$, —C(S) R$_a$, —C(O)OR$_a$, —C(S)OR$_a$, —C(O)—NR$_b$R$_c$, —C(S)—NR$_b$R$_c$, —O—C(O)R$_a$, —O—C(S) R$_a$, —N(R$_b$)—C(O)—R$_a$, —N(R$_b$)—C(S)—R$_a$, —S(O)$_m$R$_a$, —S(O)$_m$OR$_a$, —S(O)$_m$NR$_b$R$_c$, —N(R$_b$)—S(O)$_m$—R$_a$, —N(R$_b$)—S(O)$_m$—R$_b$R$_c$, —N(R$_b$)—C(O)OR$_a$, —N(R$_b$)—C(S)OR$_a$, —O—C$_{1-6}$ alkylene-OR$_a$, —C(O)—C$_{1-6}$ alkylene-NR$_b$R$_c$, —N(R$_b$)—C(O)—NR$_b$R$_c$, —N(R$_b$)—C(S)—NR$_b$R$_c$, —O—C(O)—NR$_b$R$_c$ or —O—C(S)—NR$_b$R$_c$;

R$_a$, R$_b$ and R$_c$ are optionally further substituted with one or more of the following groups:

C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl or 5- to 10-membered heteroaryl.

2. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (II):

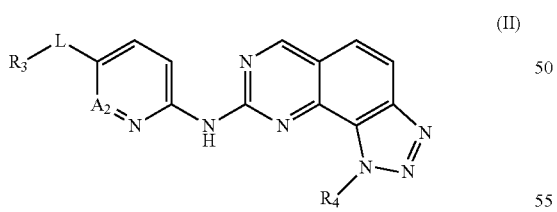

(II)

wherein:

A$_2$ is selected from CR$_6$ or N;

R$_3$ is selected from the following groups, each of which is optionally substituted with 1, 2, 3, 4 or 5 R$_8$ group(s):

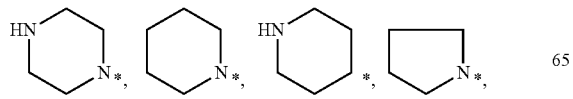

-continued

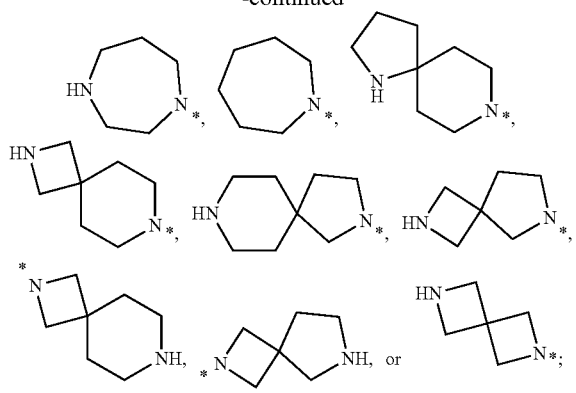

R$_4$ is selected from C$_{1-6}$ alkyl, C$_{1-6}$ haloalkyl or C$_{3-7}$ cycloalkyl;

L is selected from bond, —O—, —NH—, —C(O)—, —C(O)NH—, —NHC(O)—, —C$_{1-6}$ alkylene-, —C$_{2-6}$ alkenylene- or —C$_{2-6}$ alkynylene-;

R$_6$ is selected from H, halogen, —CN, —OR$_a$, —SR$_a$, —NR$_b$R$_c$, C$_{1-6}$ alkyl or C$_{1-6}$ haloalkyl;

R$_8$ is selected from H, —NH$_2$, —NHC$_{1-6}$ alkyl, —N(C$_{1-6}$ alkyl)$_2$, C$_{1-6}$ alkyl, C$_{1-6}$ haloalkyl, C$_{3-7}$ cycloalkyl or 3- to 7-membered heterocyclyl; or two R$_a$ groups on the same atom are taken together to form oxo or thioxo;

R$_a$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl or 5- to 10-membered heteroaryl;

R$_b$ and R$_c$ are independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl or 5- to 10-membered heteroaryl; or, R$_b$ and R$_c$ are taken together with the nitrogen atoms to which they are attached to form 3- to 7-membered heterocyclyl.

3. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (II):

(II)

wherein:

A$_2$ is selected from CR$_6$ or N;

R$_3$ is selected from the following groups, each of which is optionally substituted with 1, 2 or 3 R$_8$ group(s):

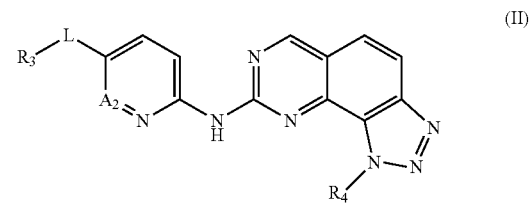

-continued

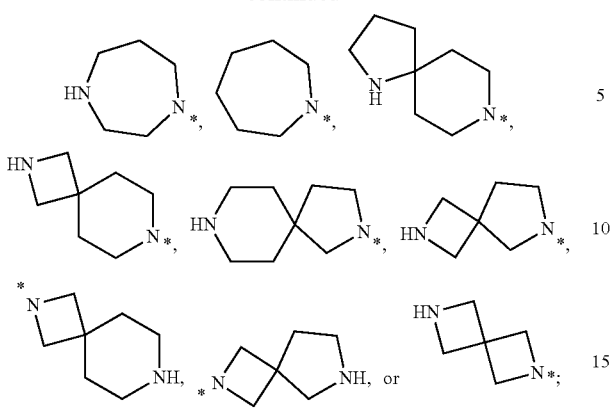

R$_4$ is selected from C$_{1-6}$ alkyl, C$_{1-6}$ haloalkyl or C$_{3-7}$ cycloalkyl;

L is selected from bond, —C$_{1-6}$ alkylene-, —C$_{2-6}$ alkenylene- or —C$_{2-6}$ alkynylene-;

R$_6$ is selected from H, halogen, —CN, C$_{1-6}$ alkyl or C$_{1-6}$ haloalkyl;

R$_8$ is selected from H, —NH$_2$, —NHC$_{1-6}$ alkyl, —N(C$_{1-6}$ alkyl)$_2$, C$_{1-6}$ alkyl, C$_{1-6}$ haloalkyl, C$_{3-7}$ cycloalkyl or 3- to 7-membered heterocyclyl; or two R$_8$ groups on the same atom are taken together to form oxo or thioxo.

4. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (II):

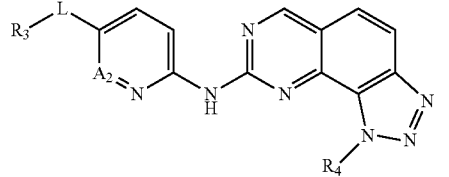

(II)

wherein:

A$_2$ is selected from CR$_6$ or N;

R$_3$ is selected from the following groups:

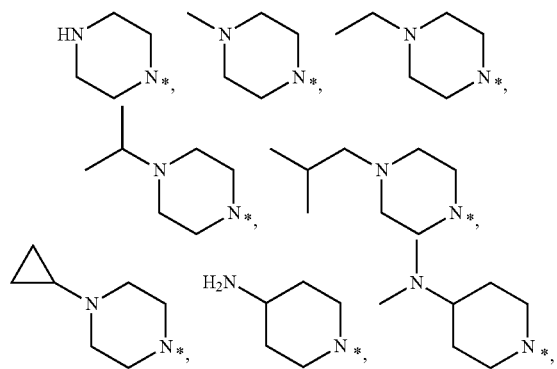

-continued

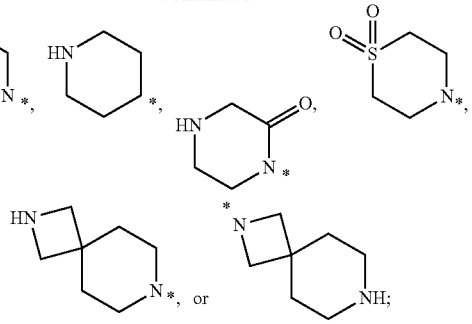

R$_4$ is selected from C$_{1-6}$ alkyl or C$_{3-7}$ cycloalkyl;
L is selected from bond or —C$_{1-6}$ alkylene-;
R$_6$ is selected from H or C$_{1-6}$ alkyl.

5. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (III) or (III-1):

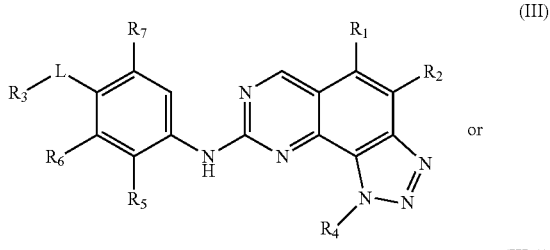

(III)

or

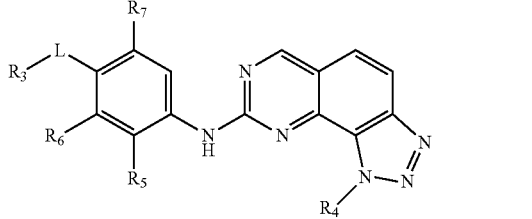

(III-1)

wherein:

R$_1$ is selected from H, D, halogen, —CN, —OR$_a$, —SR$_a$, —NR$_b$R$_c$, —C(O)R$_a$, —C(O)OR$_a$, —C(O)NR$_b$R$_c$, C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl; wherein the C$_{3-7}$ cycloalkyl or 3- to 7-membered heterocyclyl is optionally substituted with oxo or thioxo;

R$_2$ is selected from H, D, halogen, —CN, C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl; wherein the C$_{3-7}$ cycloalkyl or 3- to 7-membered heterocyclyl is optionally substituted with oxo or thioxo;

R$_3$ is selected from H, D, halogen, —CN, —NO$_2$, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, —O—C$_{1-6}$ alkylene-R$_8$, C$_{1-6}$ alkyl, C$_{1-6}$ haloalkyl, C$_{3-7}$ cycloalkyl, 3- to 11-membered heterocyclyl, C$_{6-10}$ aryl or 5- to 10-membered heteroaryl, each of which is optionally substituted with 1, 2, 3, 4 or 5 R$_8$ group(s);

R$_4$ is selected from H, D, —C(O)R$_a$, —C(O)OR$_a$, —C(O)NR$_b$R$_c$, C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl;

$R_5$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl or 5- to 10-membered heteroaryl; or two $R_8$ groups on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R"', —$C_{0-6}$ alkylene-C(O) R', —$C_{0-6}$ alkylene-C(O)OR', —$C_{0-6}$ alkylene-C(O)NR"R"', —$C_{0-6}$ alkylene-S(O)$_m$R', —$C_{0-6}$ alkylene-S(O)$_m$OR', —$C_{0-6}$ alkylene-S(O)$_m$NR"R"', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R"', —$C_{0-6}$ alkylene-C(O) R', —$C_{0-6}$ alkylene-C(O)OR', —$C_{0-6}$ alkylene-C(O)NR"R"', —$C_{0-6}$ alkylene-S(O)$_m$R', —$C_{0-6}$ alkylene-S(O)$_m$OR', —$C_{0-6}$ alkylene-S(O)$_m$NR"R"', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R"' are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R"' are taken together with the nitrogen atoms to which they are attached to form 3- to 7-membered heterocyclyl;

m represents 0, 1 or 2.

6. The compound of formula (III) or (III-1), or the pharmaceutically acceptable salt, enantiomer, diastereomer, racemate, solvate, hydrate, polymorph, prodrug, or isotopic variant thereof, or the mixture thereof according to claim 5, wherein:

$R_1$ is selected from H, D, halogen, —CN, —$OR_a$, —$SR_a$, —$NR_bR_c$, $C_{1-6}$ alkyl or $C_{1-6}$ haloalkyl;

$R_2$ is selected from H, D, halogen, —CN, —$OR_a$, —$SR_a$, —$NR_bR_c$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl, $C_{1-6}$ haloalkyl, $C_{3-7}$ cycloalkyl or 4- to 7-membered heterocyclyl, each of which is optionally substituted with 1, 2 or 3 $R_8$ group(s);

$R_4$ is selected from H, D, $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl; or two R groups on the same atom are taken together to form oxo or thioxo;

$R_a$ is independently selected from H, —$C_{0-6}$ alkylene-OR', —$C_{0-6}$ alkylene-SR', —$C_{0-6}$ alkylene-NR"R"', —$C_{0-6}$ alkylene-C(O) R', —$C_{0-6}$ alkylene-C(O)OR', —$C_{0-6}$ alkylene-C(O)NR"R"', —$C_{0-6}$ alkylene-S(O)$_m$R', —$C_{0-6}$ alkylene-S(O)$_m$OR', —$C_{0-6}$ alkylene-S(O)$_m$NR"R"', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R"', —$C_{0-6}$ alkylene-C(O) R', —$C_{0-6}$ alkylene-C(O)OR', —$C_{0-6}$ alkylene-C(O)NR"R"', —$C_{0-6}$ alkylene-S(O)$_m$R', —$C_{0-6}$ alkylene-S(O)$_m$OR', —$C_{0-6}$ alkylene-S(O)$_m$NR"R"', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$ and $R_c$ are taken together with the nitrogen atoms to which they are attached to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl;

R" and R"' are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl; or, R" and R"' are taken together with the nitrogen atoms to which they are attached to form 3- to 7-membered heterocyclyl;

m represents 0, 1 or 2.

7. The compound of formula (III) or (III-1), or the pharmaceutically acceptable salt, enantiomer, diastereomer, racemate, solvate, hydrate, polymorph, prodrug, or isotopic variant thereof, or the mixture thereof according to claim 5, wherein:

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{3-7}$ cycloalkyl or 4- to 7-membered heterocyclyl, each of which is optionally substituted with 1 or 2 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —OR$_a$, —SR$_a$, —NR$_b$R$_c$, C$_{1-6}$ alkyl or C$_{1-6}$ haloalkyl;

$R_6$ is selected from H, D, halogen, —CN, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, C$_{1-6}$ alkyl or C$_{1-6}$ haloalkyl;

$R_7$ is selected from H, D, halogen, —CN, —OR$_a$, —SR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, C$_{1-6}$ alkyl or C$_{1-6}$ haloalkyl;

L is selected from bond, —O—, —NH—, —C(O)—, —C(O)NH— or —NHC(O)—;

$R_8$ is selected from H, D, —NH$_2$, —NHC$_{1-6}$ alkyl, —N(C$_{1-6}$ alkyl)$_2$, C$_{1-6}$ alkyl or C$_{1-6}$ haloalkyl;

$R_a$ is independently selected from H, —C$_{0-6}$ alkylene-OR', —C$_{0-6}$ alkylene-SR', —C$_{0-6}$ alkylene-NR"R'", —C$_{0-6}$ alkylene-C(O) R', —C$_{0-6}$ alkylene-C(O)OR', —C$_{0-6}$ alkylene-C(O)NR"R'", —C$_{0-6}$ alkylene-S(O)$_m$R', —C$_{0-6}$ alkylene-S(O)$_m$OR', —C$_{0-6}$ alkylene-S(O)$_m$NR"R'", C$_{1-6}$ alkyl, C$_{1-6}$ haloalkyl, —C$_{0-6}$ alkylene-C$_{3-7}$ cycloalkyl or —C$_{0-6}$ alkylene-3- to 7-membered heterocyclyl;

$R_b$ and $R_c$ are independently selected from H, —C$_{0-6}$ alkylene-OR', —C$_{0-6}$ alkylene-SR', —C$_{0-6}$ alkylene-NR"R'", —C$_{0-6}$ alkylene-C(O) R', —C$_{0-6}$ alkylene-C(O)OR', —C$_{0-6}$ alkylene-C(O)NR"R'", —C$_{0-6}$ alkylene-S(O)$_m$R', —C$_{0-6}$ alkylene-S(O)$_m$OR', —C$_{0-6}$ alkylene-S(O)$_m$NR"R'", C$_{1-6}$ alkyl, C$_{1-6}$ haloalkyl, —C$_{0-6}$ alkylene-C$_{3-7}$ cycloalkyl or —C$_{0-6}$ alkylene-3- to 7-membered heterocyclyl; or, $R_b$ and $R_c$ are taken together with the nitrogen atoms to which they are attached to form 3- to 7-membered heterocyclyl;

R' is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl or 5- to 10-membered heteroaryl;

R" and R'" are independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl or 5- to 10-membered heteroaryl; or, R" and R'" are taken together with the nitrogen atoms to which they are attached to form 3- to 7-membered heterocyclyl;

m represents 0, 1 or 2.

8. The compound of formula (III) or (III-1), or the pharmaceutically acceptable salt, enantiomer, diastereomer, racemate, solvate, hydrate, polymorph, prodrug, or isotopic variant thereof, or the mixture thereof according to claim 5, wherein:

$R_1$ is selected from H or D;

$R_2$ is selected from H or D;

$R_3$ is selected from H, D, —OR$_a$, —NR$_b$R$_c$, —C(O)R$_a$, —C(O)OR$_a$, —C(O)NR$_b$R$_c$, —S(O)$_m$R$_a$, —S(O)$_m$OR$_a$, —S(O)$_m$NR$_b$R$_c$, C$_{4-6}$ cycloalkyl or 5- to 6-membered heterocyclyl, each of which is optionally substituted with one R$_8$ group;

$R_4$ is selected from C$_{1-6}$ alkyl, C$_{1-6}$ haloalkyl, C$_{3-7}$ cycloalkyl or 3- to 7-membered heterocyclyl;

$R_5$ is selected from H, D, halogen, —OR$_a$, —SR$_a$ or —NR$_b$R$_c$;

$R_6$ is selected from H, D, halogen, —C(O)R$_a$, —C(O)OR$_a$, —C(O)NR$_b$R$_c$, —S(O)$_m$R$_a$, —S(O)$_m$OR$_a$ or —S(O)$_m$NR$_b$R$_c$;

$R_7$ is selected from H, D, halogen, —C(O)R$_a$, —C(O)OR$_a$, —C(O)NR$_b$R$_c$, —S(O)$_m$R$_a$, —S(O)$_m$OR$_a$ or —S(O)$_m$NR$_b$R$_c$;

L is selected from bond, —O—, —NH—, —C(O)—, —C(O)NH— or —NHC(O)—;

$R_8$ is selected from H, D, —NH$_2$, —NHC$_{1-6}$ alkyl, —N(C$_{1-6}$ alkyl)$_2$, C$_{1-6}$ alkyl or C$_{1-6}$ haloalkyl;

$R_a$ is independently selected from H, —C$_{0-6}$ alkylene-OR', —C$_{0-6}$ alkylene-NR"R'", —C$_{0-6}$ alkylene-C(O) R', —C$_{0-6}$ alkylene-S(O)$_m$R', C$_{1-6}$ alkyl, C$_{1-6}$ haloalkyl, —C$_{0-6}$ alkylene-C$_{3-7}$ cycloalkyl or —C$_{0-6}$ alkylene-3- to 7-membered heterocyclyl;

$R_b$ and $R_c$ are independently selected from H, —C$_{0-6}$ alkylene-OR', —C$_{0-6}$ alkylene-NR"R'", —C$_{0-6}$ alkylene-C(O) R', —C$_{0-6}$ alkylene-S(O)$_m$R', C$_{1-6}$ alkyl, C$_{1-6}$ haloalkyl, —C$_{0-6}$ alkylene-C$_{3-7}$ cycloalkyl or —C$_{0-6}$ alkylene-3- to 7-membered heterocyclyl; or, $R_b$ and $R_c$ are taken together with the nitrogen atoms to which they are attached to form 5- to 6-membered heterocyclyl;

R' is independently selected from H, C$_{1-6}$ alkyl or C$_{1-6}$ haloalkyl;

R" and R'" are independently selected from H, C$_{1-6}$ alkyl or C$_{1-6}$ haloalkyl; or, R" and R'" are taken together with the nitrogen atoms to which they are attached to form 5- to 6-membered heterocyclyl;

m represents 0, 1 or 2.

9. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (III), (III-1) or (III-2):

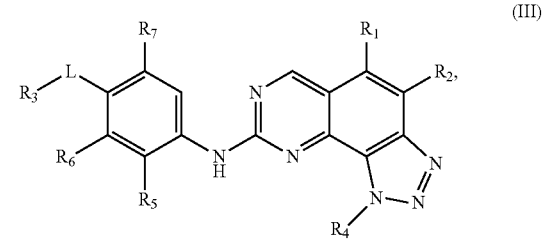

(III)

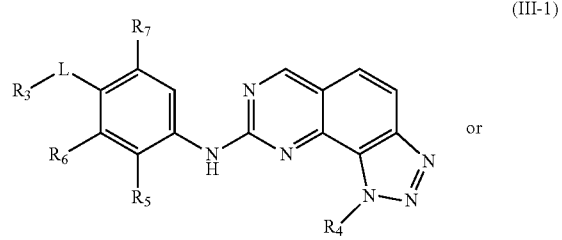

(III-1) or

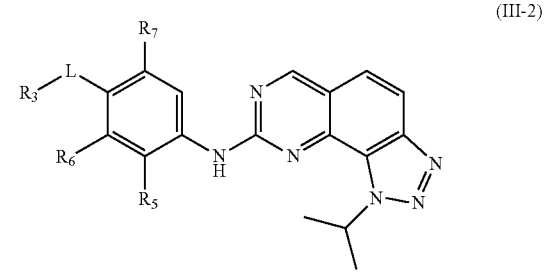

(III-2)

wherein, $R_1$ is selected from H, D, halogen, —CN, —OR$_a$, C$_{1-6}$ alkyl or C$_{1-6}$ haloalkyl;

$R_2$ is selected from H, D, halogen, —CN, —OR$_a$, C$_{1-6}$ alkyl or C$_{1-6}$ haloalkyl;

$R_3$ is selected from H, D, —OR$_a$, —NR$_b$R$_c$, C$_{1-6}$ alkyl, C$_{1-6}$ haloalkyl or 5- to 6-membered heterocyclyl, each of which is optionally substituted with 1, 2 or 3 R$_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, $C_{1-6}$ alkyl or $C_{1-6}$ haloalkyl;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

10. The compound of formula (III), (III-1) or (III-2), or the pharmaceutically acceptable salt, enantiomer, diastereomer, racemate, solvate, hydrate, polymorph, prodrug, or isotopic variant thereof, or the mixture thereof according to claim 9, wherein:

$R_1$ is selected from H, D, halogen, —CN or —$OR_a$;

$R_2$ is selected from H, D, halogen, —CN or —$OR_a$;

$R_3$ is selected from H, D, —$OR_a$, —$NR_bR_c$, $C_{1-6}$ alkyl, $C_{1-6}$ haloalkyl or piperazinyl, each of which is optionally substituted with 1 or 2 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$ or —$NR_bR_c$;

$R_6$ is selected from H, D, halogen, —CN, —$OR_a$, —$SR_a$ or —$NR_bR_c$;

$R_7$ is selected from H, D, halogen, —CN, —$OR_a$, —$SR_a$ or —$NR_bR_c$;

L is selected from bond, —O—, —NH—, —C(O)—, —C(O)NH— or —NHC(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

11. The compound of formula (III), (III-1) or (III-2), or the pharmaceutically acceptable salt, enantiomer, diastereomer, racemate, solvate, hydrate, polymorph, prodrug, or isotopic variant thereof, or the mixture thereof according to claim 9, wherein:

$R_1$ is selected from H or D;

$R_2$ is selected from H or D;

$R_3$ is selected from H, D, —$OR_a$, —$NR_bR_c$, $C_{1-6}$ alkyl, $C_{1-6}$ haloalkyl or piperazinyl, each of which is optionally substituted with one $R_8$ group;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$ or —$NR_bR_c$;

$R_6$ is selected from H, D or halogen;

$R_7$ is selected from H, D or halogen;

L is selected from bond, —O—, —NH— or —C(O)—;

$R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

12. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (IV) or (IV-1):

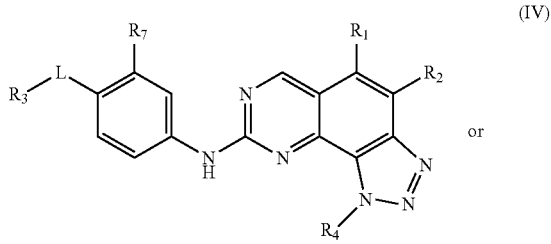

(IV)

or

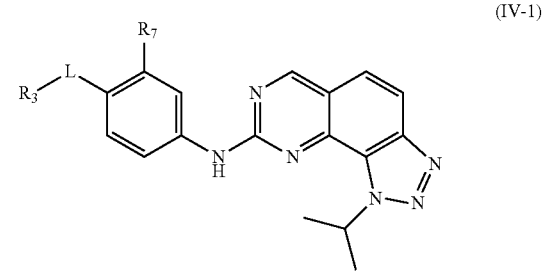

(IV-1)

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, —$OR_a$, —$NR_bR_c$, $C_{1-6}$ alkyl, $C_{1-6}$ haloalkyl or 5- to 6-membered heterocyclyl, each of which is optionally substituted with 1, 2 or 3 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

L is selected from bond, —O—, —NH—, —C(O)—, —C(O)NH— or —NHC(O)—;

$R_7$ is selected from H, D, halogen, —CN, —$OR_a$, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

13. The compound of formula (IV) or (IV-1), or the pharmaceutically acceptable salt, enantiomer, diastereomer, racemate, solvate, hydrate, polymorph, prodrug, or isotopic variant thereof, or the mixture thereof according to claim 12, wherein:

$R_1$ is selected from H, D, halogen, —CN or —$OR_a$;

$R_2$ is selected from H, D, halogen, —CN or —$OR_a$;

$R_3$ is selected from H, D, —$OR_a$, —$NR_bR_c$, $C_{1-6}$ alkyl, $C_{1-6}$ haloalkyl or piperazinyl, each of which is optionally substituted with 1 or 2 $R_8$ group(s);

$R_4$ is selected from $C_{1-6}$ alkyl, $C_{1-6}$ haloalkyl, $C_{3-7}$ cycloalkyl or 3- to 7-membered heterocyclyl;

L is selected from bond, —O—, —NH—, —C(O)—, —C(O)NH— or —NHC(O)—;

$R_7$ is selected from H, D, halogen, —CN, —OR$_a$, $C_{1-6}$ alkyl or $C_{1-6}$ haloalkyl;

$R_8$ is selected from H, D, —NH$_2$, —NHC$_{1-6}$ alkyl, —N(C$_{1-6}$ alkyl)$_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

14. The compound of formula (IV) or (IV-1), or the pharmaceutically acceptable salt, enantiomer, diastereomer, racemate, solvate, hydrate, polymorph, prodrug, or isotopic variant thereof, or the mixture thereof according to claim 12, wherein:

$R_1$ is selected from H or D;

$R_2$ is selected from H or D;

$R_3$ is selected from H, D, —OR$_a$, —NR$_b$R$_c$, $C_{1-6}$ alkyl, $C_{1-6}$ haloalkyl or piperazinyl, each of which is optionally substituted with one R$_8$ group;

$R_4$ is selected from $C_{1-6}$ alkyl, $C_{1-6}$ haloalkyl, $C_{3-7}$ cycloalkyl or 3- to 7-membered heterocyclyl;

L is selected from bond, —O—, —NH— or —C(O)—;

$R_7$ is selected from H, D or halogen;

$R_8$ is selected from H, D, —NH$_2$, —NHC$_{1-6}$ alkyl, —N(C$_{1-6}$ alkyl)$_2$, $C_{1-6}$ alkyl or $C_{1-6}$ haloalkyl;

$R_a$ is independently selected from H, $C_{1-6}$ alkyl or $C_{1-6}$ haloalkyl;

$R_b$ and $R_c$ are independently selected from H, $C_{1-6}$ alkyl or $C_{1-6}$ haloalkyl; or, $R_b$ and $R_c$ are taken together with the nitrogen atoms to which they are attached to form 5- to 6-membered heterocyclyl.

15. The compound of formula (I), or the pharmaceutically acceptable salt, enantiomer, diastereomer, racemate, solvate, hydrate, polymorph, prodrug, or isotopic variant thereof, or the mixture thereof according to claim 1, which is the compound of formula (V) or (V-1):

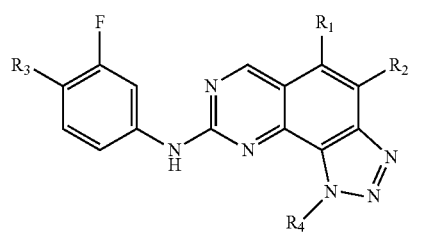

(V)

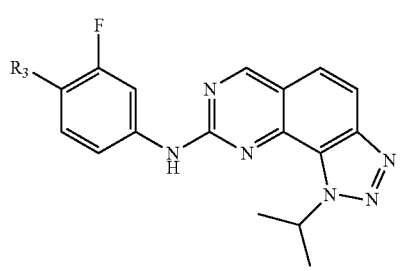

(V-1)

wherein, $R_1$ is selected from H, D, halogen, —CN, —OR$_a$, $C_{1-6}$ alkyl or $C_{1-6}$ haloalkyl;

$R_2$ is selected from H, D, halogen, —CN, —OR$_a$, $C_{1-6}$ alkyl or $C_{1-6}$ haloalkyl;

$R_3$ is 5- to 6-membered heterocyclyl optionally substituted with 1, 2 or 3 R$_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_8$ is selected from H, —NH$_2$, —NHC$_{1-6}$ alkyl, —N(C$_{1-6}$ alkyl)$_2$, $C_{1-6}$ alkyl or $C_{1-6}$ haloalkyl;

$R_a$ is independently selected from H, $C_{1-6}$ alkyl or $C_{1-6}$ haloalkyl.

16. The compound of formula (V) or (V-1), or the pharmaceutically acceptable salt, enantiomer, diastereomer, racemate, solvate, hydrate, polymorph, prodrug, or isotopic variant thereof, or the mixture thereof according to claim 15, wherein:

$R_1$ is selected from H, D, halogen, —CN or —OR$_a$;

$R_2$ is selected from H, D, halogen, —CN or —OR$_a$;

$R_3$ is piperazinyl optionally substituted with 1 or 2 R$_8$ group(s);

$R_4$ is selected from $C_{1-6}$ alkyl, $C_{1-6}$ haloalkyl, $C_{3-7}$ cycloalkyl or 3- to 7-membered heterocyclyl;

$R_8$ is selected from H, D, $C_{1-6}$ alkyl or $C_{1-6}$ haloalkyl;

$R_a$ is independently selected from H, $C_{1-6}$ alkyl or $C_{1-6}$ haloalkyl.

17. The compound of formula (V) or (V-1), or the pharmaceutically acceptable salt, enantiomer, diastereomer, racemate, solvate, hydrate, polymorph, prodrug, or isotopic variant thereof, or the mixture thereof according to claim 15, wherein:

$R_1$ is selected from H or D;

$R_2$ is selected from H or D;

$R_3$ is piperazinyl optionally substituted with one R$_8$ group;

$R_4$ is selected from $C_{1-6}$ alkyl, $C_{1-6}$ haloalkyl, $C_{3-7}$ cycloalkyl or 3- to 7-membered heterocyclyl;

$R_8$ is selected from H, D, $C_{1-6}$ alkyl or $C_{1-6}$ haloalkyl.

18. A compound, or a pharmaceutically acceptable salt, enantiomer, diastereomer, racemate, solvate, hydrate, polymorph, prodrug, or isotopic variant thereof, or the mixture thereof, wherein the compound is selected from:

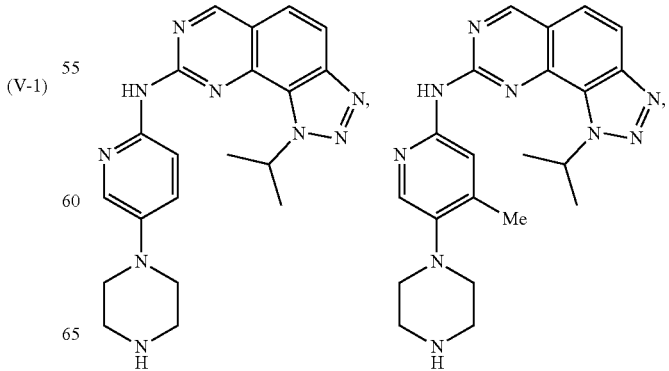

113
-continued
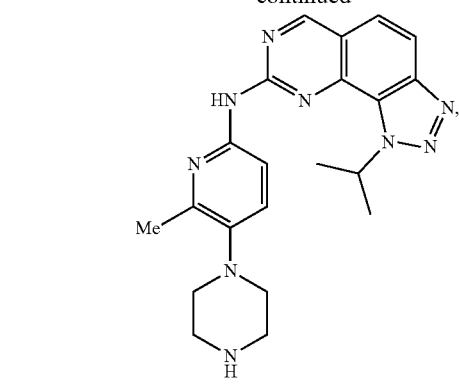
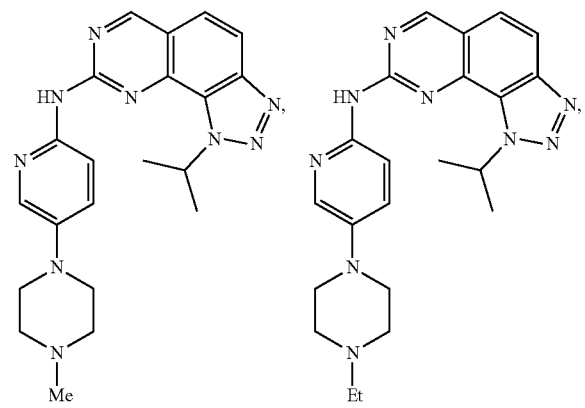
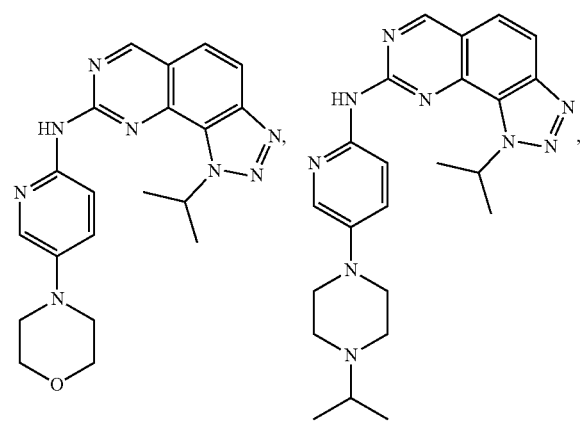
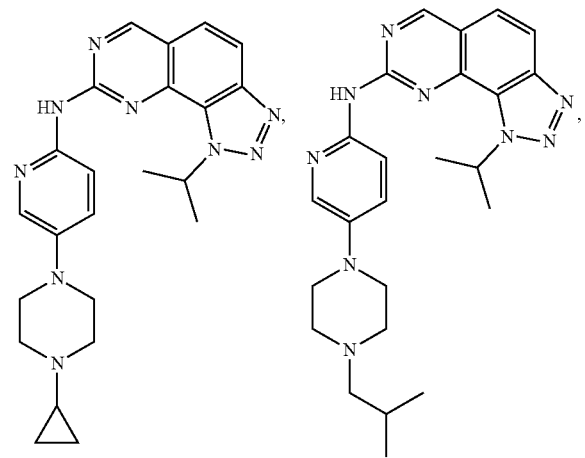
114
-continued
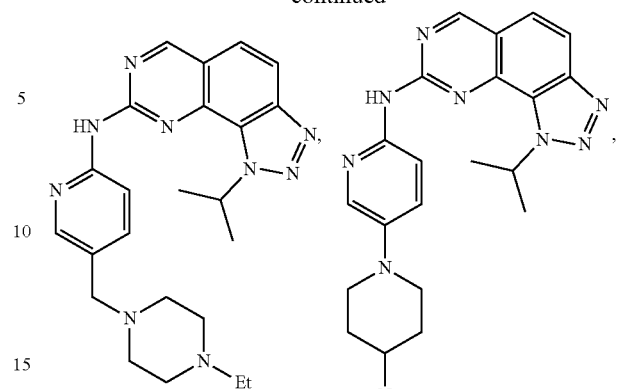
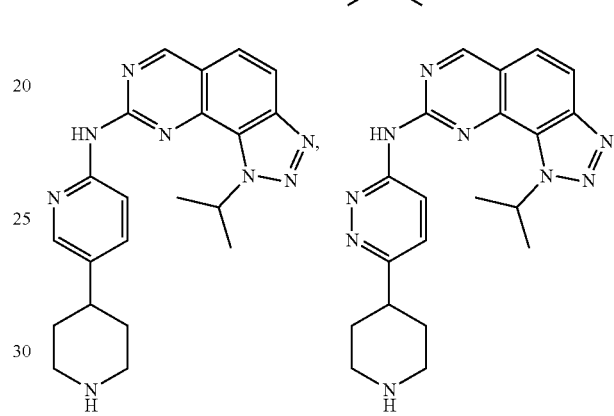
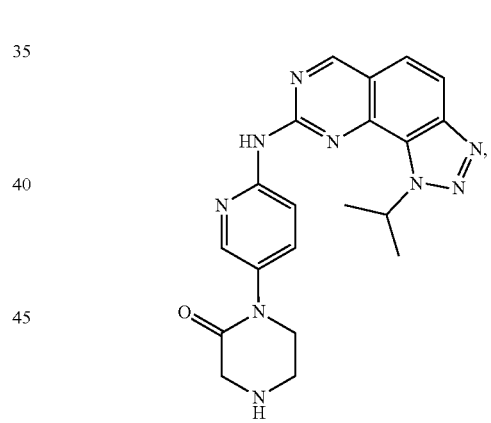
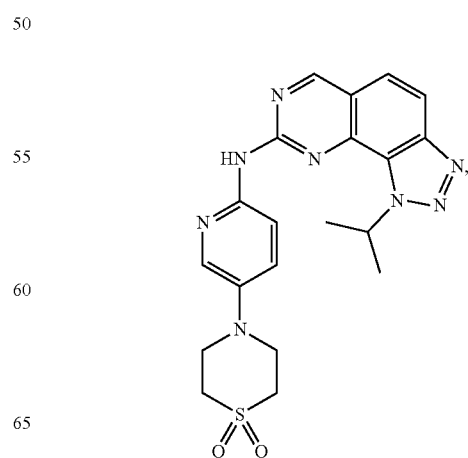

115
-continued
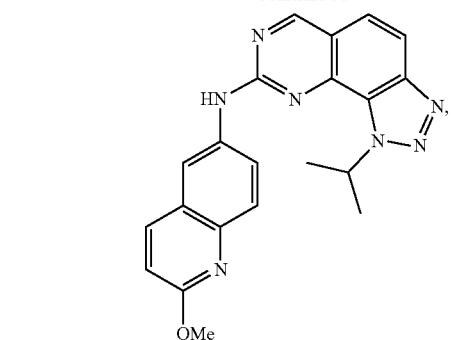
116
-continued
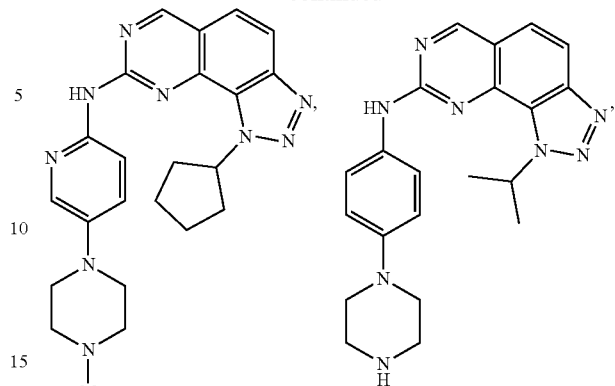
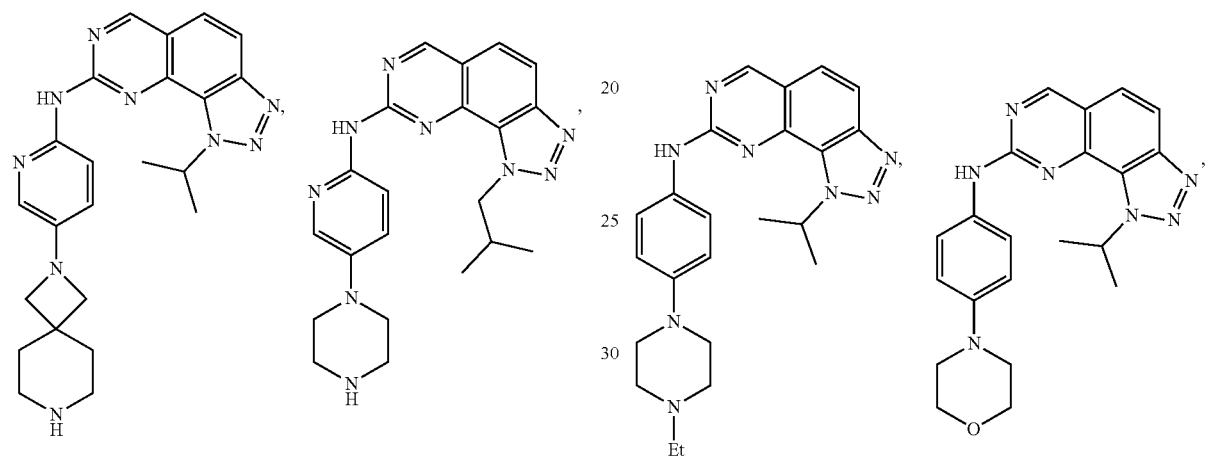
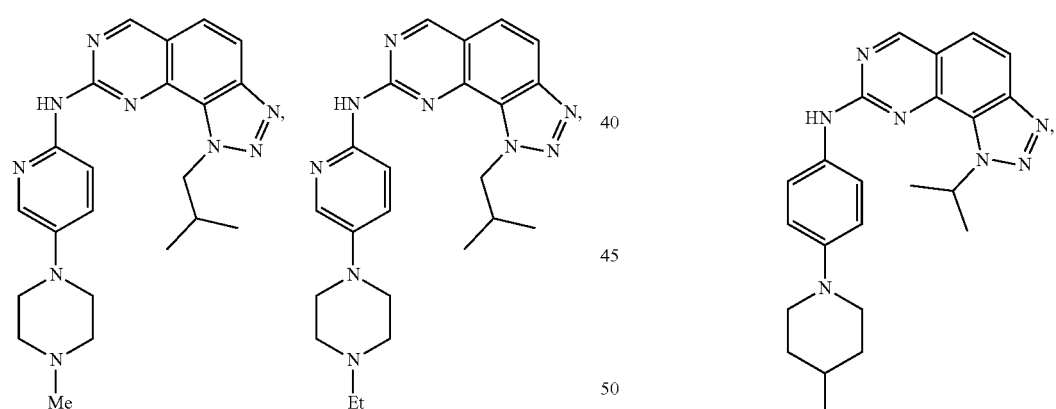
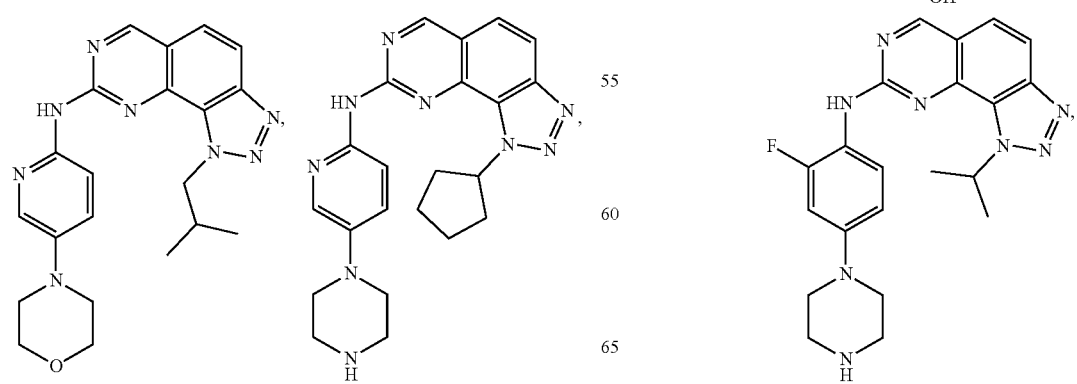

117
-continued
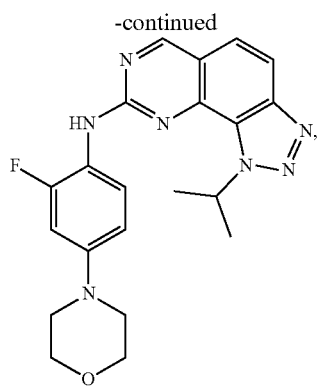
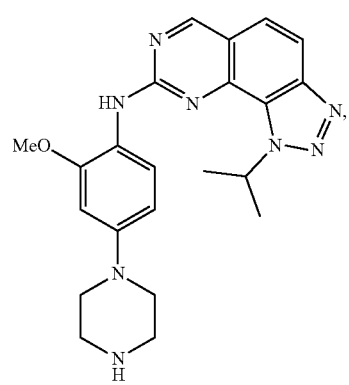
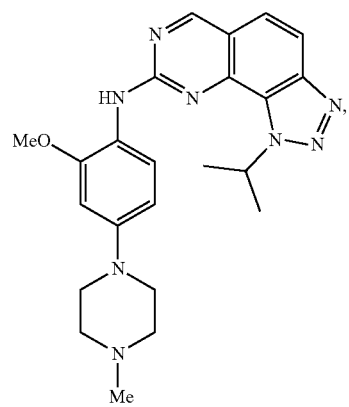
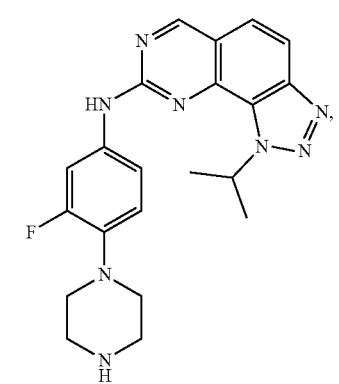
118
-continued
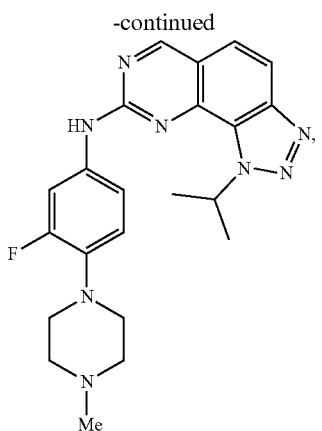
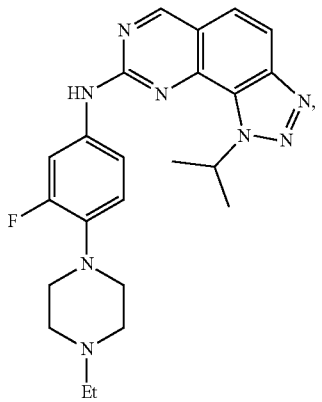
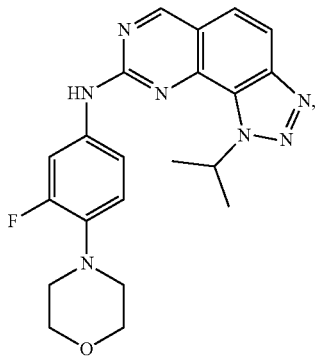
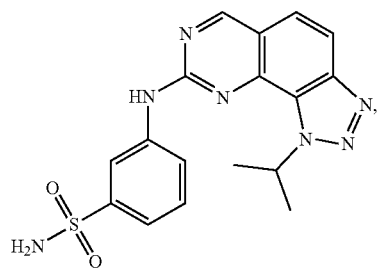

119
-continued
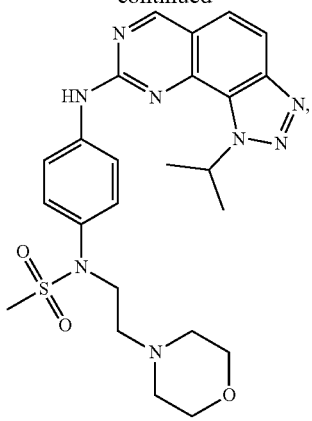
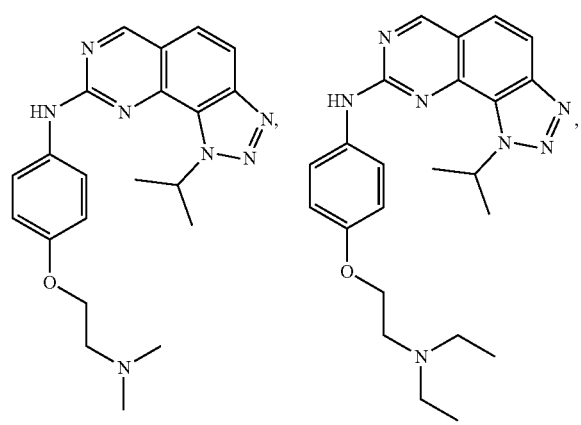
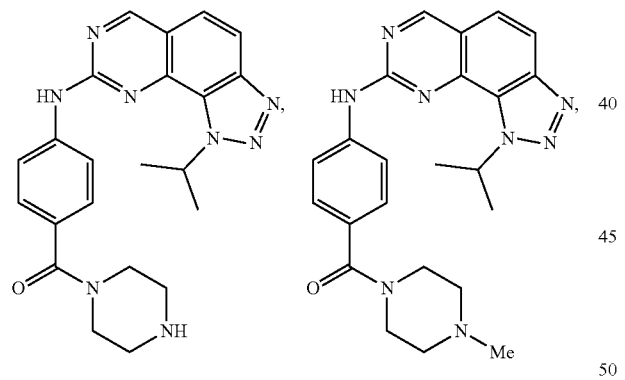
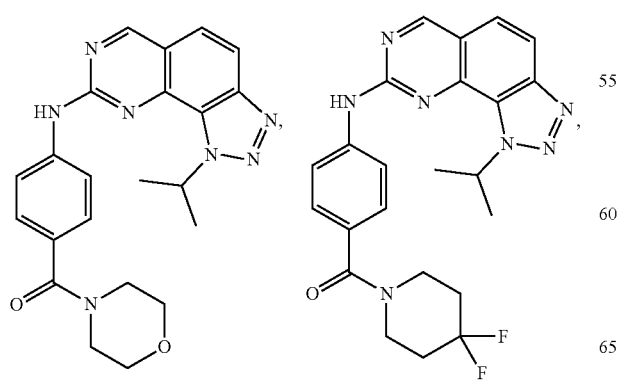
120
-continued
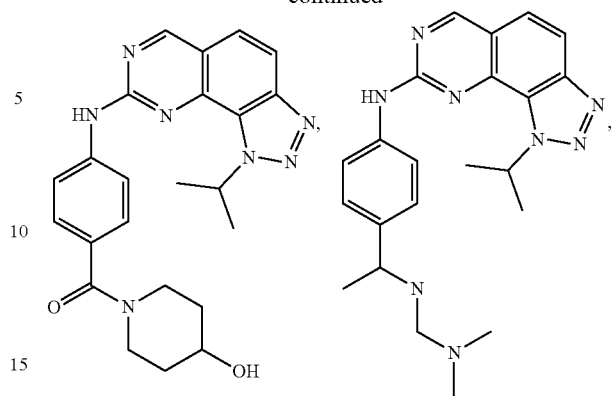
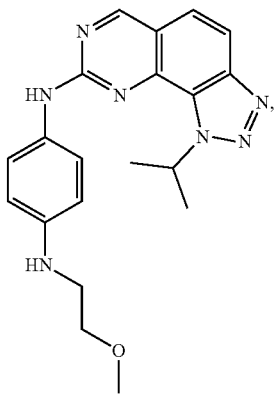
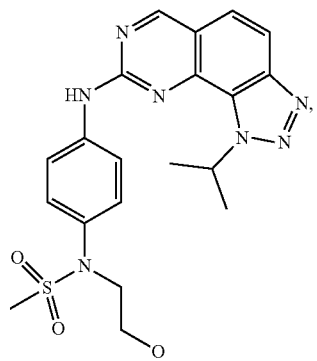
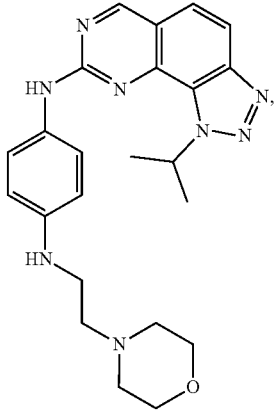

-continued

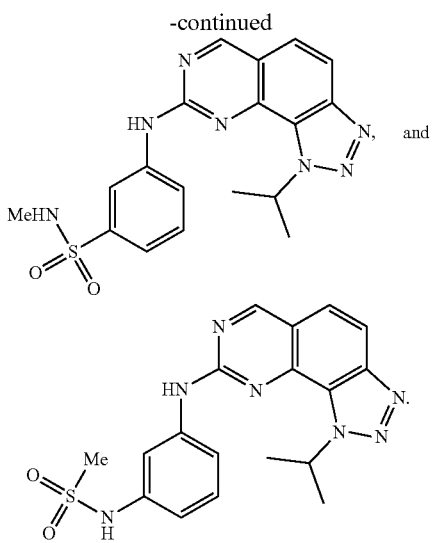

19. A pharmaceutical composition, comprising:
the compound, or the pharmaceutically acceptable salt, enantiomer, diastereomer, racemate, solvate, hydrate, polymorph, prodrug or isotopic variant thereof according to claim 1;
a pharmaceutically acceptable excipient; and
optionally, one or more other therapeutic agent(s).

20. A method of treating and/or preventing diseases mediated by CDK kinase in a subject, which comprises administering to the subject the compound, or the pharmaceutically acceptable salt, enantiomer, diastereomer, racemate, solvate, hydrate, polymorph, prodrug or isotopic variant thereof according to claim 1.

21. The method of claim 20, wherein the disease mediated by CDK kinase is cancer.

* * * * *